(12) United States Patent
Quinn et al.

(10) Patent No.: US 10,642,445 B2
(45) Date of Patent: May 5, 2020

(54) METHODS AND APPARATUS FOR PROCESSING MEDICAL DATA FROM A PLURALITY OF USERS

(71) Applicant: PATIENTKEY INC., Moffett Field, CA (US)

(72) Inventors: Patrick W Quinn, Pleasanton, CA (US); Michael S Malone, Sunnyvale, CA (US); Piyush Gupta, Fremont, CA (US)

( * ) Notice: Subject to any disclaimer, the term of this patent is extended or adjusted under 35 U.S.C. 154(b) by 1023 days.

(21) Appl. No.: 14/649,150

(22) PCT Filed: Nov. 29, 2013

(86) PCT No.: PCT/US2013/072501
§ 371 (c)(1),
(2) Date: Jun. 2, 2015

(87) PCT Pub. No.: WO2014/085775
PCT Pub. Date: Jun. 5, 2014

(65) Prior Publication Data
US 2016/0140296 A1    May 19, 2016

Related U.S. Application Data

(60) Provisional application No. 61/750,786, filed on Jan. 9, 2013, provisional application No. 61/732,390, filed on Dec. 2, 2012.

(51) Int. Cl.
*G06F 3/0481*    (2013.01)
*G06F 16/2457*    (2019.01)
(Continued)

(52) U.S. Cl.
CPC ........ *G06F 3/04817* (2013.01); *G06F 3/0482* (2013.01); *G06F 16/24578* (2019.01);
(Continued)

(58) Field of Classification Search
CPC ........ G06Q 50/22; G06Q 50/24; G16H 10/60; G16H 50/70; G16H 80/00; G16H 15/00;
(Continued)

(56) References Cited

U.S. PATENT DOCUMENTS 7,788,343 B2    8/2010    Haselhurst et al.
2010/0082369 A1    4/2010    Prenelus et al.
(Continued)

FOREIGN PATENT DOCUMENTS

KR    20100104820 A    9/2010
KR    20110137194 A    12/2011

OTHER PUBLICATIONS

PCT Application PCT/US2013/072501 International Search Report dated Mar. 13, 2014.

*Primary Examiner* — Joseph D Burgess
(74) *Attorney, Agent, or Firm* — Edward B. Weller

(57) ABSTRACT

In one embodiment, a computer-implemented method that comprises receiving, a user request from a first system user of a plurality of system users for a communication of health data with a health information system. The health information system includes a data store that stores health data related to the plurality of system users. The method further comprises providing to the first system user health data stored by a second system user in the data store based on access approval by the second system user in response to a user request for health data associated with the second system user; analyzing health data for a first group of system users if the user request is an analysis of health data associated with the first group of system users; providing to the first system user the analyzed health data; and communicating health data associated with the first system user to a second group of system users if the user request is a request
(Continued)

to communicate and the first system user has designated the system users of the second group of system users.

20 Claims, 72 Drawing Sheets

(51) Int. Cl.
*G06Q 50/24* (2012.01)
*G16H 10/60* (2018.01)
*G06F 19/00* (2018.01)
*G06F 3/0482* (2013.01)

(52) U.S. Cl.
CPC .............. *G06F 19/00* (2013.01); *G06Q 50/24* (2013.01); *G16H 10/60* (2018.01)

(58) Field of Classification Search
CPC ........ G16H 40/20; G16H 50/20; G16H 40/63; G16H 50/30; G16H 40/67; G16H 10/20; G16H 20/10; G16H 10/40; G16H 10/65; G16H 20/13; G16H 20/60; G16H 20/30; G16H 70/20; G16H 20/17; G16H 20/70; G16H 30/20; G16H 30/40; G16H 40/60; G16H 20/00; G16H 30/00; G16H 50/50; G16H 70/40; G06F 19/3418; G06F 2221/2141; G06F 19/00; G06F 19/328; G06F 19/325; G06F 19/321; G06F 19/3456; G06F 19/3462; G06F 19/3468; G06F 19/3481; G06F 19/324; G06F 19/326

See application file for complete search history.

(56) References Cited

U.S. PATENT DOCUMENTS

| | | | |
|---|---|---|---|
| 2011/0082794 A1* | 4/2011 | Blechman | G06F 19/328 705/50 |
| 2012/0226771 A1 | 9/2012 | Harrington et al. | |

\* cited by examiner

CUSTOMER RANKING

★★★★★  TOTAL (1,138) ──────4506
★★★★★  ──────────────────────
★★★★★  PKP
★★★★★  PATIENT (1,135) ▶
★★★★★  PROVIDER (3) ▶

─────4504
FDA ICON

▶ RANK ME

CUSTOMER REVIEWS

GLUCOSE BUDDY IS MY BUDDY ★★★★★
RANDY MEYERS  PATIENT
DATE: 11/28/2012  TIME: 19:26

─────4502
★★★★★  DR. AMY JAMES
★★★★★  DR. GREG STANLEY
★★★★★  DR. MARK COOPER  ⊗

I LOVE THE GRAPHING FEATURE. IT HELPS ME TO COMMUNICATE WITH MY DOCTOR BETTER.

GREAT APP! ★★★★★
DR. MARK COOPER  PROVIDER
DATE: 11/28/2012  TIME: 18:07

I USE IT ALL THE TIME. IT IS A GREAT APP TO KEEP TRACK OF YOUR BLOOD GLUCOSE LEVELS.

GOOD DIABETES TRACKER ★★★★★
RICHARD DANT  PATIENT
DATE: 11/27/2012  TIME: 09:05

IT'S A TERRIFIC AID IN TRACKING DIABETES. I USE IT EVERY DAY!

...LESS

CUSTOMERS ALSO BOUGHT

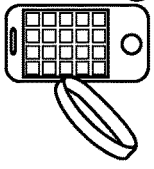  NIKE+ FUELBAND
HEALTH & FITNESS
$149.95 BUY DEVICE & APP

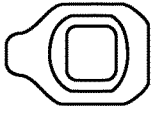  FITBIT ZIP
HEALTH & FITNESS
$59.95 BUY DEVICE & APP

  FITNESS BUDDY
HEALTH & FITNESS
$0.99 BUY APP

© 2012 PATIENTKEY, INC.   ABOUT PATIENTKEY   CONTACT   PRIVACY   LEGAL

+PATIENTKEY
PATIENT: WELCOME MIKE MALONE

MY APPS | ◇ MARKET PLACE | ACCOUNT INFO | LOG OUT | SEARCH

MARKETPLACE > BLOOD GLUCOSE > AZUMIO, INC.         CUSTOMER RANKING ★★★★☆   RANK ME   DETAILS

- RESULTS/VITALS
- PERSONAL DATA
- DATA SHARING
- DEVICE DATA
- HEALTH APPS
- RANKINGS
- HISTORY

GLUCOSE BUDDY - DIABETES LOGBOOK MANAGER W/ SYNCING, BLOOD PRESSURE, WEIGHT TRACKING
BY AZUMIO, INC.

DESCRIPTION
- RANKED #1 DIABETES IPHONE APPLICATION BY MANNY HERNANDEZ, FOUNDER OF TUDIABETES.COM
- AS SEEN IN AMERICAN DIABETES ASSOCIATION'S DIABETES FORECAST MAGAZINE, WIRED MAGAZINE, DIABETESMINE.COM, MEDGADGET.COM, MENDOSA.COM, DIABETES HEALTH MAGAZINE, JDRF NEWSLETTERS AND MOBILHEALTHNEWS

GLUCOSE BUDDY IS A DATA STORAGE UTILITY FOR PEOPLE WITH DIABETES. USERS CAN MANUALLY ENTER GLUCOSE NUMBERS, CARBOHYDRATE CONSUMPTION, INSULIN DOSAGES, AND ACTIVITIES. THEN, YOU CAN VIEW ALL OF YOUR DATA ON YOUR FREE GLUCOSEBUDDY.COM ONLINE ACCOUNT

- 12,000,000+ LOGS UPLOADED TO LINKED ONLINE ACCOUNTS

FEATURES:                                                               MORE...

UPGRADE APP
CATEGORY: MEDICAL
UPDATED: OCT 04, 2012
VERSION: 3.7.0
SIZE: 11.7 MB
LANGUAGE: ENGLISH
SELLER: TOM XU
© AZUMIO INC.

RESULTS/VITALS

LAST DATA CAPTURE: ◀ 10:12:30 ON 11/26/2012 ▶

HR (BPM): 86            QT (MS): 486
PR (MS): 142            QTC (MS): 142
QRS (MS): 98             PRT (°): 32  20  13
GRID LEGEND: 1 BLOCK == 0.1MV/.04SEC

CUSTOMER RANKING

KAISER PERMANENTE ® POWERED BY PATIENTKEY | ◇ MY PATIENTS | ◇ MARKET PLACE | 🔍 ACCOUNT INFO | LOG OUT | 🔍 SEARCH

PROVIDER: WELCOME, DR. WILL JONES!

- RESULTS/VITALS
- PROVIDER DATA
- DEVICE DATA
- HEALTH APPS
- PRESCRIPTIONS
- RANKINGS
- ANALYTICS

ALL | PRIORITY | WATCH LIST | ALERTS | OTHER PATIENTS

PRIORITY  ABC ⊙

| | | STATUS | AVERAGE ADHERENCE | NEXT APPOINTMENT | RESULTS/VITALS | |
|---|---|---|---|---|---|---|
| ■ | MARY SMITH [1] | P ⊙ | 67% | 12/16/2012 - 1200 | GLUCOSE BUDDY: BP 210, PR (MS) 146, QR... | ⋀ |
| □ | JEFF GRIFFIS [2] | P ⊙ | 43% | 02/12/2013 - 0900 | FITNESS BUDDY: GT (MS) 486, QTC (MS) 142... | ⋀ |
| □ | JESSICA STEFFAN [3] | P ⊙ | 50% | 02/02/2013 - 1200 | PILLBOXIE: MISSED COREG FRIDAY DECEMBER... | ⋀ |
| □ | CODY BLAGG [4] | P ⊙ | 52% | 12/22/2012 - 1300 | CARDIO BUDDY: QRS (MS) 107, PRT (I) 32 2... | ⋀ |
| □ | CURTIS UYEMOTO [5] | P ⊙ | 83% | TODAY - 0900 | CARDIOGRAPH: NORMAL READING ☐ DIABET... | ⋀ |

WATCH LIST  ABC ⊙

| | | STATUS | AVERAGE ADHERENCE | NEXT APPOINTMENT | RESULTS/VITALS | |
|---|---|---|---|---|---|---|
| ■ | TAYLOR MCCUTEON [1] | W ⊙ | ABCDEFGHIJKLMNOPQRST UVWXYZ ⊗ | | E CALORIC INTAKE LAST MONT... | ⋀ |
| □ | DANIEL MILLER [2] | W ⊙ | 50% | TOMORROW - 0800 | PILLBOXIE: MISSED SULFONYLUREAS TUESDAY, D... | ⋀ |
| ■ | JACOB MILLER [3] | W ⊙ | 22% | 01/05/2013 - 1500 | DIABETES NUTRITION: BLOOD GLUCOSE AVERAG... | ⋀ |

ALERTS  ABC ⊙

| | | STATUS | AVERAGE ADHERENCE | NEXT APPOINTMENT | RESULTS/VITALS | |
|---|---|---|---|---|---|---|
| ■ | STEPHANIE BOWLMANN [1] | A ⊙ | 49% | TODAY - 1000 | PATIENT: CHEST PAINS MONDAY, DECEMBER 3... | ⋀ |
| □ | ERIC GREENWOOD [2] | | | 04/06/2013 - 1400 | GLUCOSE BUDDY: RESTING HR (BPM) 103, PU... | ⋀ |

PRIORITY
WATCH LIST
OTHER PATIENTS
RESULTS/VITALS OK

OTHER PTS  ABC ⊙

| ADHERENCE | NEXT APPOINTMENT | RESULTS/VITALS |
|---|---|---|

KAISER PERMANENTE ® POWERED BY PATIENTKEY | ⬦ MY PATIENTS | ⬦ MARKET PLACE | & ACCOUNT INFO | LOG OUT | 🔍 SEARCH

PATIENT: WELCOME, MARY SMITH

- 5912 RESULTS/VITALS
- 5914 PERSONAL DATA
- 5916 DATA SHARING
- 5918 DEVICE DATA
- 5920 HEALTH APPS
- 5922 RANKINGS
- 5924 HISTORY 5902 5904 5906 5908

5900

GLUCOSE BUDDY
MEDICAL

BP: 160  QT: (MS): 486
PR: (MS): 142  QTC (MS): 142
QRS (MS): 98  PRT (°): 32  20  13
GRID LEGEND: 1 BLOCK == 0.1MV/.04SEC

FITNESS BUDDY...
HEALTH & FITNESS

DIABETES TRACKER...
MEDICAL

CARDIO BUDDY
HEALTH & FITNESS

© 2012 PATIENTKEY, INC.     ABOUT PATIENTKEY   CONTACT   PRIVACY   LEGAL

FIG. 59

METHODS AND APPARATUS FOR PROCESSING MEDICAL DATA FROM A PLURALITY OF USERS

RELATED APPLICATION

This application is a U.S. National Phase Application under 35 USC 371 of International Application PCT/US2013/072501, filed Nov. 29, 2013, which claims benefit of, and priority under 35 USC § 119(e) from U.S. provisional application No. 61/732,390, filed Dec. 2, 2012, and claims benefit of, and priority under 35 USC § 119(e) from U.S. provisional application No. 61/750,786, filed Jan. 9, 2013, which are all incorporated by reference herein in their entirety.

This application claims benefit of, and priority under 35 USC § 119(e) from U.S. provisional application No. 61/750,786, filed Jan. 9, 2013, which is incorporated by reference herein in its entirety.

BACKGROUND

The disclosure relates to methods and systems for processing medical data, and in particular, to methods and systems for processing medical data from health care providers, payers and patients.

The healthcare system is experiencing extreme upheaval. The costs of insurance, medical care, and pharmaceuticals are escalating. The aging population is adding a severe strain to an already burdened system.

Further, both providers and payers typically have a transactional mindset for health care. Both providers and payers view medical care and payment as a series of transactions, rather than a process.

Further, there is a proliferation of dedicated personal healthcare devices, such as physical activity sensors or blood sugar meters, and smart phones and tablets have personal healthcare applications. However, these devices provide data only to the patient, either directly from the device, or to the patient's healthcare application.

FIG. 1 is a block diagram illustrating data flow in a conventional health data system 100. Conventional health data system 100 comprises a patient 108, a health information exchange/electronic health record (HIE/EHR) system 110, a health data source developer 112, an analytics developer 114, a hospital 120, a physician 122, a health data source 127, an insurance company 128, and a government entity 129.

The data communication in the conventional health data processing system 100 is via discrete communication links. Patient 108 communicates separately with health data source developer 112, hospital 120, physician 122, health data source 127, insurance company 128 and government entity 129. Hospital 120 communicates separately with HIE/EHR system 110, health data source developer 112, physician 122, insurance company 128, and government entity 129. Health data source developer 112 communicates separately with physician 122 and health data source 127. Analytics developer 114 communicates with health data source developer 112 and health data source 127. The numerous communication links increases with increasing numbers of patient 108, health data source developer 112, analytics developer 114, hospital 120, physician 122, health data source 127, insurance company 128 and government entity 129.

It is desirable to have a system that processes medical data from various sources.

SUMMARY

Embodiments of the present invention include systems and methods for processing medical data. In one embodiment, the present invention includes a computer-implemented method that comprises receiving, by a controller, a user request from a first system user of a plurality of system users for a communication of health data with a health information system. The health information system includes the controller and a data store that stores health data related to the plurality of system users. The method further comprises providing to the first system user, by the controller, health data stored by a second system user in the data store based on access approval by the second system user in response to a user request for health data associated with the second system user; analyzing, by the controller, health data for a first group of system users if the user request is an analysis of health data associated with the first group of system users; providing, by the controller, to the first system user the analyzed health data; and communicating, by the controller, health data associated with the first system user to a second group of system users if the user request is a request to communicate and the first system user has designated the system users of the second group of system users.

In another embodiment, the present invention includes a computer readable medium embodying a computer program for performing a method and embodiments described above.

In another embodiment, the present invention includes a computer system comprising one or more processors implementing the techniques described herein.

The following detailed description and accompanying drawings provide a better understanding of the nature and advantages of the present invention.

BRIEF DESCRIPTION OF THE DRAWINGS

FIG. 45 illustrates a screenshot for ranking a health data source.

FIG. 46 illustrates a screenshot for ranking health applications and health data sources.

FIG. 47 illustrates a screenshot for health applications available to a patient in the marketplace.

FIG. 48 illustrates a screenshot for a health data source that a physician can evaluate for recommending or prescribing to patients.

Figure 49:
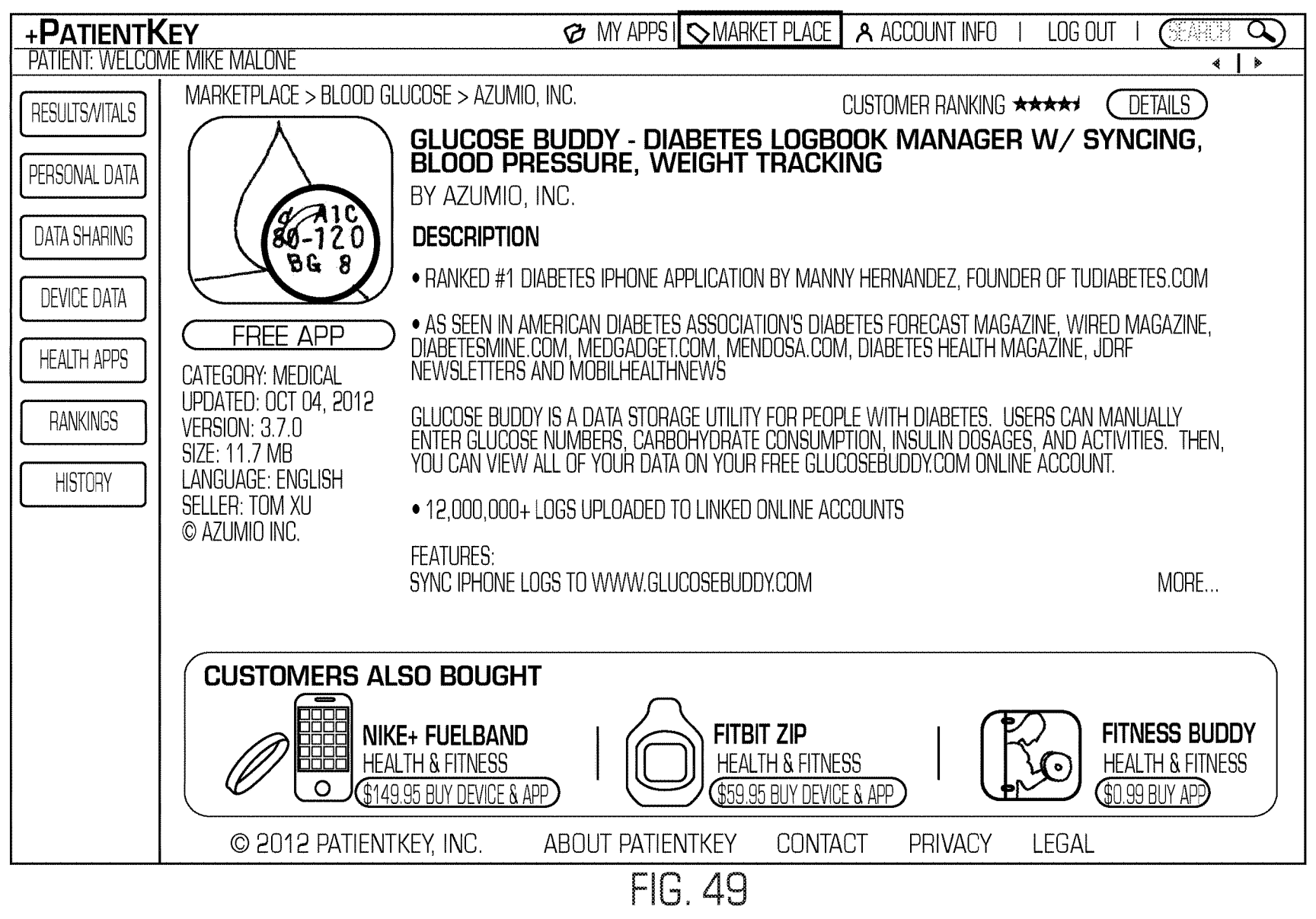

FIG. 49 illustrates a screenshot for a health data source that a patient can evaluate for purchase.

FIG. 50 illustrates a screenshot of consolidation of health applications and health data sources of a patient.

FIG. 56 illustrates a screenshot of patients of a provider in the process of FIGS. 15a and 15b.

FIG. 57 illustrates a screenshot of a patient selected by a provider from the screenshot of FIG. 56.

FIG. 59 illustrates a screenshot of consolidated data of a health data device of a patient.

DETAILED DESCRIPTION

Figure 1:
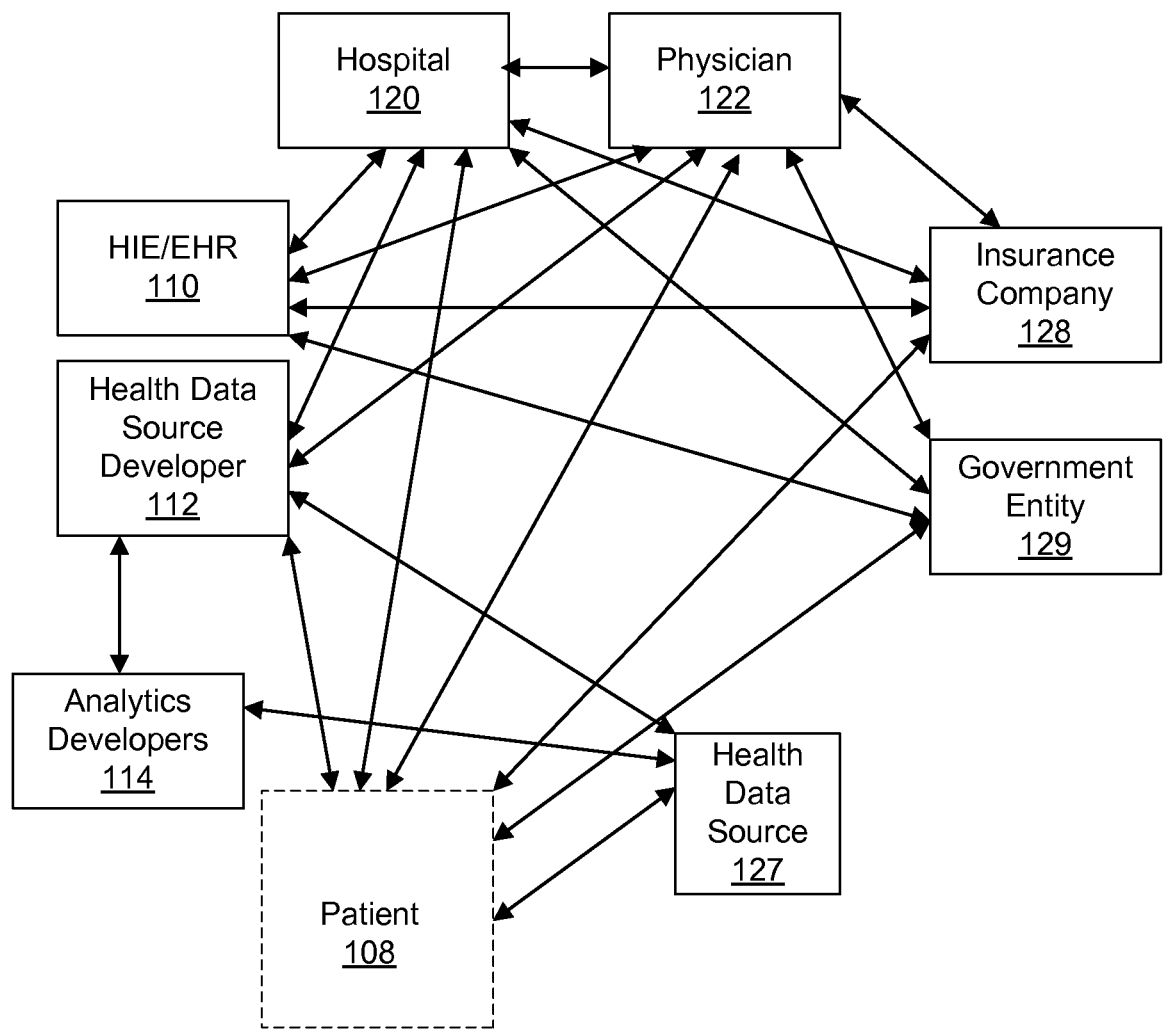
FIG. 1 is a block diagram illustrating data flow in a conventional health data system.

Various embodiments of the present invention are now described with reference to the figures where like reference numbers indicate identical or functionally similar elements. Also in the figures, the left most digits of each reference number corresponds to the figure in which the reference number is first used.

Reference in the specification to "one embodiment", "an embodiment", "various embodiments" or "some embodiments" means that a particular feature, structure, or characteristic described in connection with these embodiments is included in at least one embodiment of the invention, and such references in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

Figure 2:
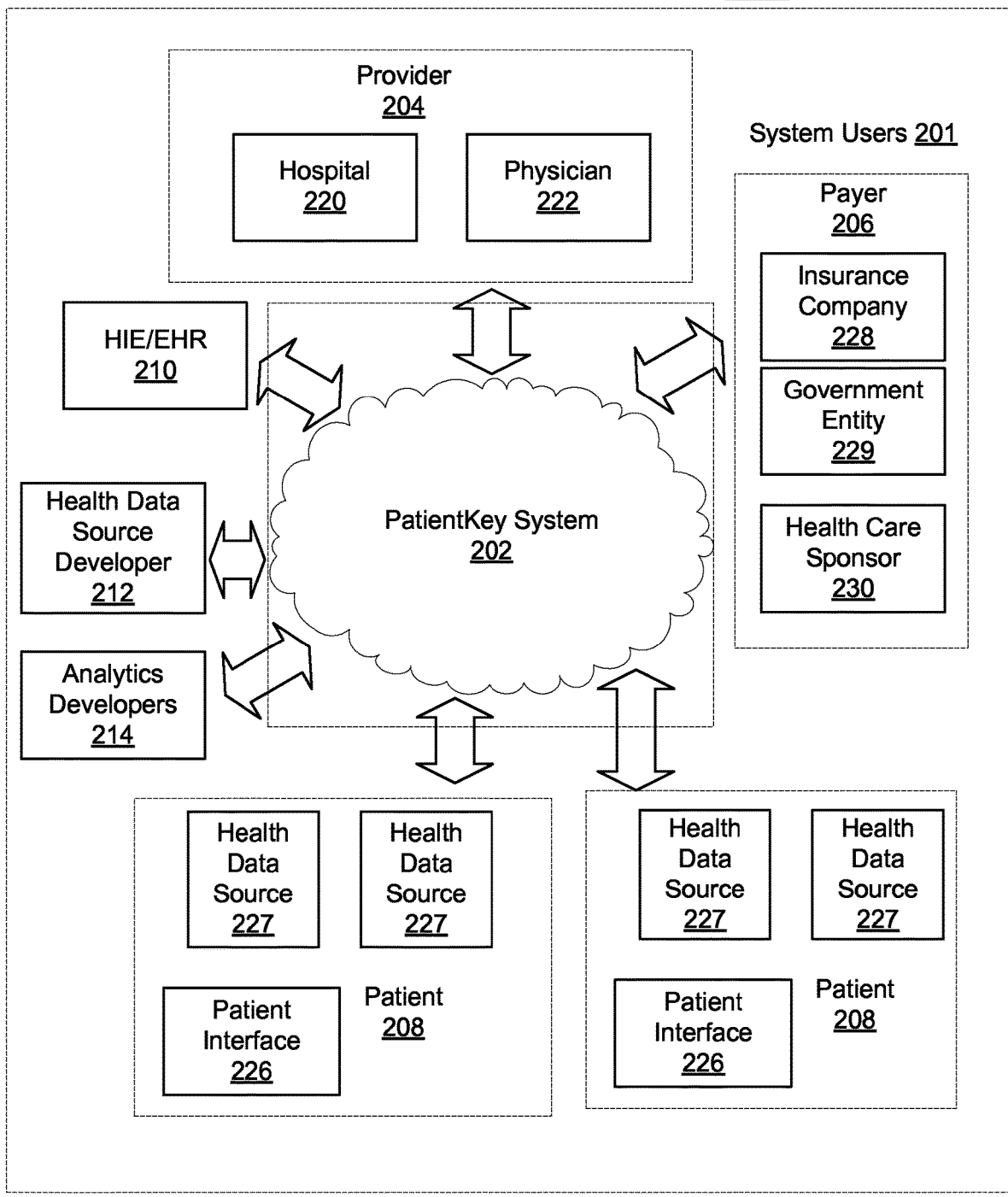
FIG. 2 is a block diagram illustrating a health data processing system according to innovations herein.

FIG. 2 is a block diagram illustrating a health data processing system 200 according to innovations herein. Health data processing system 200 comprises a plurality of system users 201 and a health information processing system 202. For convenience, references to health information processing system 202 are shown in some of the Figures as PatientKey™ or PatientKey™ system. PatientKey™ is a trademark of PatientKey Inc. System users 201 comprises a plurality of providers 204, a plurality of payers 206, a plurality of patient systems 208, a health information exchange/electronic health record (HIE/EHR) system 210, a plurality of health data source developers 212, and a plurality of analytics developers 214. For convenience, a patient using patient system 208 is also referred to as patient 208. For simplicity and clarity, only one health data source developer 212 and only one analytics developer 214 are shown. Also, for simplicity and clarity, only two patient systems 208 are shown. Health data processing system 200 may include any number of patient systems 208, health data source developer 212 and analytics developer 214.

Health information processing system 202 provides and facilitates communication, either real-time or delayed, between system users 201. For example, health information processing system 202 communicates medical and health monitoring data about a patient, for example, information about a patient's chronic disease, such as blood sugar for a diabetic patient, and provides the blood sugar information to providers 204. In some embodiments, patient 208 enables access to the data from patient system 108, which may include sensors of the patient. Data may be communicated between system users 201 and health information processing system 202 at times selected by the system user 201 generating the data, or in some instances, by other system users 201. For example, patient 208 may control download of data to health information processing system 202, and in some instances, a provider 204 may control either in real-time or at a selected time the download of data.

Health information processing system 202 provides systems and procedures for various system users 201 to rank other system users 201. Ranking is described further in conjunction with FIGS. 39-46.

Health information processing system 202 provides tools for processing the data received from system users 201. Health information processing system 202 receives data from patient system 208, and processes the data to analytics developer 214 to develop or update the health application analytics. Health information processing system 202 may process the data to assist providers 204 in providing medical care or wellness care to patient 208. Health information processing system 202 processes data for chronic disease management, general health, and athletic performance. Health information processing system 202 stores data for long-term disease management.

Health information processing system 202 provides security for protecting data stored in health information processing system 202 and communicated between health information processing system 202 and system users 201. Health information processing system 202 authenticates people or systems trying to access health information processing system 202 as authorized system users 201. Health information processing system 202 may include a telephone call center for system users 201 to communicate with health information processing system 202.

In some embodiments, health information processing system 202 provides an open application program interface for use and development of health data source developers 212 and analytics developers 214.

In various embodiments, health information processing system 202 allows patients 208 to import data from patient selected health data sources 227.

In various embodiments, health information processing system 202 provides data mining of data for individual patient 208, health application, or health data source 227 or groups of patients 208, health applications, or health data sources 227.

In various embodiments, health information processing system 202 provides information and services to patient 208 to take more control and responsibility for health decisions and have more information during visits with providers 204. Health information processing system 202 provides information and recommendations to patient 208 regarding behavior change for improved health. Health information processing system 202 detects patterns of data across health data sources 227 to encourage or reinforce positive behavior changes by patient 208. Health information processing system 202 provides a platform for patient 208 (or other system users 201) to share information, either for specific health applications or health data sources 227 or in bundles, with selected individuals, groups, or system users 201. The bundles may be, for example, groups of health applications, groups of health data sources 227 or groups of both health applications and health data sources 227.

Providers 204 provide medical care, services, or treatment to patient 208. In some embodiments, providers 204 include a plurality of hospitals 220 and a plurality of physicians 222. For simplicity and clarity, only one hospital 220 and only one physician 222 are shown. Providers 204 may use health information processing system 202 to search for health data sources 227 and health applications to prescribe to patients 208. Providers 204 may rank health data sources 227 and health applications using health information processing system 202. Providers 204 may use health information processing system 202 to receive patient data from patient 208 or patient data that is analyzed by health information processing system 202.

Payers 206 provide approval or disapproval for medical services provided by providers 204 and provide payment for such approved medical services. In some embodiments, payers 206 comprise at least one insurance company 228. In some embodiments, payers 206 comprise at least one government entity 229, such as a Federal agency that administers Medicare. In some embodiments, payers 206 comprise at least one health care sponsor 230, such as an employer or union.

Patient system 208 communicates data about the patient to health information processing system 202. In some embodiments, patient system 208 includes a patient interface 226 for communicating with the patient. Patient interface 226 may includes a web browser. In some embodiments, patient system 208 includes at least one health data source 227. For simplicity and clarity, only two health data sources 227 are shown. Patient system 208 may download data entered by patient 208 on patient interface 226 or downloaded from a health data source 227 to health information processing system 202 with access authorization determined by patient 208. Patient 208 may search health information processing system 202 for health applications or health data sources 227 for purchase and use, research health applications or health data sources 227 prescribed by provider 204 or recommended by payer 206. Patient 208 may use health information processing system 202 to rank health applications or health data sources 227.

Health data source 227 may monitor one or more physiological parameters of one or more body systems of the patient. In some embodiments, health data source 227 monitors the circulatory system of the patient by monitoring, for example, heart rate or blood pressure.

In some embodiments, health data source 227 includes applications in a personal device of the patient, such as a smart phone, tablet, or personal computer.

In some embodiments, health data source 227 monitors blood chemistry, such as glucose or blood oxygen.

In some embodiments, health data source 227 provides health maintenance to patient 208. Such health data source 227 may be, for example, an oxygen source or a continuous positive air pressure (CPAP) device.

In some embodiments, health data source 227 includes fitness, activity or wellness monitors, such as devices that monitor physical movement of the patient.

Health information exchange/electronic health record (HIE/EHR) system 210 stores information about individual patients or populations.

Health data source developer 212 uses health information processing system 202 to receive data from health data sources 227 that may or may not be analyzed by health information processing system 202 and rankings by patients 208, providers 204 and payers 206. Health data source developer 212 uses health information processing system 202 to publish interface specifications for health data sources 227 for development of health applications by analytics developers 214.

Analytics developer 214 uses health information processing system 202 to receive data from health data sources 227 that may or may not be analyzed by health information processing system 202, rankings by patients 208, providers 204 and payers 206, and interface specifications for health data sources 227 from health data source developers 212 to develop or modify health applications. Analytics developer 214 uses health information processing system 202 to post health applications to a health application store, either operated by health information processing system 202 or a third party.

In health information processing system 202 described herein, patients 208 may take more control of their health. Health information processing system 202 provides information to patients 208 that can encourage and reinforce positive behavior changes of the patients. Health information processing system 202 consolidates data from multiple health data sources 227, and may do such with more than one health application or device per portal. Health information processing system 202 may user browser, tablet or other user interfaces with which the patient is familiar, and process data to improved remote communication and coordination between patients 208 and providers 204. Health information processing system 202 allows patients 208 to share or bundle information with family and friends, and to associate with like sufferers.

In health information processing system 202 described herein, health information processing system 202 may aggregate, filter, and secure actionable patient data to providers 204. This data allows providers 204 to ensure improved patient adherence to treatment regimes. Health information processing system 202 provides access, expansion, or may create a marketplace for health applications and health data sources 227.

In the health information processing system 202 described herein, health information processing system 202 may reduce costs for payers 206 by improving compliance and wellness by patients 208 and optimizing care from nurse practitioners and other non-physician health care providers. Health information processing system 202 provides analytics on data patients 208 whose identity is redacted so patients 208 are anonymous.

In the health information processing system 202 described herein, health information processing system 202 may provide a common data platform that allows data aggregation across health data sources 227. The access to the marketplace by health information processing system 202 expands awareness of health data sources 227 by other system users 201, and in particular, patients 208, physicians 222, and analytics developers 214.

In the health information processing system 202 described herein, health information processing system 202 may provide a common data platform that allows interfacing to all data sources by analytics developers 214. The access to the marketplace by health information processing system 202 expands access to health data sources 227 for analytics developers 214.

In various embodiments, health information processing system 202 stores a record of each transaction, or a specified type of transactions, by system users 201 or types of systems users 201 with health information processing system 202. Such records may be used for audits. For example, provider 204 may be a network of physicians 222 and nurses that each access health information processing system 202 for a group of patients 208. Health information processing system 202 records each transaction by each physician 222 and each nurse. In addition to a physician 222 or nurse being able to determine who made an early entry or change, the records stored in health information processing system 202 may be used to determine who accessed the records.

Figure 3:
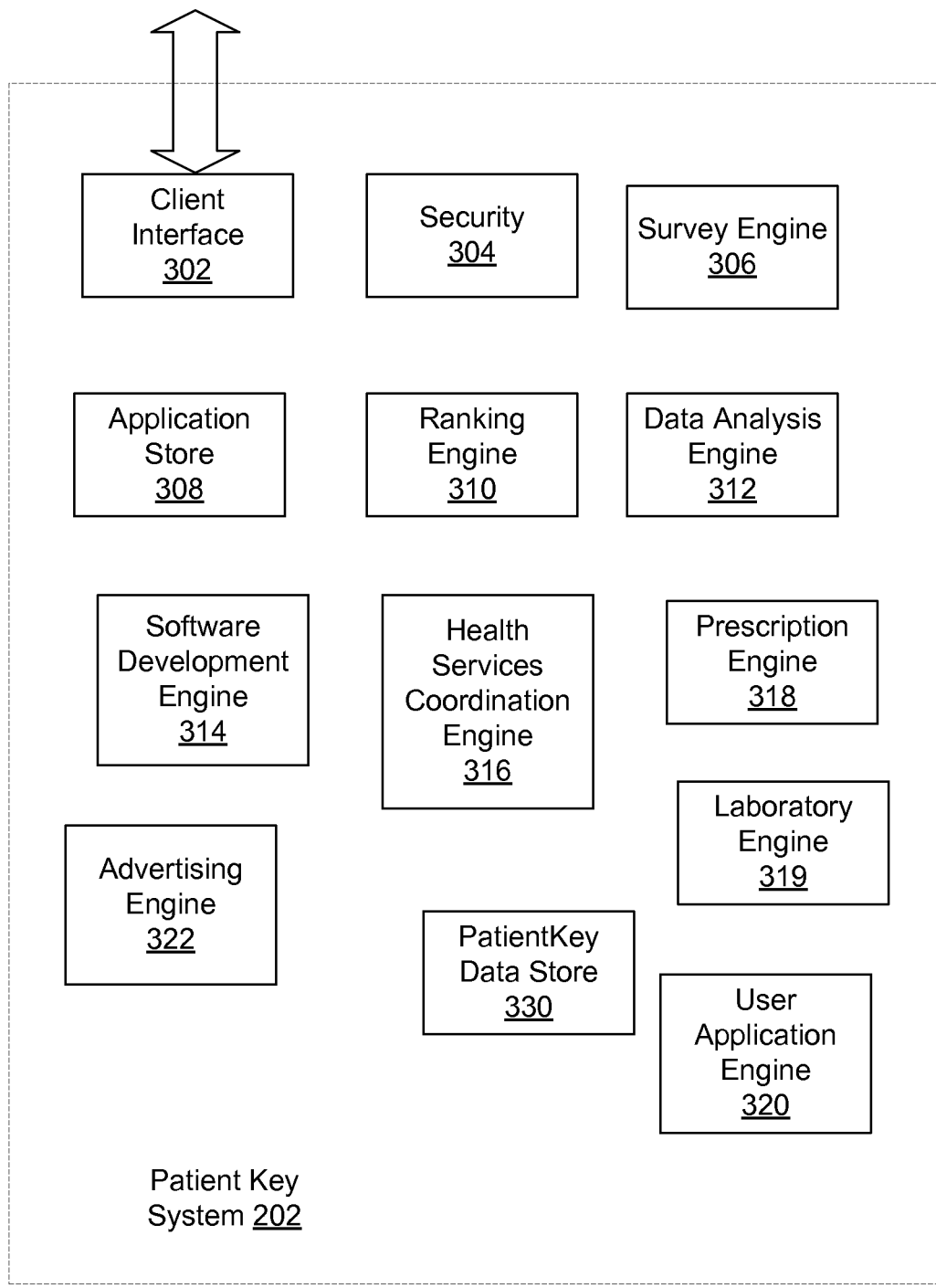
FIG. 3 is a block diagram illustrating a health information processing system of the health data processing system of FIG. 2.

FIG. 3 is a block diagram illustrating health information processing system 202. Health information processing system 202 comprises a client interface 302, a security engine 304, a survey engine 306, an application store 308, a ranking engine 310, a data analytics engine 312, a software development engine 314, a health services coordination engine 316, a prescription engine 318, a laboratory engine 319, a user application engine 320, an advertising engine 322, and a data store 330.

Client interface 302 provides a communication interface between health information processing system 202 and system users 201. In some embodiments, client interface 302 is an interface for communicating over the Internet using a Transmission Control Protocol/Internet Protocol (TCP/IP).

Security engine 304 provides security for protecting data stored in health information processing system 202 and communicated between health information processing system 202 and system users 201. Security engine 304 encrypts data stored in data store 330 or communicated over client interface 302, such as per protocols to comply with laws and regulations (e.g., Health Insurance Portability and Accountability Act of 1996 (HIPPA)). Security engine 304 authenticates people or systems trying to access health information processing system 202 as an authorized system users 201.

Survey engine 306 generates surveys of usage by system users 201.

Application store 308 generates an ecommerce source for patients 208 to purchase or download healthcare applications to their health data source 127. Analytics developer 214 may also provide the healthcare applications to health information processing system 202 for evaluation and inclusion in application store 308.

Ranking engine 310 processes rankings made by system users 201 to generate composite rankings for the various system users 201 and an overall composite ranking Ranking is described further in conjunction with FIGS. 39-46.

Data analytics engine 312 analyzes the data from system users 201 to generate rankings, regulatory compliance, patient device usage, health trends, efficacy of devices, health applications, and other processing of data from patient 208, health data source 227, health application, medication, providers 204 and payer 206. Data analytics engine 312 may group or analyze patient data based on various parameters, including, for example, employer, geography, gender, ethnicity, age, lifestyle, lifestyle, personal data, personal health, medications, health data sources 227, health applications, system user 201 browsing history, services used by system user 201 or imported data from HIE/EHR 210.

Data analytics engine 312 analyzes the data from system users 201 to detect health trends of patients 208 to determine potential chronic health conditions.

Software development engine 314 is used by developers to write software for health information system 202.

Health services coordination engine 316 coordinates health care services to patients 208 based on input from hospitals 220 or physicians 222. The health care services may be, for example, home health services provided by a nurse or other health service worker at the home of a patient 208.

Prescription engine 318 coordinates prescriptions made by providers 204 with patients 208 and corresponding pharmacies.

Laboratory engine 319 coordinates laboratory tests prescribed or ordered by providers 204 for patients 208 at laboratories. Laboratory tests may be, for example, blood tests, stool tests, urine test, imaging tests, radiology tests, and the like.

User application engine 320 processes requests from system users 301 and generates user interface information, such as screenshots on a browser. User application engine 320 allows system users 201 access to data as authorized by other system users 201 that provide the data. User application engine 320 distributes data from one system user 201 to another system user 201 based on requests from that one system user 201.

Advertising engine 322 processes advertising and promotion on health information processing system 202 by system users 201 for display on web pages. User application engine 320 processes requests from system users 301 and generates user interface information, such as screenshots on a browser.

Data store 330 stores data from system users 201 or processed by health information processing system 202. Data store 330 stores data for long-term disease management.

Figure 4:
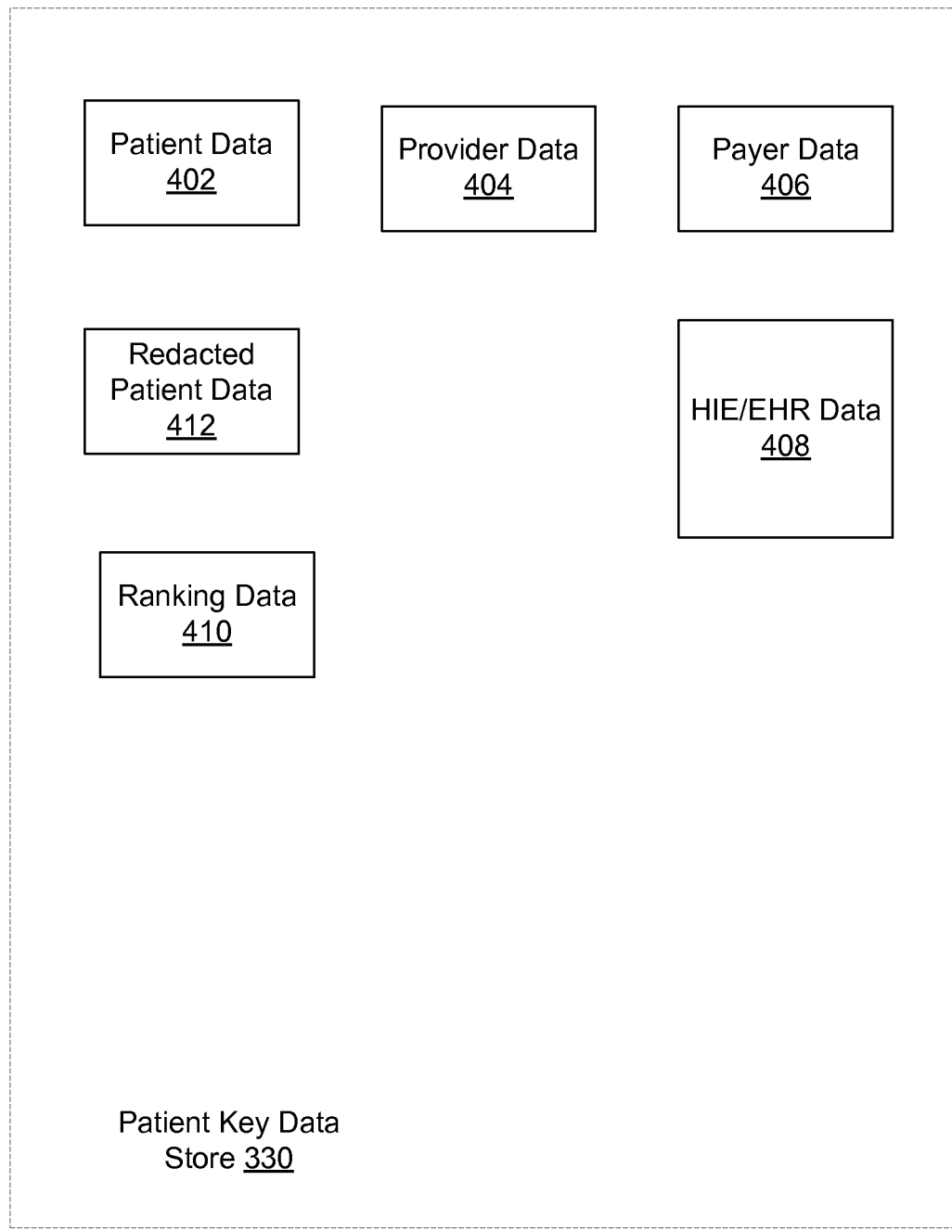
FIG. 4 is a block diagram illustrating a data store of the health information processing system of FIG. 3.

FIG. 4 is a block diagram illustrating data store 330. Data store 330 comprises a patient data store 402, a provider data store 404, a payer data store 406, and a HIE/EHR data store 408 for storing data received from patient systems 208, providers 204, payers 206, and HIE/EHR system 210, respectively. Data store 330 further comprises a redacted patient data store 412 for storing patient data that has patient identifiers removed.

Figure 5A:
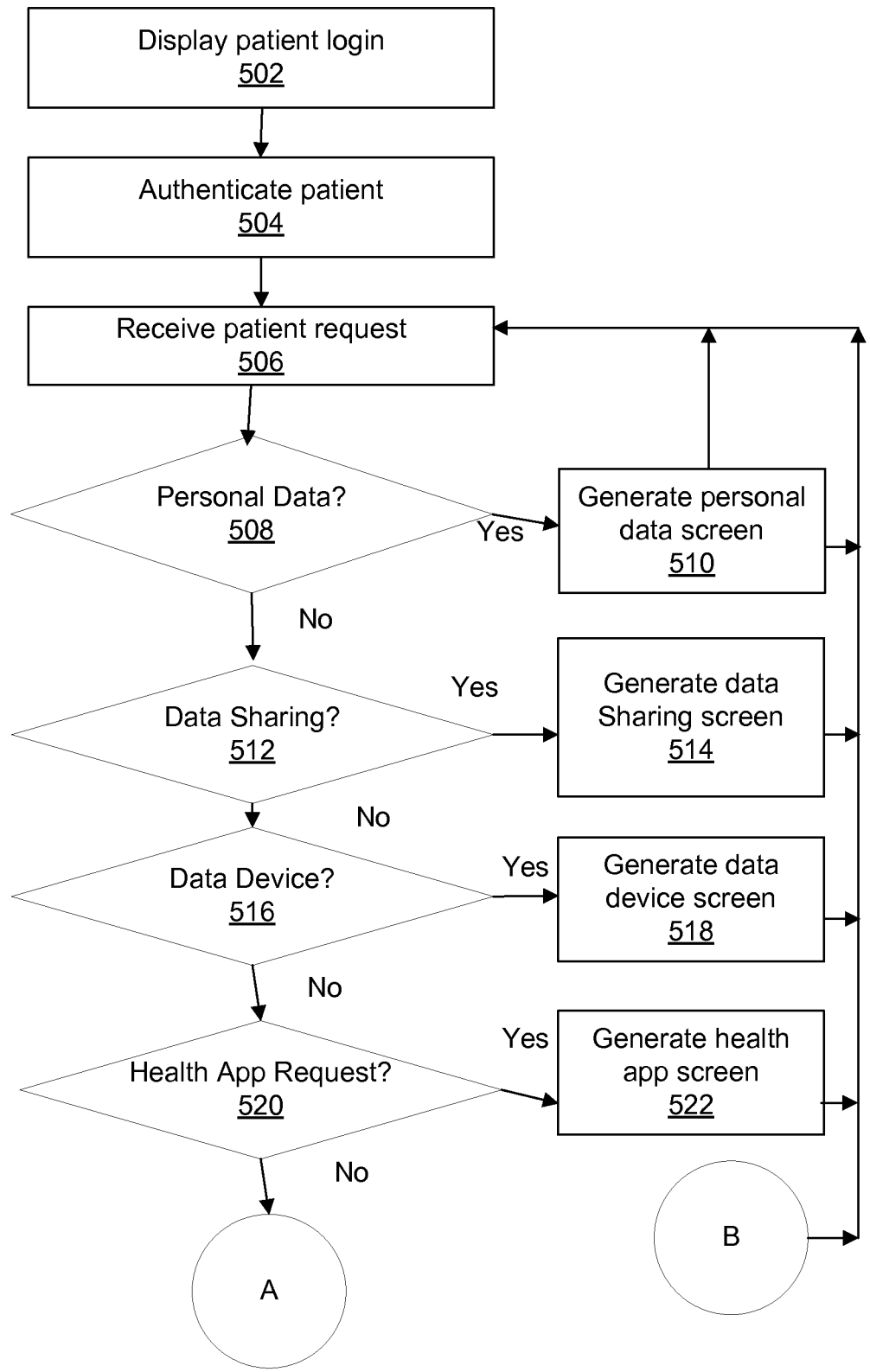
FIGS. 5a and 5b illustrate a process for the health data processing system of FIG. 2.
Figure 5B:
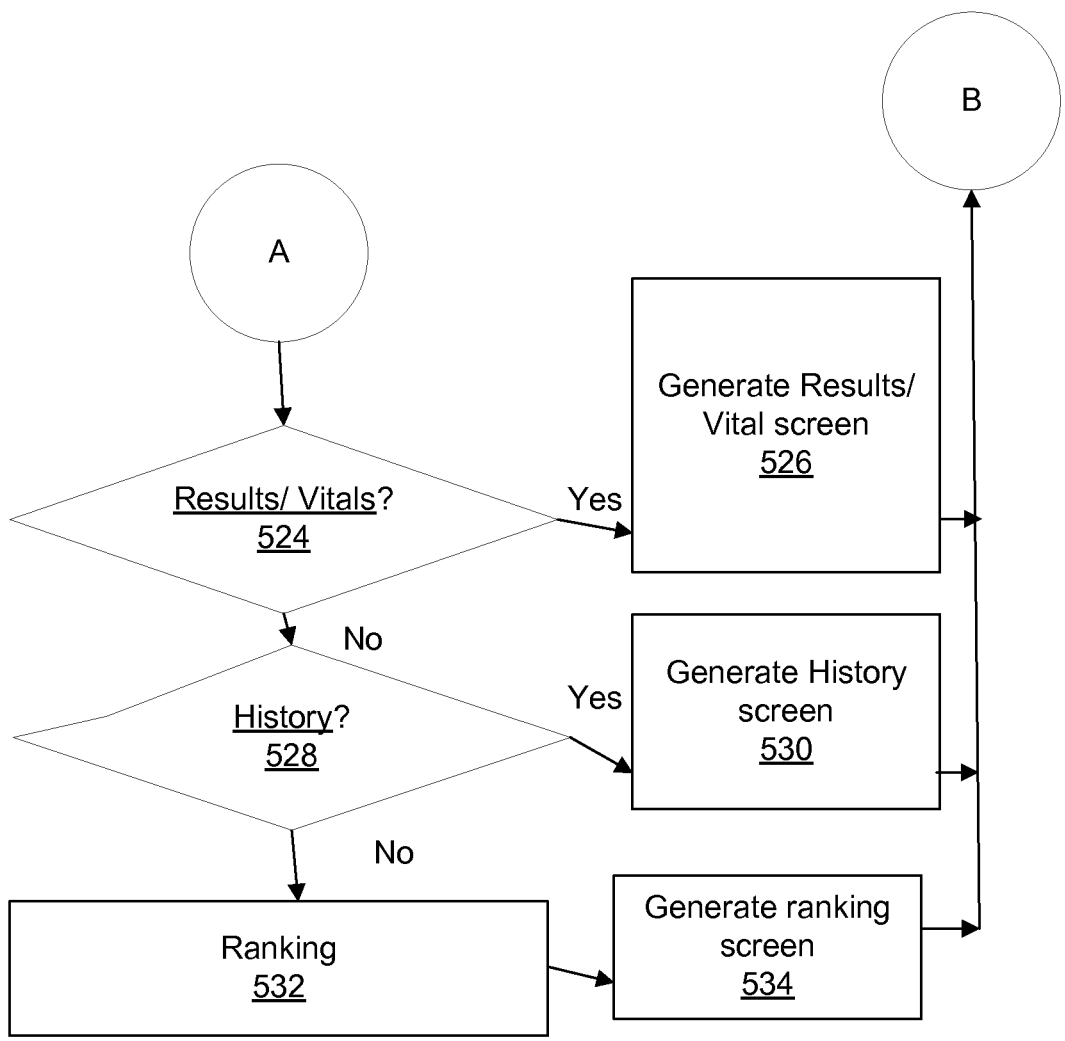

FIGS. 5a and 5b illustrate a process for health information processing system 202 for a patient 208. At 502, user application engine 320 generates a user interface, such as the screenshot 600 of FIG. 6, which is described below, for display on patient interface 226 for patient 208 to login. At 504, security engine 304 authenticates the patient, and if authenticated, user application engine 320 generates a user interface, such as the screenshot 700 of FIG. 7, which is described below, for display on patient interface 226 for patient 208 to select an action. In various embodiments, user application engine 320 directs patient 208 to a platform that is run by another system user 201 with which patient 208 has an affiliation. For example, patient 208 may have insurance coverage through a particular health maintenance organization. In this case, user application 320 directs patient 208 to a screenshot and platform that is for that health maintenance organization with data provided in part by that health maintenance organization and in part by health information processing system 202. This may be done between other system users 201, such as a physician 222 that is part of the health maintenance organization.

At 506, user application engine 320 receives a patent request from patient 208. If, at 508, the patient selects personal data, at 510, user application engine 320 performs the requested action and generates a user interface of patient personal data, such as the screenshot 800 of FIG. 8, which is described below, for display on patient interface 226 for patient 208 to select an action. User application engine 320 executes a patient request from the screenshot generated at 510 or returns to waiting to receive a patient request at 506.

If, at 512, the patient selects data sharing, at 514, user application engine 320 performs the requested action and generates a user interface of patient data sharing, such as the screenshot 900 of FIG. 9, which is described below, for display on patient interface 226 for patient 208 to select an action. User application engine 320 executes a patient request from the screenshot generated at 514 or returns to waiting to receive a patient request at 506.

If, at 516, the patient selects data device, at 518, user application engine 320 performs the requested action and generates a user interface of health data sources 127, such as the screenshot 1000 of FIG. 10, which is described below, for display on patient interface 226 for patient 208 to select an action. User application engine 320 executes a patient request from the screenshot generated at 518 or returns to waiting to receive a patient request at 506.

If, at 520, the patient selects health application, at 522, user application engine 320 performs the requested action and generates a user interface of health applications, such as the screenshot 1100 of FIG. 11, which is described below, for display on patient interface 226 for patient 208 to select an action. User application engine 320 executes a patient request from the screenshot generated at 522 or returns to waiting to receive a patient request at 506.

If, at 524, the patient selects results/vitals, at 526, user application engine 320 performs the requested action and generates a user interface for results/vitals of health applications, health data sources 227 or both, such as the screenshot 1200 of FIG. 12, which is described below, for display on patient interface 226 for patient 208 to select an action. User application engine 320 executes a patient request from the screenshot generated at 526 or returns to waiting to receive a patient request at 506.

If, at 528, the patient selects history, at 530, user application engine 320 performs the requested action and generates a user interface for purchase history, data share, review, or recommendations reviewed, such as the screenshot 1300 of FIG. 13, which is described below, for display on patient interface 226 for patient 208 to select an action. User application engine 320 executes a patient request from the screenshot generated at 530 or returns to waiting to receive a patient request at 506.

If, at 532, the patient selects ranking, at 534, user application engine 320 performs the requested action and generates a user interface for ranking providers 204, health data sources 227 or health applications, such as the screenshot 1400 of FIG. 14, which is described below, for display on patient interface 226 for patient 208 to select an action. User application engine 320 executes a patient request from the screenshot generated at 534 or returns to waiting to receive a patient request at 506.

Figure 6:
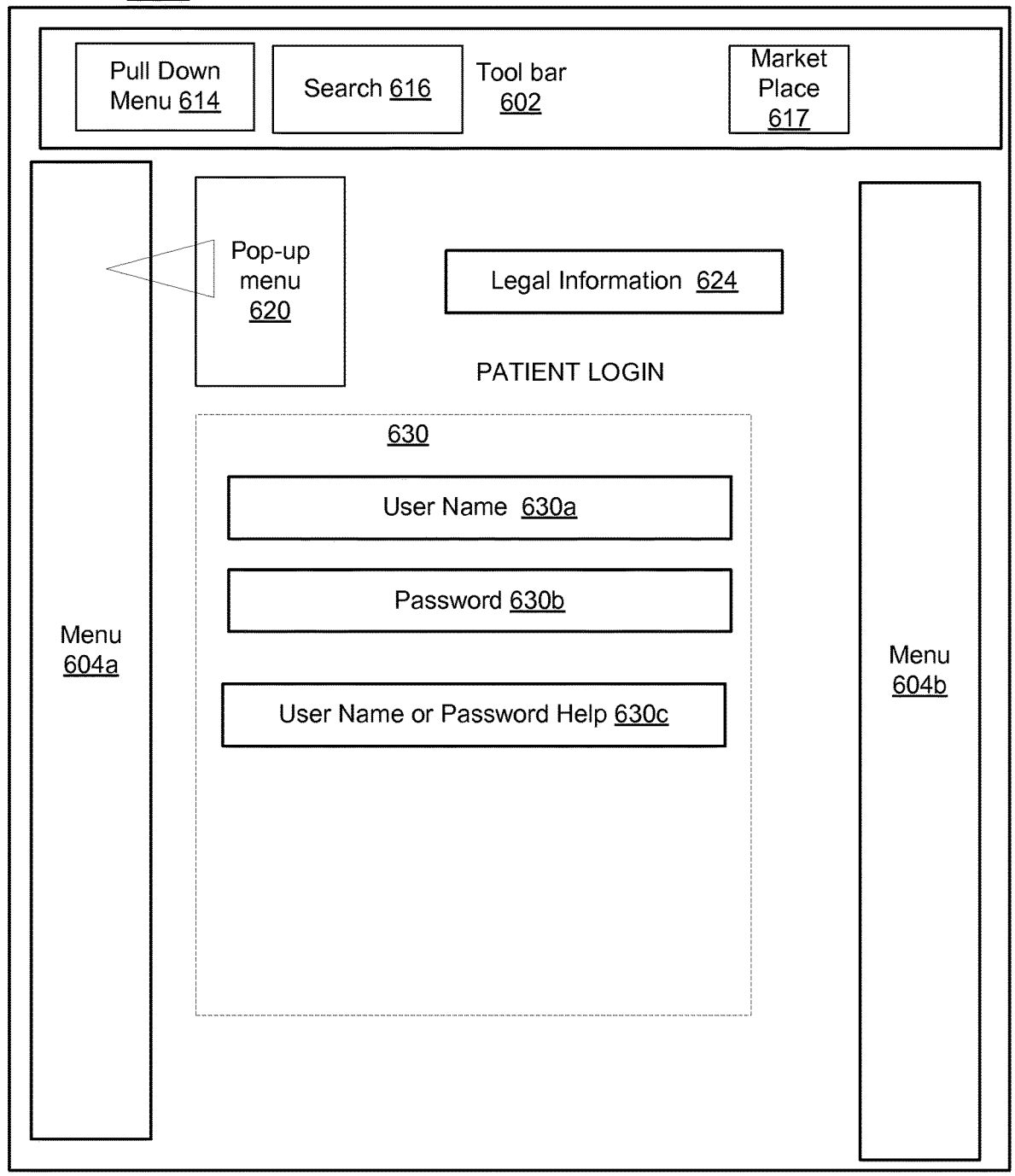
FIG. 6 illustrates a screenshot for patient login in the process of FIGS. 5a and 5b.

FIG. 6 illustrates a screenshot 600 for the login of patient 208. Screenshot 600 comprises a tool bar 602, a plurality of menus 604a and 604b, a legal information selection element 624, and a login menu 630. Toolbar 602 and menus 604 include a plurality of icons or links (not shown) for navigation, retrieving or changing information on the website, For simplicity, only two menus 604 are shown, but the screenshot may include any number of menus. A pop-up menu 620 is a menu that appears on screenshot 600 when an icon or link in menu 604 is selected. Tool bar 602, menus 604, legal information selection element 624, and login menu 630 may be located anywhere within the screenshot. In various embodiments, menu 604b includes advertisements. In some embodiments, menu 604b may be located along the right side or the bottom of the screenshot or both.

Tool bar 602 also includes a pull down menu 614 that may include the icons in tool bar 602, menus 604, legal information selection element 624, and login menu 630. Tool bar 602 also includes a search or instruction icon 616 for searching health information processing system 202 for user accessible information. Tool bar 602 further includes a marketplace icon 617 for navigating the user to a marketplace of health applications, health data sources 227, or information for providers 204, payers 206, or other system users 201 depending on the context of the current screenshot. Elements of tool bar 602 may be arranged anywhere within tool bar 602.

Legal information selection element 624 allows the user to navigate to a screen that displays legal agreements, legal disclaimers, user authorizations, privacy disclosures, and the like.

Login menu 630 comprises a user name selection element 630a and a password selection element 630b for patient 208 to enter a user name and password, respectively. Login menu 630 further comprises a user name or password help selection element 630c to assist patient 208 if patient 208 has forgotten the user name or password.

Figure 7:
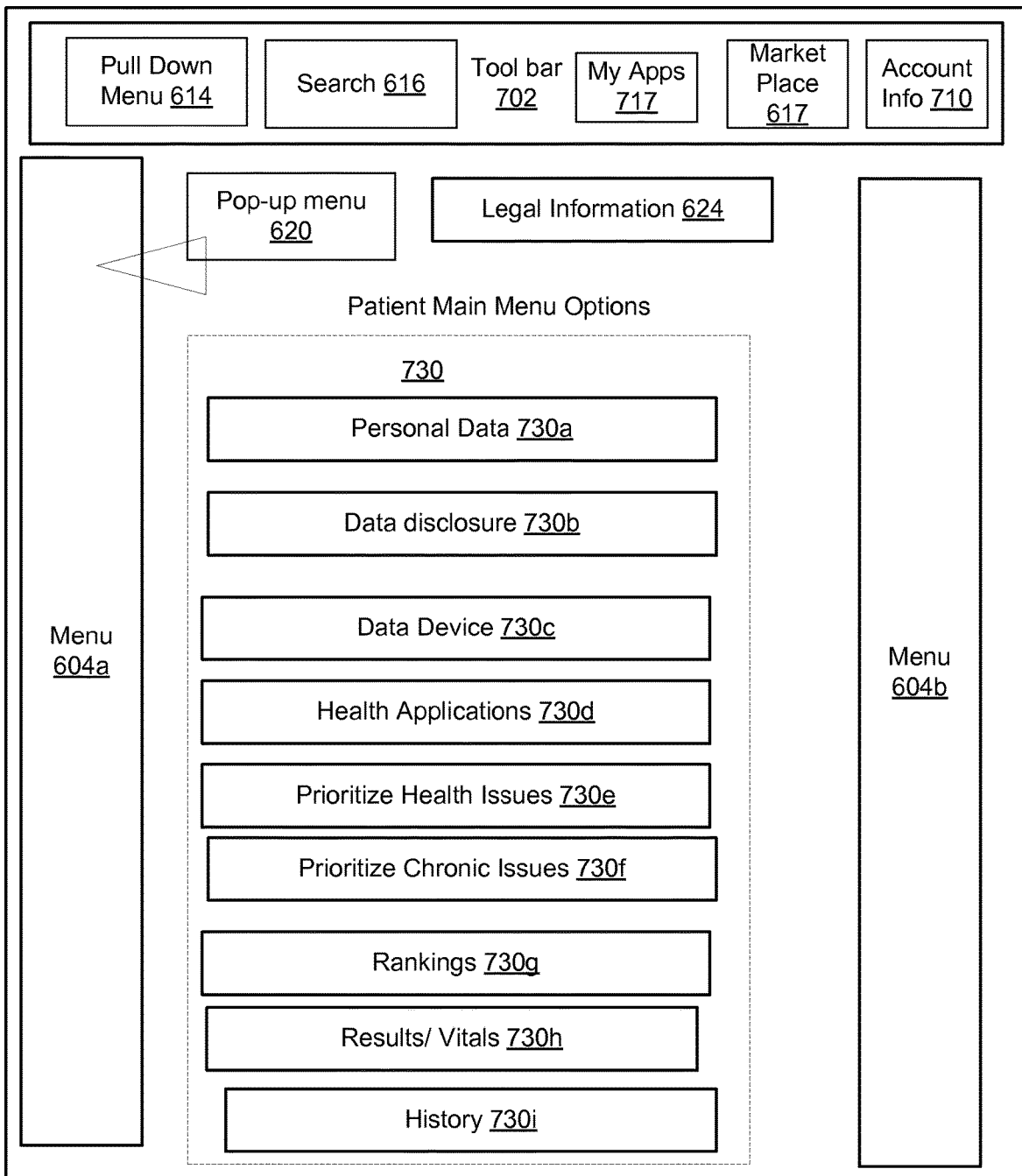
FIG. 7 illustrates a screenshot for patient main menu options in the process of FIGS. 5a and 5b.

FIG. 7 illustrates a screenshot 700 for patient main menu options in health information processing system 202 for patient 208. Screenshot 700 comprises a tool bar 702, a plurality of menus 604a and 604b, a legal information selection element 624, and an option menu 730. Tool bar 702 includes an account information icon 710 that allows the user to access account information, such as payment information, for the user. Toolbar 702 further includes pull down menu icon 614, search icon 616, and marketplace icon 617. Toolbar 702 also includes a "my applications icon" 717 that allows the user to access his apps/devices.

Option menu 730 comprises a personal data selection element 730a for the user to access, add, or modify personal data, such as personal information, medical history and conditions, pharmaceuticals that the patient is or was prescribed or over the counter medications, wellness, and financial information, such as credit card or bank information for payment for services from health information processing system 202. Selecting personal data selection element 730a is described below in conjunction with FIG. 8.

Option menu 730 comprises a data disclosure selection element 730b for patient 208 to access, add, or modify data disclosure authorizations, such as sharing or bundling selected information with payers, providers, or family, sharing information anonymously with health information processing system 202 for a global sharing of anonymous data with health information processing system 202, providers 204, health data source developer 212 or analytics developer 214. Data disclosure selection element 730b also allows patient 208 to view comments made by those with whom data is shared. Data disclosure may be selective, in that different system users 201 have access to different data. In some embodiments, health information processing system 202 provides a social media platform or access to a social media platform, such as Facebook, GooglePlus, or LinkedIn. Selecting data disclosure selection element 730b is described below in conjunction with FIG. 9. In some embodiments, health information processing system 202 allows patient 208 to toggle on or off data sharing.

Option menu 730 comprises a data device selection element 730c for the user to access, add, or modify information regarding health data source 227, such device selection, controlling timing of uploading of information, ranking, recommending a data device, or searching for new data devices. Health data sources 227 that are available to a patient 208 may be determined by provider 204, payer 206, or health information processing system 202 based on personal data, health, wellness, or other factors of patient 208. Selecting data device selection element 730c is described below in conjunction with FIG. 10.

Option menu 730 comprises a health application selection element 730d for the user to access, add, or modify information regarding health applications for health data source 227, such as selection of health data source 227 currently used by the user or recommended by physician 222, ranking, recommending a health application, or searching for new health applications devices. Selecting health application selection element 730d is described below in conjunction with FIG. 11.

Option menu 730 comprises a health issues prioritization selection element 730e for the user to access, add, or modify the user's priority of health issues, such as medical conditions, medications, health data sources 227, or health applications for health data source 227. In various embodiments, advertising engine 322 generates and displays advertisements on the web page of patient 208 based on the priority of health issues set by patient 208 using health issues prioritization selection element 730e.

Option menu 730 comprises a chronic health issues prioritization selection element 730f for the user to access, add, or modify the user's priority of chronic health issues, such as chronic medical conditions, chronic medications, chronic health data sources 227, or chronic health applications for chronic health data source 227. In various embodiments, advertising engine 322 generates and displays advertisements on the web page of patient 208 based on the chronic health issues set by patient 208 using chronic health issues prioritization selection element 730f.

Option menu 730 comprises a ranking selection element 730g for the user to access, add, or modify the user's ranking of data devices, health applications, and physicians, or review ranking history. Selecting ranking selection element 730g is described below in conjunction with FIG. 14.

Option menu 730 comprises a results/vitals selection element 730h for the user to access, add, or modify the user's health applications, health data sources 227 or both. Selecting results/vitals selection element 730h is described below in conjunction with FIG. 12.

Option menu 730 comprises a history selection element 730i for the user to access, add, or modify the user's purchase history, data share, review, or recommendations reviewed. Selecting history selection element 730i is described below in conjunction with FIG. 13.

Figure 8:
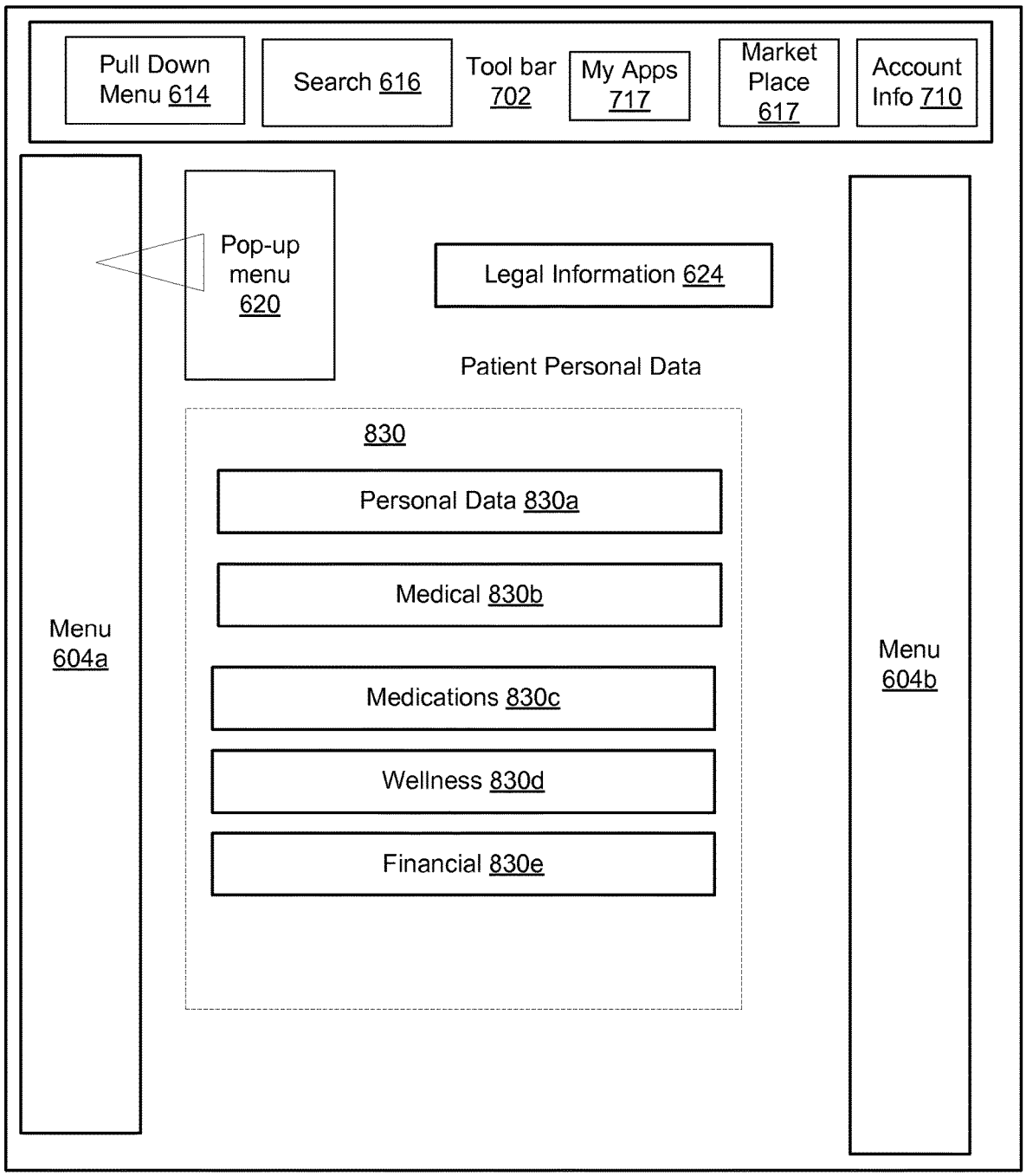
FIG. 8 illustrates a screenshot for a personal data options menu of the patient in the process of FIGS. 5a and 5b.

FIG. 8 illustrates a screenshot 800, which may be generated in response to selection of personal data selection element 730a (FIG. 7), for personal data menu options for patient 208. Screenshot 800 comprises a tool bar 702, a plurality of menus 604a and 604b, a legal information selection element 624, and a personal data menu 830.

Personal data menu 830 comprises a personal data selection element 830a for the user to access, add, or modify personal data. Personal data menu 830 comprises a medical data menu selection element 830b for patient 208 to access, add, or modify patient medical data, such as medical history, chronic conditions, and current health conditions. Personal data menu 830 comprises a medications selection element 830c for patient 208 to access, add, or modify pharmaceuticals that patient 208 is or was prescribed or over the counter medications that the patient is taking.

Personal data menu 830 comprises a wellness selection element 830d for patient 208 to access, add, or modify wellness data, such as the exercise regiment, diet, and stress reduction regiment of the user. Personal data menu 830 comprises a financial data selection element 830e for patient 208 to access, add, or modify financial information, such as credit card or bank information for payment for services from health information processing system 202.

Figure 9:
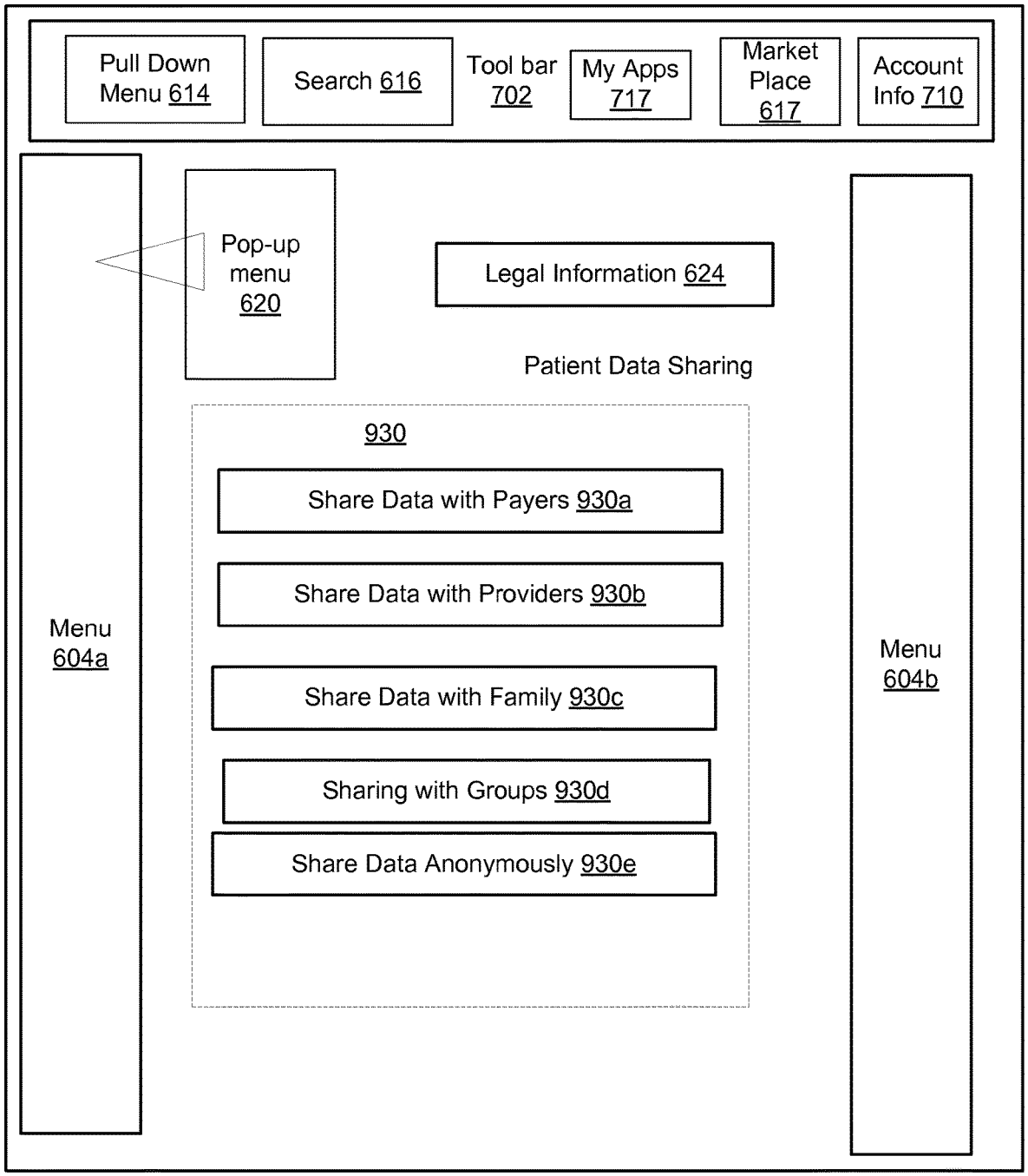
FIG. 9 illustrates a screenshot for data sharing menu of the patient in the process of FIGS. 5a and 5b.

FIG. 9 illustrates a screenshot 900 for patient data disclosure menu of patient 208, which may be generated in response to selection of data disclosure selection element 730b (FIG. 7). Screenshot 900 comprises a tool bar 702, a plurality of menus 604a and 604b, a legal information selection element 624, and a data disclosure menu 930.

Data disclosure menu 930 comprises a data sharing with payers 206 selection element 930a for patient 208 to access, add, or modify data disclosure authorizations for sharing selected information or bundles of information with payers 206. Data disclosure menu 930 comprises a data sharing with providers 204 selection element 930b for patient 208 to access, add, or modify data disclosure authorizations for sharing selected information with providers 204. Patient 208 may share with a specific physician 222, a medical provider network, a network of physicians 222, nurses and staff associated with the providers 204, or other providers 204 referred to or consulted by a specific provider 204 (e.g., the physician of patient 208). Data disclosure menu 930 comprises a data sharing or bundle sharing with family selection element 930c for patient 208 to access, add, or modify data disclosure authorizations for sharing selected information or bundles with family, friends, caregivers, conservators, lawyers, or social workers. Data disclosure menu 930 comprises a "sharing with groups" selection element 930d to allow patient 208 to share data or bundles with groups. The groups may be, for example, groups that share a common disease, such as diabetes, a common fitness goal, use the same or similar health data device 227, use the same or similar health application, common attributes, such as age, or the like. Data disclosure menu 930 comprises a data sharing with share anonymous data selection element 930e for patient 208 to access, add, or modify data disclosure authorizations for patient personal and medical data to be shared anonymously by health information processing system 202 with selected system users 201. In various embodiments, health information processing system 202 provides shared data automatically, either scheduled, periodically, or in real-time, to those with whom it is being shared via, for example, email, text, or websites.

Figure 10:
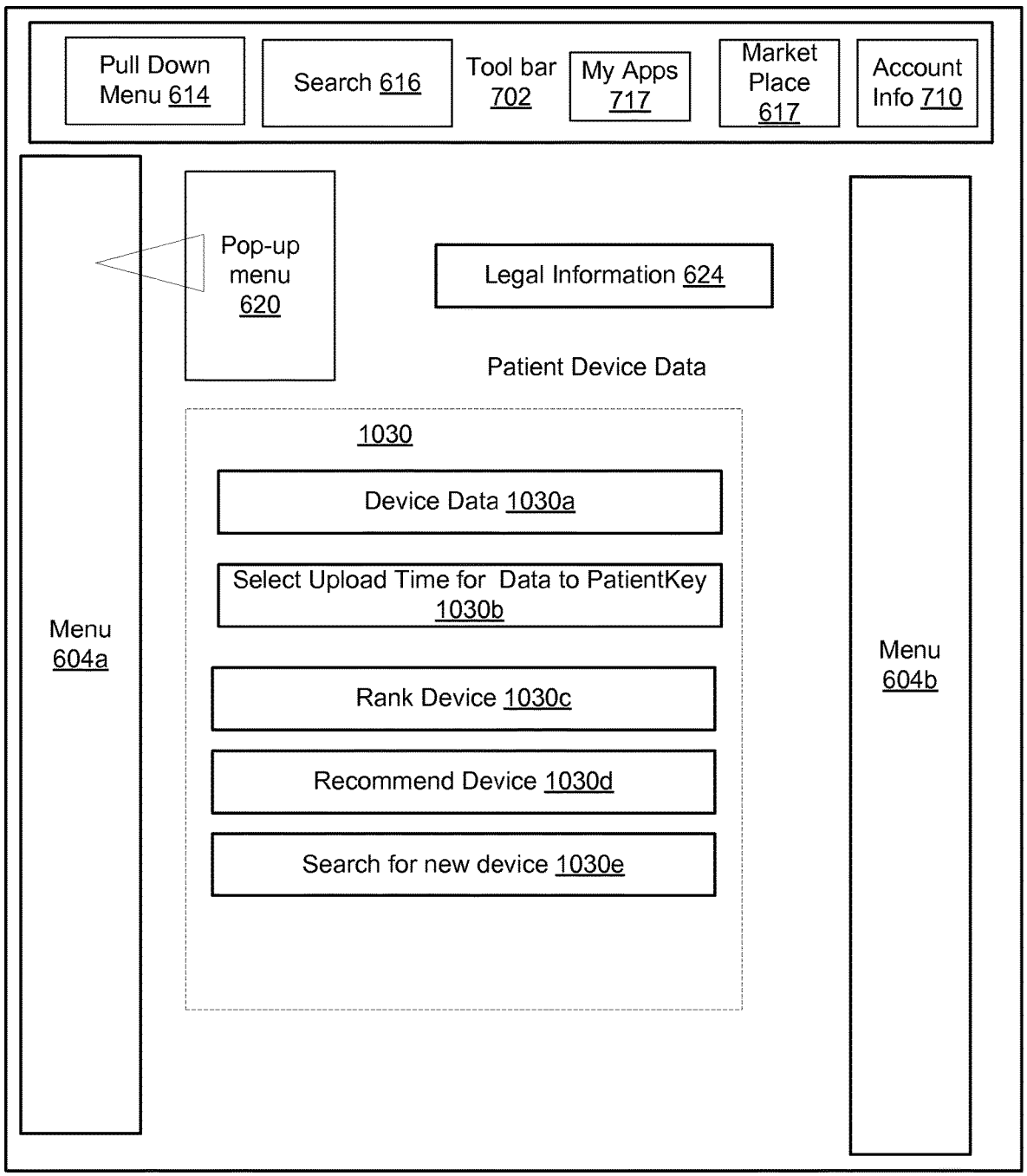
FIG. 10 illustrates a screenshot for a device data menu of the patient in the process of FIGS. 5a and 5b.

FIG. 10 illustrates a screenshot 1000, which may be generated in response to selection of data device selection element 730c (FIG. 7), for a device data menu of patient 208 in the process of FIGS. 5a and 5b. Screenshot 1000 comprises a tool bar 702, a plurality of menus 604a and 604b, a legal information selection element 624, and a patient device menu 1030.

Patient device menu 1030 comprises a device data selection element 1030a, a device data upload selection element 1030b, a rank device selection element 1030c, a recommend data device selection element 1030d, and a data device search selection element 1030e. Device data selection element 1030a allows patient 208 to access, add, or modify information regarding health data source 227 that patient 208 currently uses or have been prescribed by provider 204. Device data upload selection element 1030b allows patient 208 to access, add, or modify information regarding controlling timing of uploading of information of health data sources 227. In some embodiments, patient 208 may allow provider 204 to control the uploading of information. In some embodiments, health information processing system 202 or provider 204 control uploading of information. Rank device selection element 1030c allows patient 208 to access, add, or modify information regarding rankings of health data sources 227. Recommend data device selection element 1030d allows patient 208 to access, add, or modify information regarding recommending a health data source 227. Data device search selection element 1030e allows patient 208 to access, add, or modify information regarding searching for new data devices. In response to the data device search selection element 1030e, user application engine 120 displays a screenshot of available health data sources 227, or a screenshot of a specific health data source 227, such as the screenshot of FIG. 49, which are described below.

Figure 11:
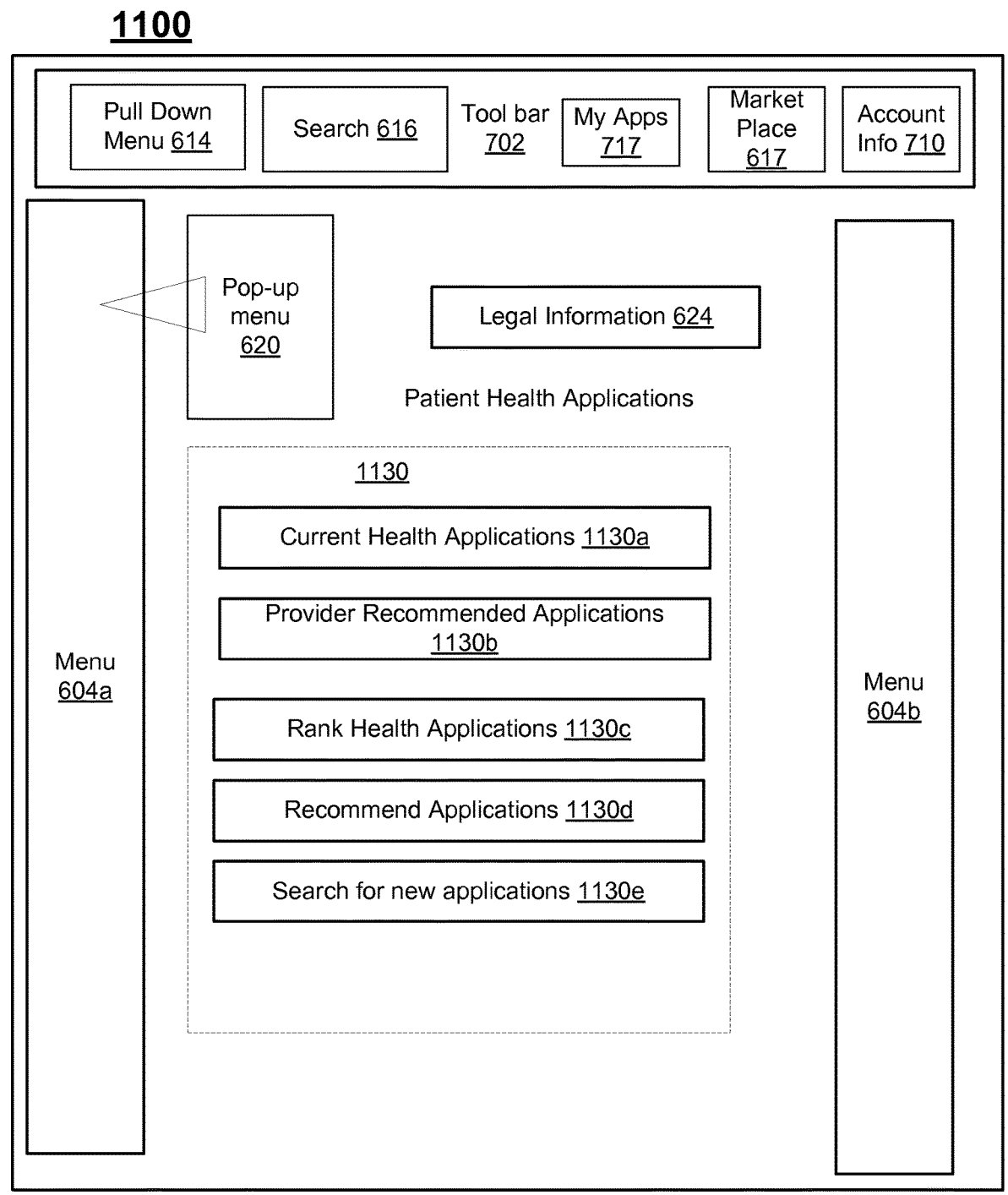
FIG. 11 illustrates a screenshot for a health applications menu of the patient in the process of FIGS. 5a and 5b.

FIG. 11 illustrates a screenshot 1100, which may be generated in response to selection of health application selection element 730d (FIG. 7), for a health applications menu of the patient in the process of FIGS. 5a and 5b. Screenshot 1100 comprises a tool bar 702, a plurality of menus 604a and 604b, a legal information selection element 624, and a patient health applications menu 1130.

Patient health applications menu 1130 comprises a current health applications selection element 1130a, a provider recommended health applications selection element 1130b, a rank health applications selection element 1130c, a recommend health applications selection element 1130d, and a search health applications selection element 1130e. Current health applications selection element 1130a allows patient 208 to access, add, or modify information of health applications currently used by patient 208. Provider recommended health applications selection element 1130b allows patient 208 to access, add, or modify information related to health applications recommended by a provider 204 of patient 208. Rank health applications selection element 1130c allows patient 208 to access, add, or modify information for ranking health applications used by patient 208. The rankings are described in conjunction with FIGS. 39-42. Recommend health applications selection element 1130d allows patient 208 to access, add, or modify information for recommending for health applications. Search health applications selection element 1130e allows patient 208 to access, add, or modify information for searching for or perusing new health applications, and adding selected health applications to patient system 208. In response to the selection of search health applications selection element 1130e, user application engine 120 displays a screenshot of available health applications, such as the screenshot of FIG. 47, which is described below.

Figure 12:
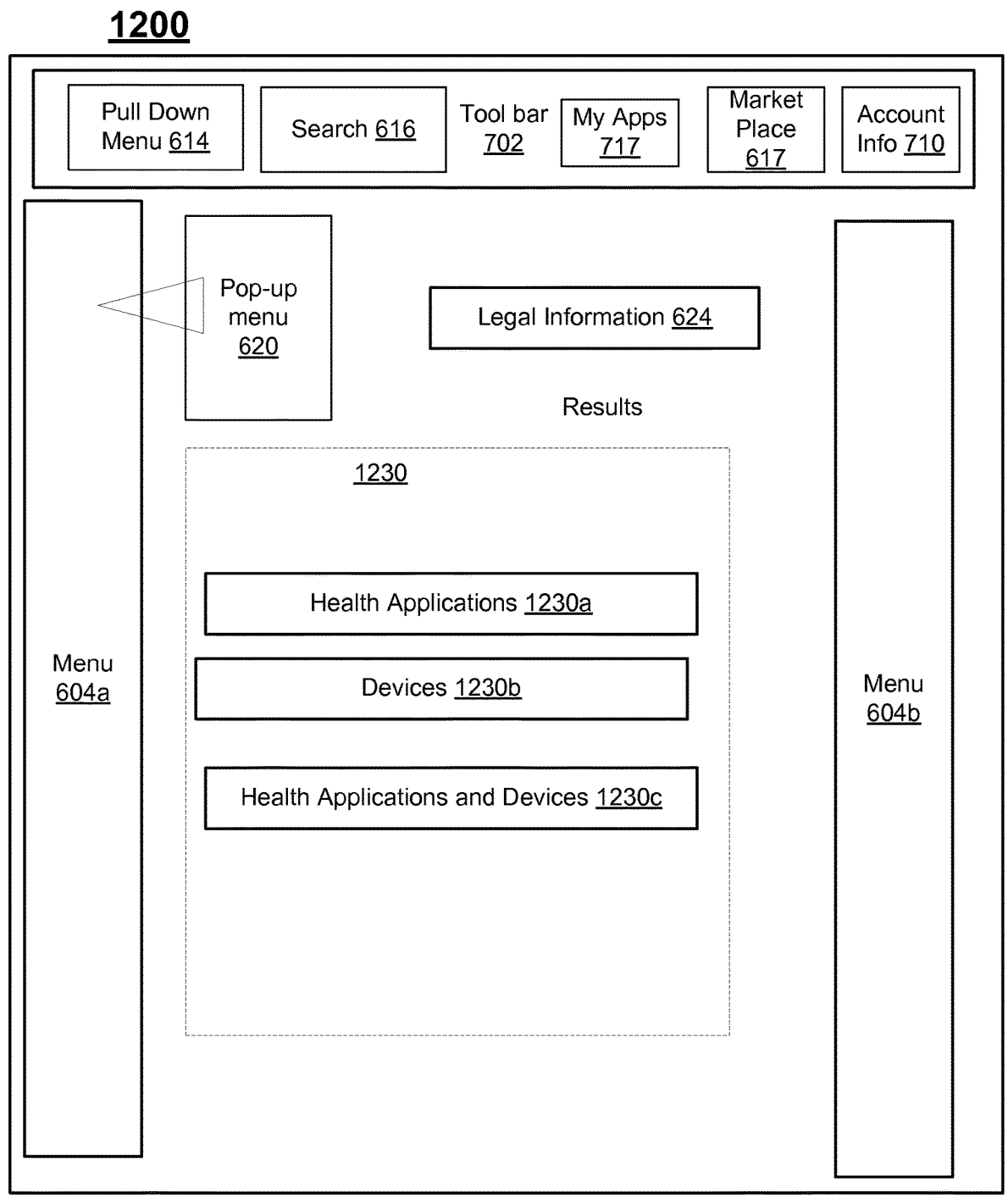
FIG. 12 illustrates a screenshot for a results/vitals menu of the patient in the process of FIGS. 5a and 5b.

FIG. 12 illustrates a screenshot 1200, which may be generated in response to selection of results/vitals selection element 730h (FIG. 7), for a results/vitals menu of the patient in the process of FIGS. 5a and 5b. Screenshot 1200 comprises a tool bar 702, a plurality of menus 604a and 604b, a legal information selection element 624, and a results/vitals menu 1230.

Results/vitals menu 1230 comprises a health applications selection element 1230a, a health data sources selection element 1230b, and a health applications and health data sources selection element 1230c to allow patient 208 to access, add, or modify information related to health applications, health data sources 227, and health applications, or both.

Figure 13:
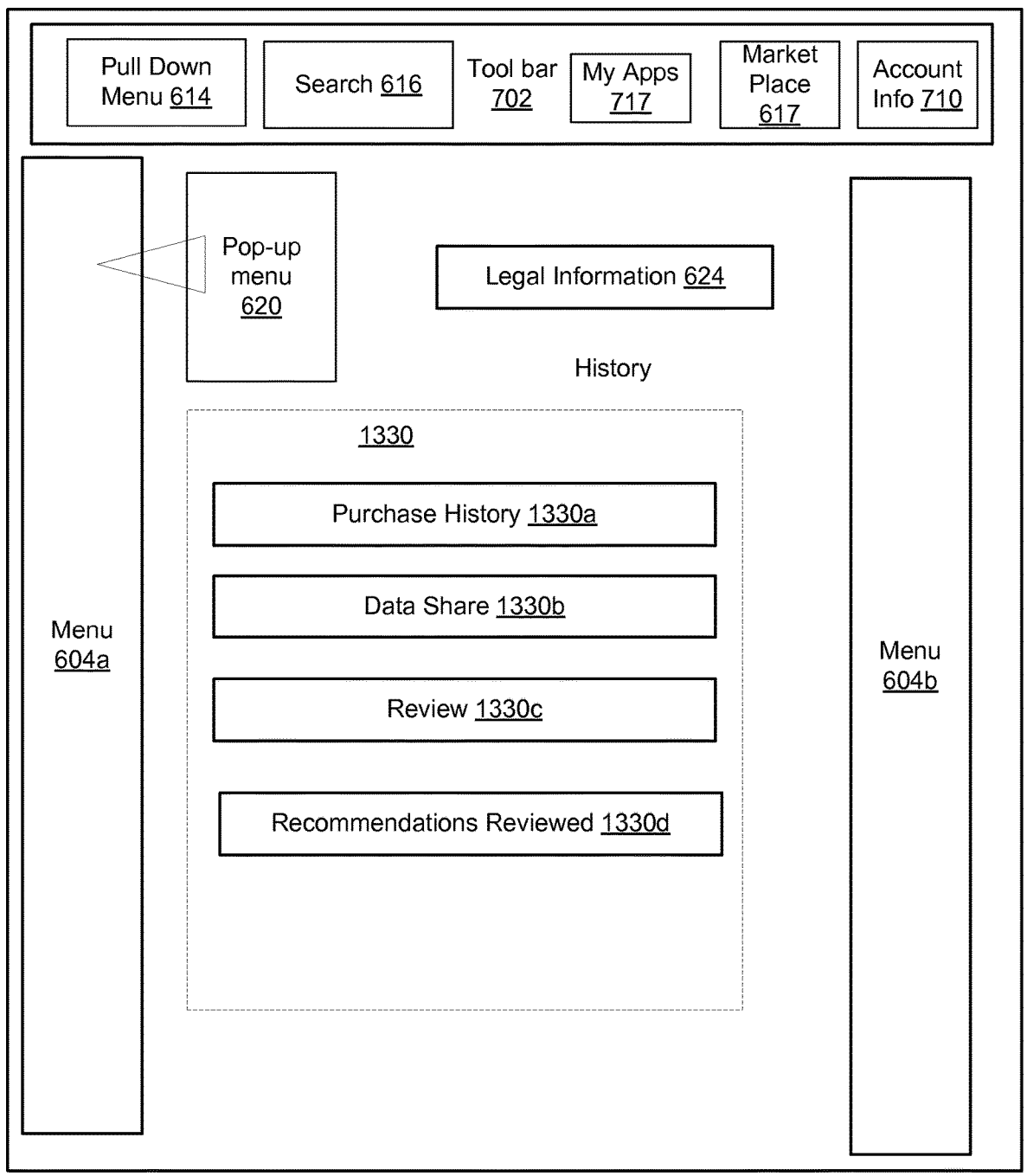
FIG. 13 illustrates a screenshot for a history menu of the patient in the process of FIGS. 5a and 5b.

FIG. 13 illustrates a screenshot 1300, which may be generated in response to selection of history selection element 730i (FIG. 7), for a history menu of the patient in the process of FIGS. 5a and 5b. Screenshot 1300 comprises a tool bar 702, a plurality of menus 604a and 604b, a legal information selection element 624, and a history menu 1330.

History menu 1330 comprises a purchase history selection element 1330a, a data share selection element 1330b, a priority history review selection element 1330c, and a recommendations reviewed selection element 1330d to allow patient 208 to access, add, or modify information related to priority of purchase history, data share, review, or recommendations reviewed.

Figure 14:
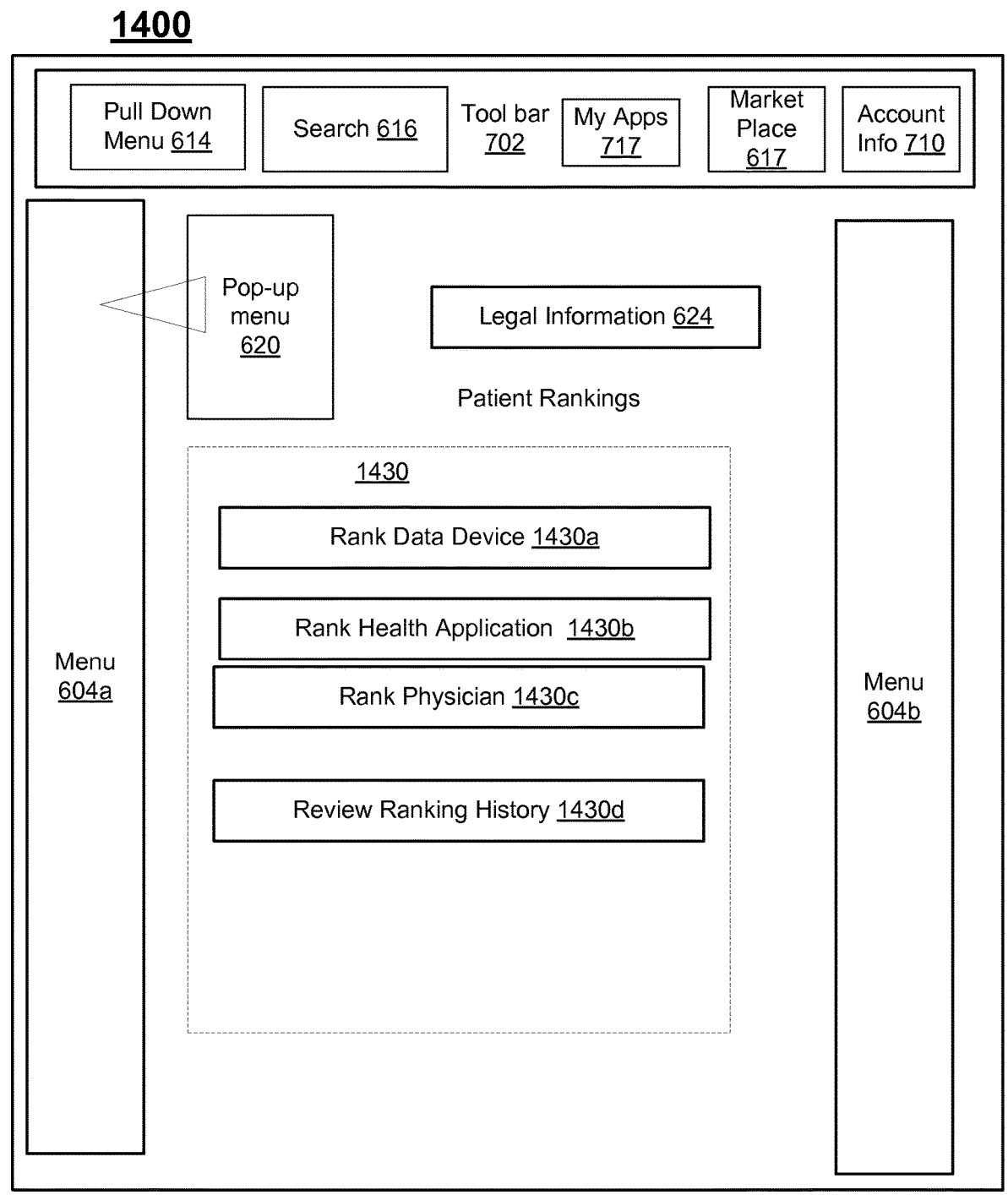
FIG. 14 illustrates a screenshot for a ranking menu of the patient in the process of FIGS. 5a and 5b.

FIG. 14 illustrates a screenshot 1400, which may be generated in response to selection of ranking selection element 730g (FIG. 7), for a ranking menu of the patient in the process of FIGS. 5a and 5b. Screenshot 1400 comprises a tool bar 602, a plurality of menus 604a and 604b, a legal information selection element 624, and a patient rankings menu 1430.

Patient rankings menu 1430 comprises a rank data device selection element 1430a, a rank health application selection element 1430b, and a rank physician selection element 1430c to allow patient 208 to access, add, or modify information related to rankings of health data sources 227, health applications, and physicians 222 (or other providers 204), respectively. Patient rankings menu 1430 further comprises a review ranking history selection element 1430d to allow patient 208 to access, add, or modify information related to the history of rankings by patient 208. Rankings are described in conjunction with FIGS. 39-46.

Figure 15A:
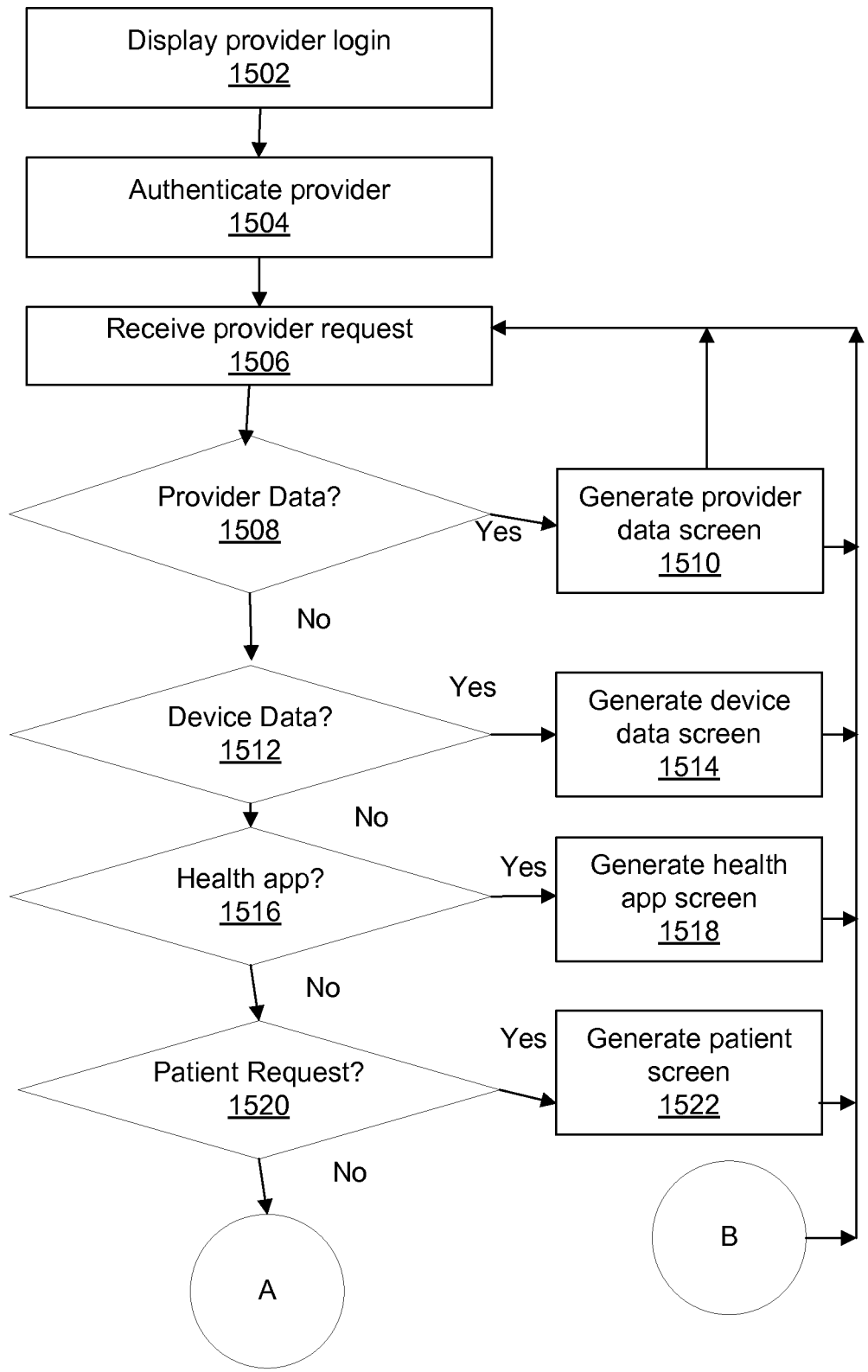
FIGS. 15a and 15b illustrate a process for a provider of the health data processing system of FIG. 2.
Figure 15B:
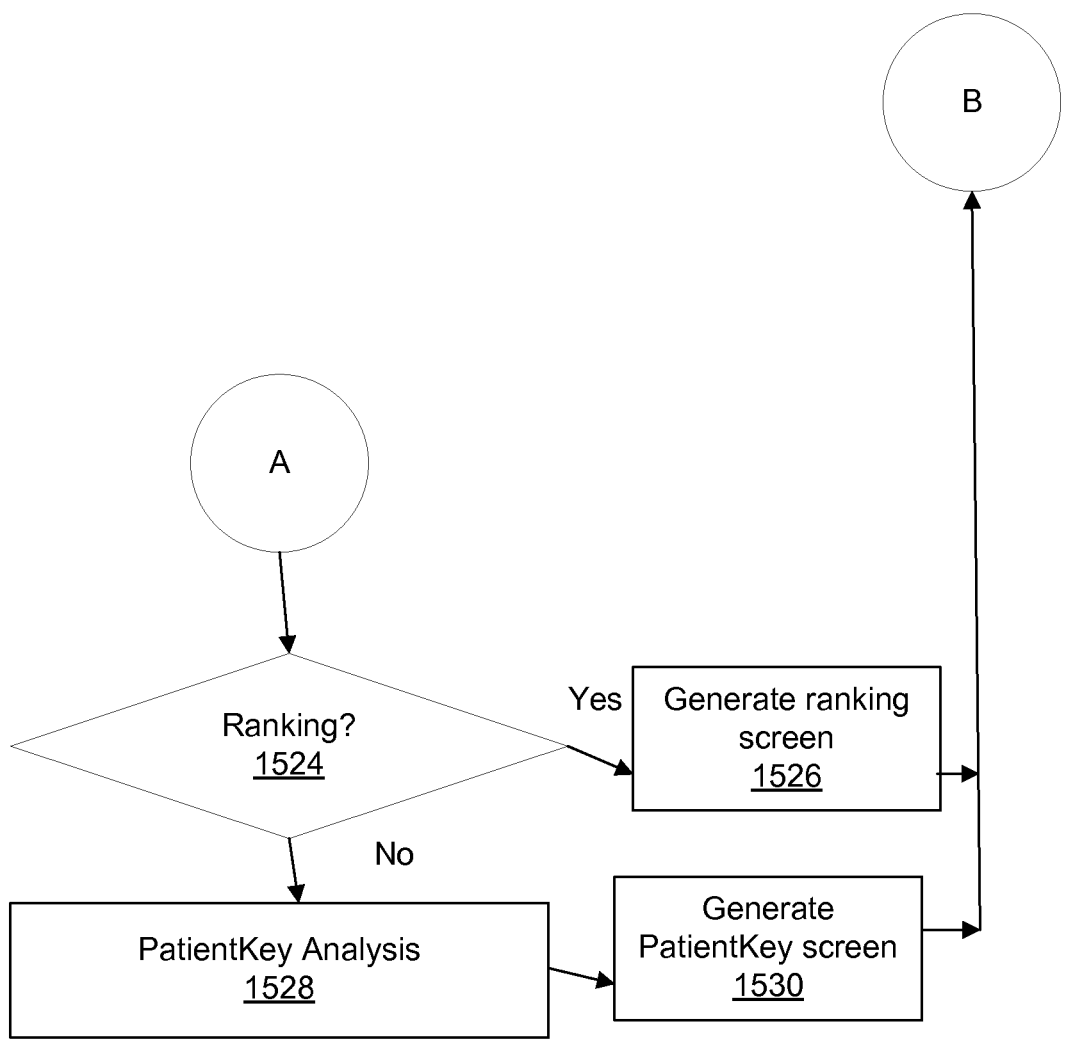

FIGS. 15a and 15b illustrate a process for health information processing system 202 for a provider 204. At 1502, user application engine 320 generates a user interface, such as the screenshot 1600 of FIG. 16, which is described below, for display on an interface of provider 204 for provider 204 to login. At 1504, security engine 304 authenticates provider 204, and if authenticated, user application engine 320 generates a user interface, such as the screenshot 1700 of FIG. 17, which is described below, for display for provider 204 to select an action.

At 1506, user application engine 320 receives a request from provider 204. If, at 1508, provider 204 selects provider data, at 1510, user application engine 320 performs the requested action and generates a user interface of provider data, such as the screenshot 1800 of FIG. 18, which is described below, for display on an interface of provider 204 for provider 204 to select an action. User application engine 320 executes a provider 204 request from the screenshot generated at 1510 or returns to waiting to receive a provider 204 request at 1506.

If, at 1512, provider 204 selects device data, at 1514, user application engine 320 performs the requested action and generates a user interface of health data sources 227, such as the screenshot 1900 of FIG. 19, which is described below, for display on an interface of provider 204 for provider 204 to select an action. User application engine 320 executes a provider 204 request from the screenshot generated at 1514 or returns to waiting to receive a provider 204 request at 1506.

If, at 1516, provider 204 selects health application, at 1518, user application engine 320 performs the requested action and generates a user interface of health applications, such as the screenshot 2000 of FIG. 20, which is described below, for display on an interface of provider 204 for provider 204 to select an action. User application engine 320 executes a provider 204 request from the screenshot generated at 1518 or returns to waiting to receive a provider 204 request at 1506.

If, at 1520, provider 204 selects patient, at 1522, user application engine 320 performs the requested action and generates a user interface of patient data, such as the screenshot 2100 of FIG. 21, which is described below, for display on an interface of provider 204 for provider 204 to select an action. User application engine 320 executes a provider 204 request from the screenshot generated at 1522 or returns to waiting to receive a provider 204 request at 1506.

If, at 1524, provider 204 selects ranking, at 1526, user application engine 320 performs the requested action and generates a user interface for ranking, such as the screenshot 2200 of FIG. 22, which is described below, for display on an interface of provider 204 for provider 204 to select an action. User application engine 320 executes a provider 204 request from the screenshot generated at 1526 or returns to waiting to receive a provider 204 request at 1506.

If, at 1528, provider 204 selects access to health information processing system 202, at 1530, user application engine 320 performs the requested action and generates a user interface for access to health information processing system 202, such as the screenshot 2300 of FIG. 23, which is described below, for display on an interface of provider 204 for provider 204 to select an action. User application engine 320 executes a provider 204 request from the screenshot generated at 1530 or returns to waiting to receive a provider 204 request at 1506.

Figure 16:
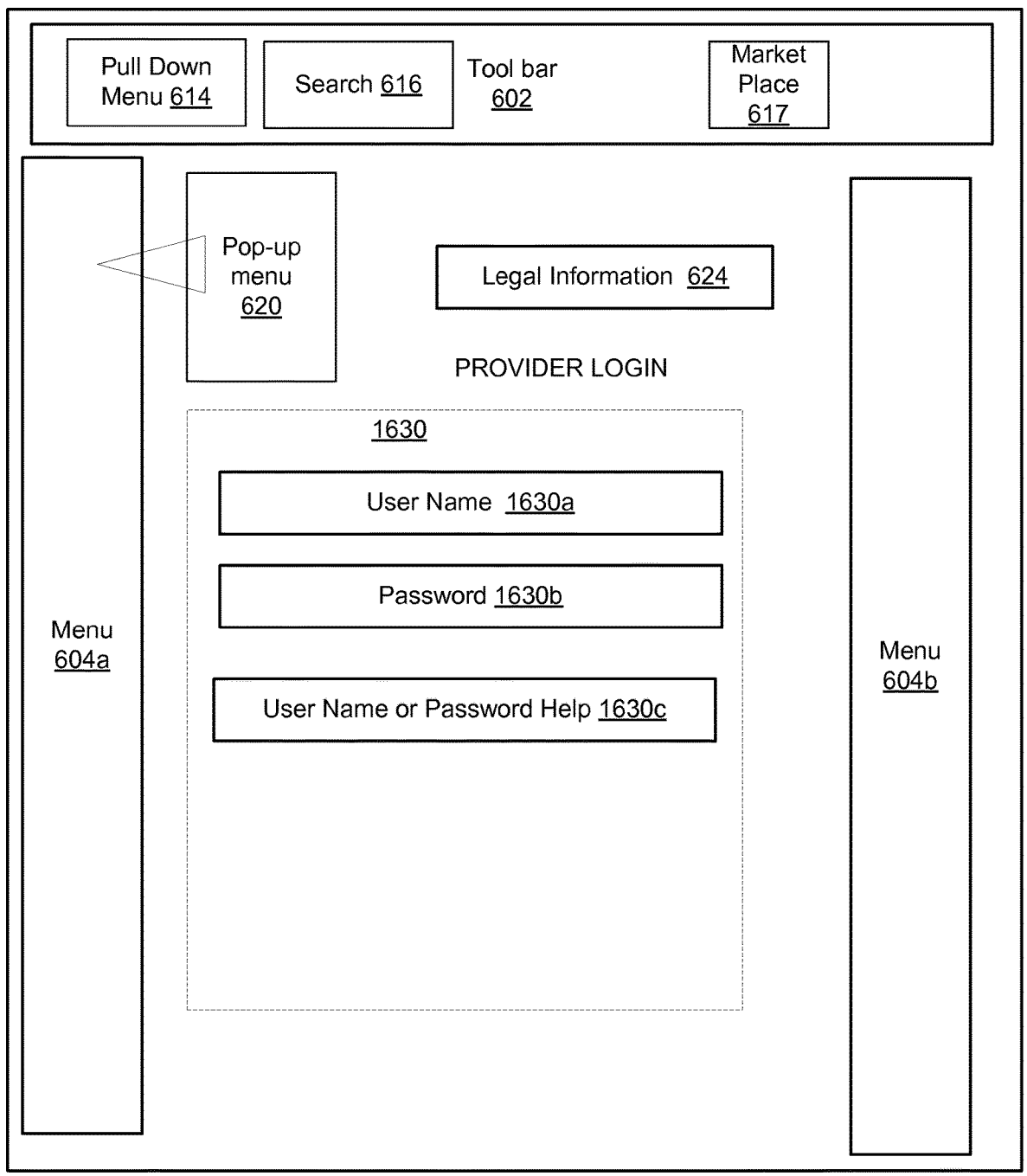
FIG. 16 illustrates a screenshot for provider login in the process of FIGS. 15a and 15b.

FIG. 16 illustrates a screenshot 1600 for the login of provider 204 in the process of FIGS. 15a and 15b. Screenshot 1600 comprises a tool bar 602, a plurality of menus 604a and 604b, a legal information selection element 624, and a login menu 1630.

Login menu 1630 comprises a user name selection element 1630a and a password selection element 1630b for provider 204 to enter a user name and password, respectively. Login menu 1630 further comprises a user name or password help selection element 1630c to assist provider 204 if provider 204 has forgotten the user name or password.

Figure 17:
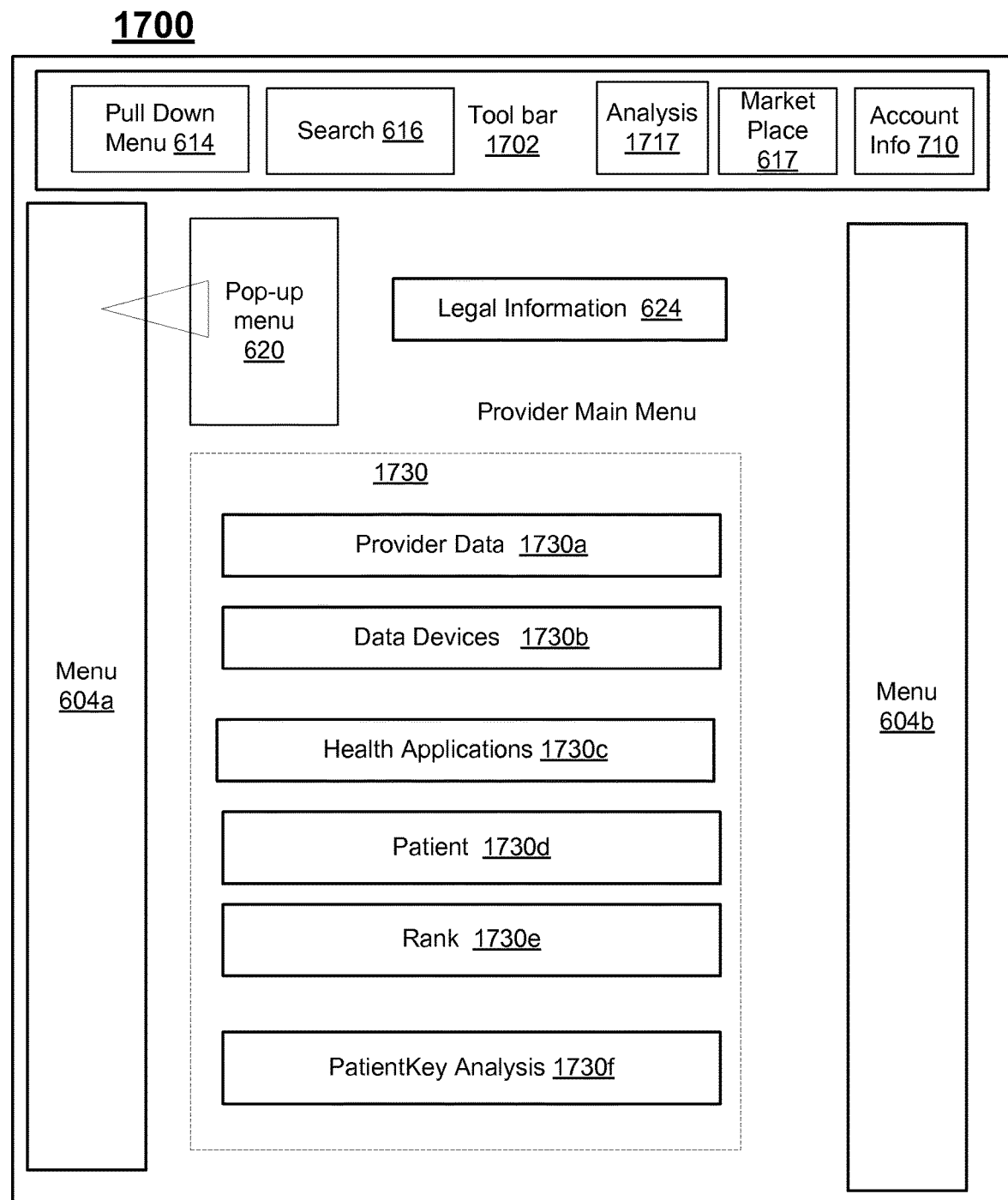
FIG. 17 illustrates a screenshot for provider main menu options in the process of FIGS. 15a and 15b.

FIG. 17 illustrates a screenshot 1700 for provider main menu options in health information processing system 202 for provider 204 in the process of FIGS. 15a and 15b. Screenshot 1700 comprises a tool bar 1702, a plurality of menus 604a and 604b, a legal information selection element 624, and a provider option menu 1730. Toolbar 702 includes pull down menu icon 614, search icon 616, marketplace icon 617, and account information icon 1710. Toolbar 702 also includes an analysis icon 1717 that allows provider to access analysis by health information processing system 202. In various embodiments, selection of analysis icon 1717 navigates directly to the screenshot of FIG. 23. In various embodiments, selection of analysis icon 1717 navigates directly to the screenshot of FIG. 56.

Provider option menu 1730 comprises a provider data selection element 1730a, a data device selection element 1730b, a health applications selection element 1730c, a patient selection element 1730d, a rank selection element 1730e, and a health information processing system 202 selection element 1730f. Provider data selection element 1730a allows provider 204 to access, add, or modify information related to provider 204, composite data of patients, and set up or change account information or features of health information processing system 202. Selecting provider data selection element 1730a is described below in conjunction with FIG. 18.

Data device selection element 1730b allows provider 204 to access, add, or modify information regarding health data sources 227, such as device data, device selection, or device rankings, searching for new data devices, analysis of health data sources 227 by health information processing system 202. Selecting data device selection element 1730b is described below in conjunction with FIG. 19.

Health applications selection element 1730c allows provider 204 to access, add, or modify information regarding health applications, such as health application selection, health application rankings, searching for new heath applications, analysis of health applications by health information processing system 202. Selecting health applications selection element 1730c is described below in conjunction with FIG. 20.

Patient selection element 1730d allows provider 204 to access, add, or modify information related to a patient 208, such as patient data or health data sources used by patient 208, information related to prescribing health data sources 227 or health applications to the patient or prescribe using groups of patients, or analysis of patient data, devices or health applications by health information processing system 202. Selecting patient selection element 1730d is described below in conjunction with FIG. 21.

Rank selection element 1730e allows provider 204 to access, add, or modify the ranking of health data sources 227, health applications, medications, treatments, or review ranking history. Selecting rank selection element 1730e is described below in conjunction with FIG. 22.

Health information processing system 202 selection element 1730f allows provider 204 to access, add, or modify the data on health information processing system 202. Selecting health information processing system 202 selection element 1730f is described below in conjunction with FIG. 23.

Figure 18:
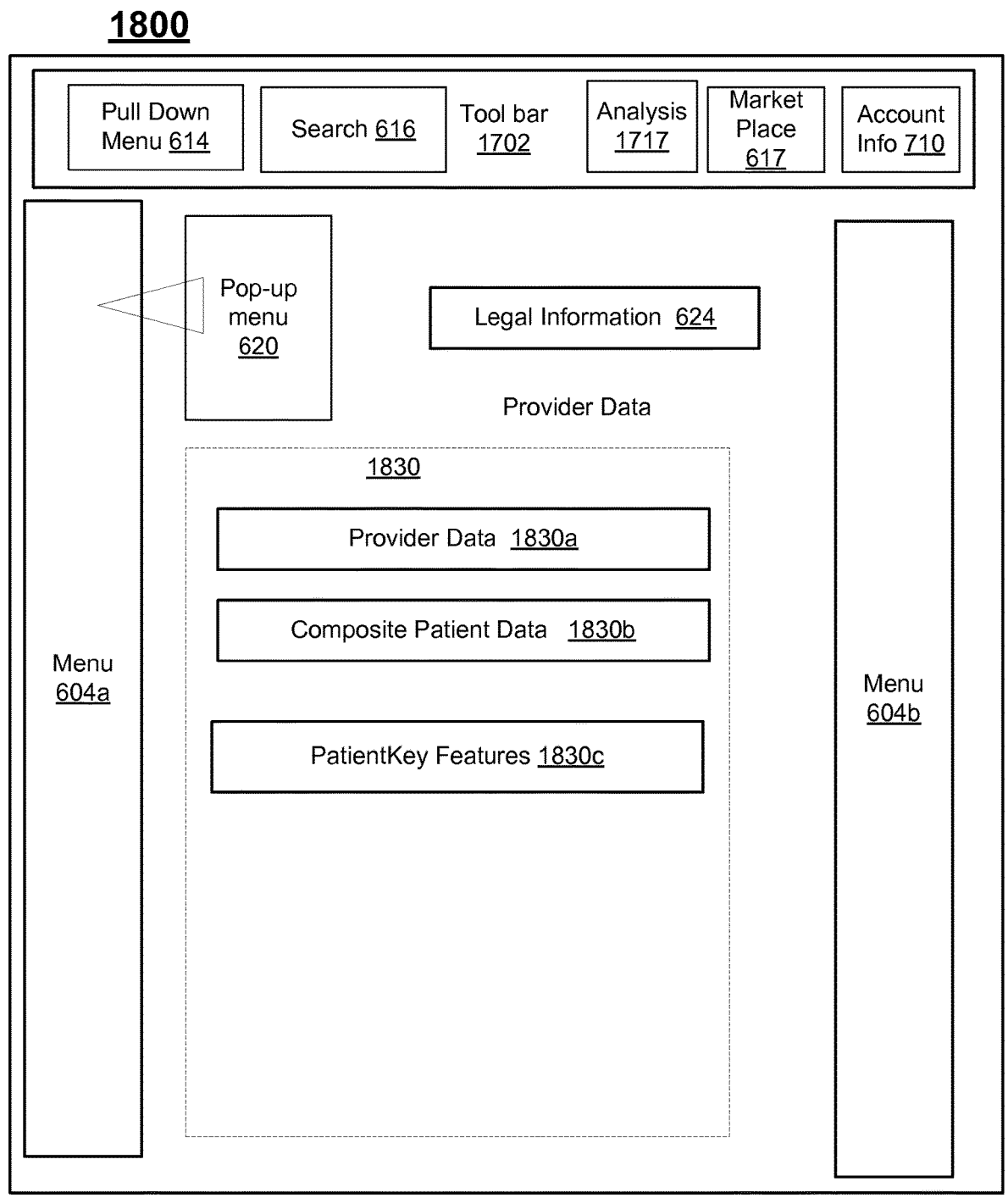
FIG. 18 illustrates a screenshot for provider data in the process of FIGS. 15a and 15b.

FIG. 18 illustrates a screenshot 1800, which may be generated in response to selection of provider data selection element 1730a (FIG. 17), for provider data in the process of FIGS. 15a and 15b. Screenshot 1800 comprises a tool bar 1702, a plurality of menus 604a and 604b, a legal information selection element 624, and a provider data menu 1830.

Provider data menu 1830 comprises a provider selection element 1830a, a composite patient data selection element 1830b, and a health information processing system selection element 1830c. Provider selection element 1830a allows provider 204 to access, add, or modify information related to provider 204. Composite patient data selection element 1830b allows provider 204 to access, add, or modify information related to composite data of patients. Health information processing system selection element 1830*c* allows provider 204 to access, add, or modify information related to account information or features of health information processing system 202. The features may include, for example, triggers for patient alerts, such as patient blood pressure. The alerts may be shown in the alerts list 5636 (FIG. 56) described below.

Figure 19:
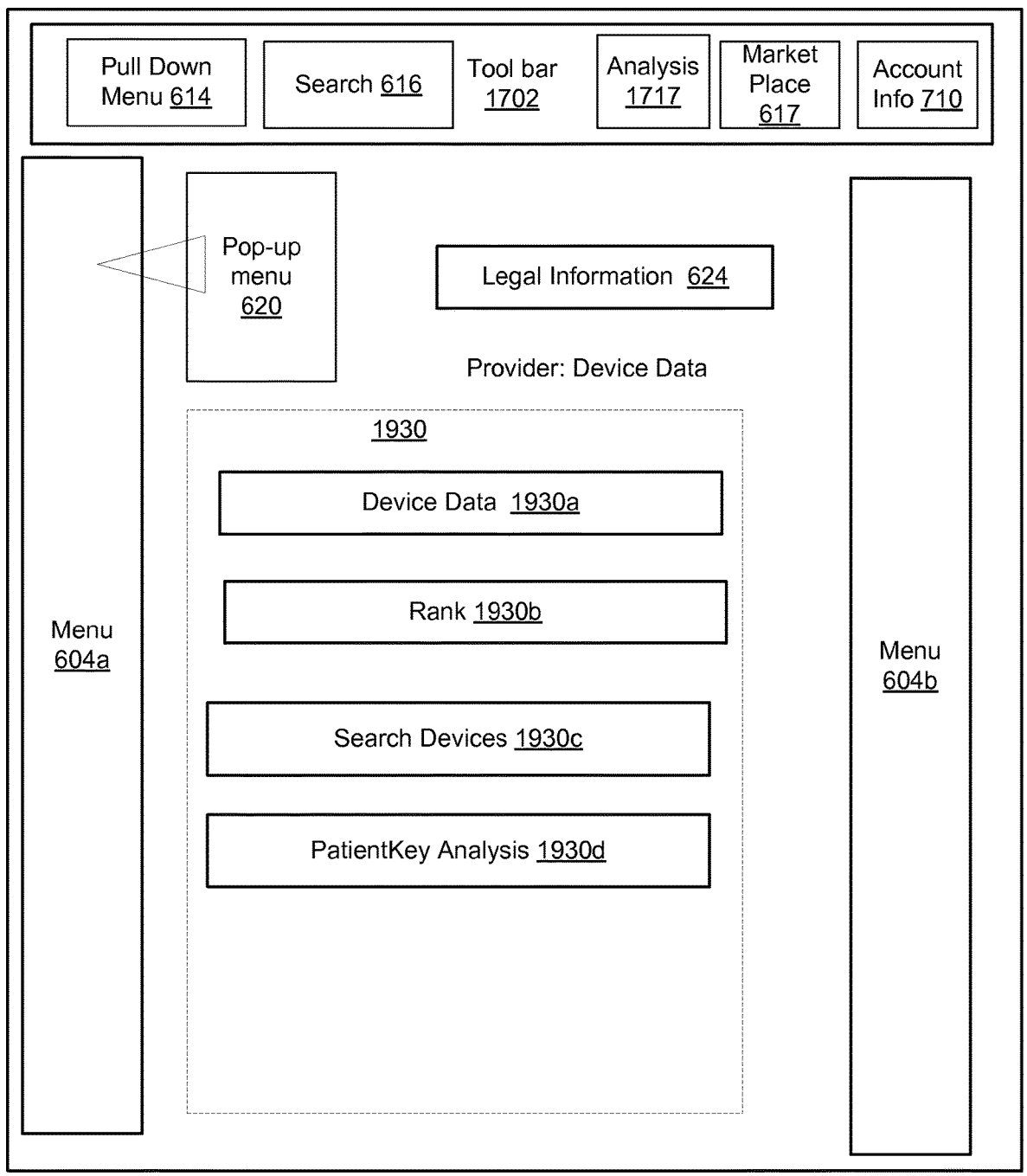
FIG. 19 illustrates a screenshot for device data accessible by a provider in the process of FIGS. 15a and 15b.

FIG. 19 illustrates a screenshot 1900, which may be generated in response to selection of data device selection element 1730*b* (FIG. 17), for device data accessible by provider 204 in the process of FIGS. 15*a* and 15*b*. Screenshot 1900 comprises a tool bar 1702, a plurality of menus 604*a* and 604*b*, a legal information selection element 624, and a device data menu 1930.

Device data menu 1930 comprises a device data selection element 1930*a*, a ranking selection element 1930*b*, a search devices selection element 1930*c*, and a health information processing system 202 selection element 1930*d*. Device data selection element 1930*a* allows provider 204 to access, add, or modify information related to health data sources 227. Ranking selection element 1930*b* allows provider 204 to access, add, or modify information related to ranking health data sources 227. Search devices selection element 1930*c* allows provider 204 to search for health data sources 227. In response to the selection of search devices selection element 1930*c*, user application engine 120 displays a screenshot of available health data sources 227, or a screenshot of a specific health data source 227, such as the screenshot of FIG. 48, which are described below. Health information processing system 202 selection element 1930*d* allows provider 204 to access, add, or modify information related to health data sources 227 that is provided by provider 204 to health information processing system 202.

Figure 20:
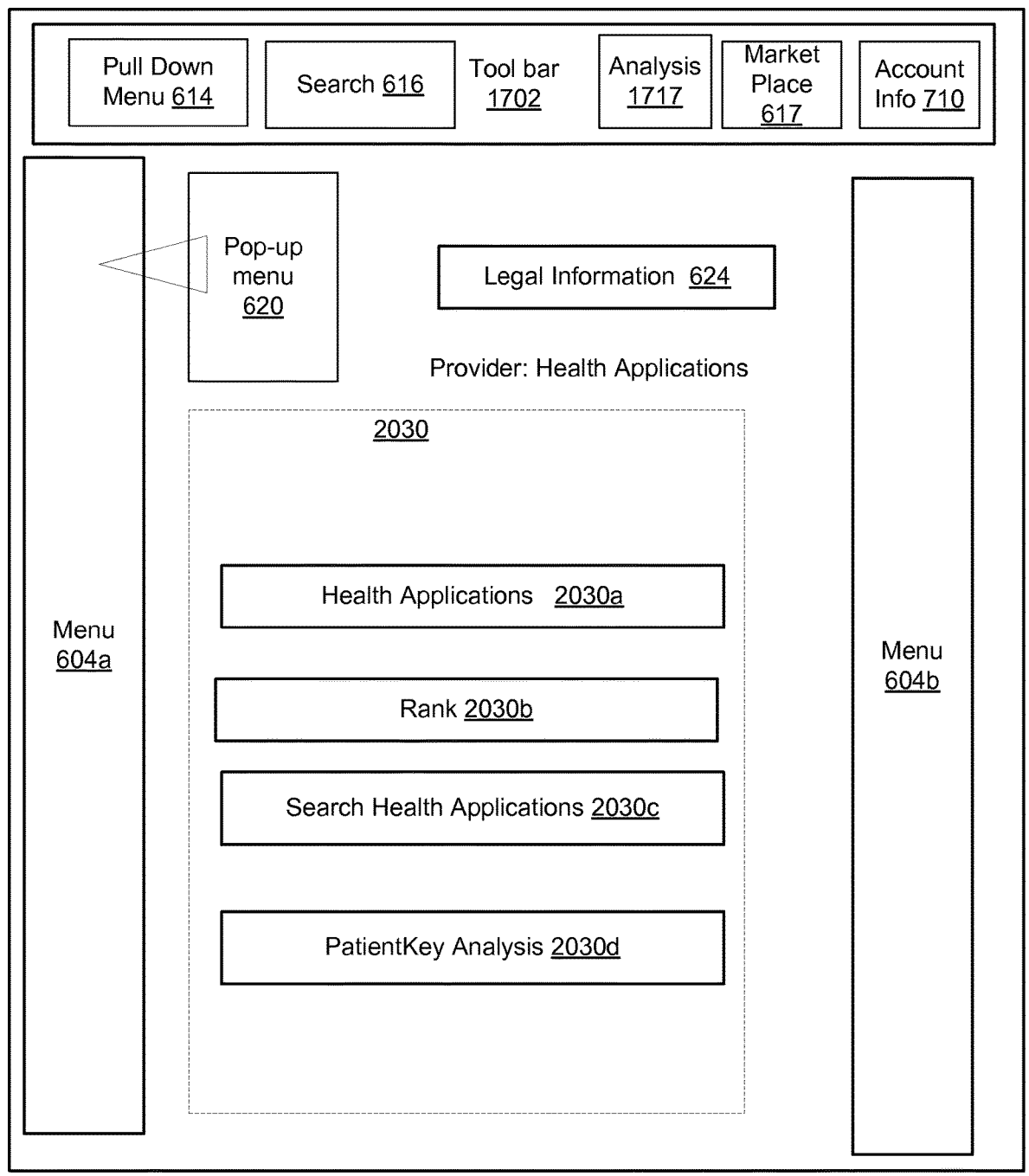
FIG. 20 illustrates a screenshot for health applications accessible by a provider in the process of FIGS. 15a and 15b.

FIG. 20 illustrates a screenshot 2000, which may be generated in response to selection of health applications selection element 1730*c* (FIG. 17), for health applications accessible by a provider in the process of FIGS. 15*a* and 15*b*. Screenshot 2000 comprises a tool bar 1702, a plurality of menus 604*a* and 604*b*, a legal information selection element 624, and a provider health applications menu 2030.

Provider health applications menu 2030 comprises a health applications selection element 2030*a*, a ranking selection element 2030*b*, a search health applications selection element 2030*c*, and a health information processing system 202 selection element 2030*d*. Health applications selection element 2030*a* allows provider 204 to access, add, or modify information related to health applications. Ranking selection element 2030*b* allows provider 204 to access, add, or modify information related to ranking health applications. Search health applications selection element 2030*c* allows provider 204 to access, add, or modify information related to search for health applications. Health information processing system 202 selection element 2030*d* allows provider 204 to access, add, or modify information related to health applications that is provided by provider 204 to health information processing system 202.

Figure 21:
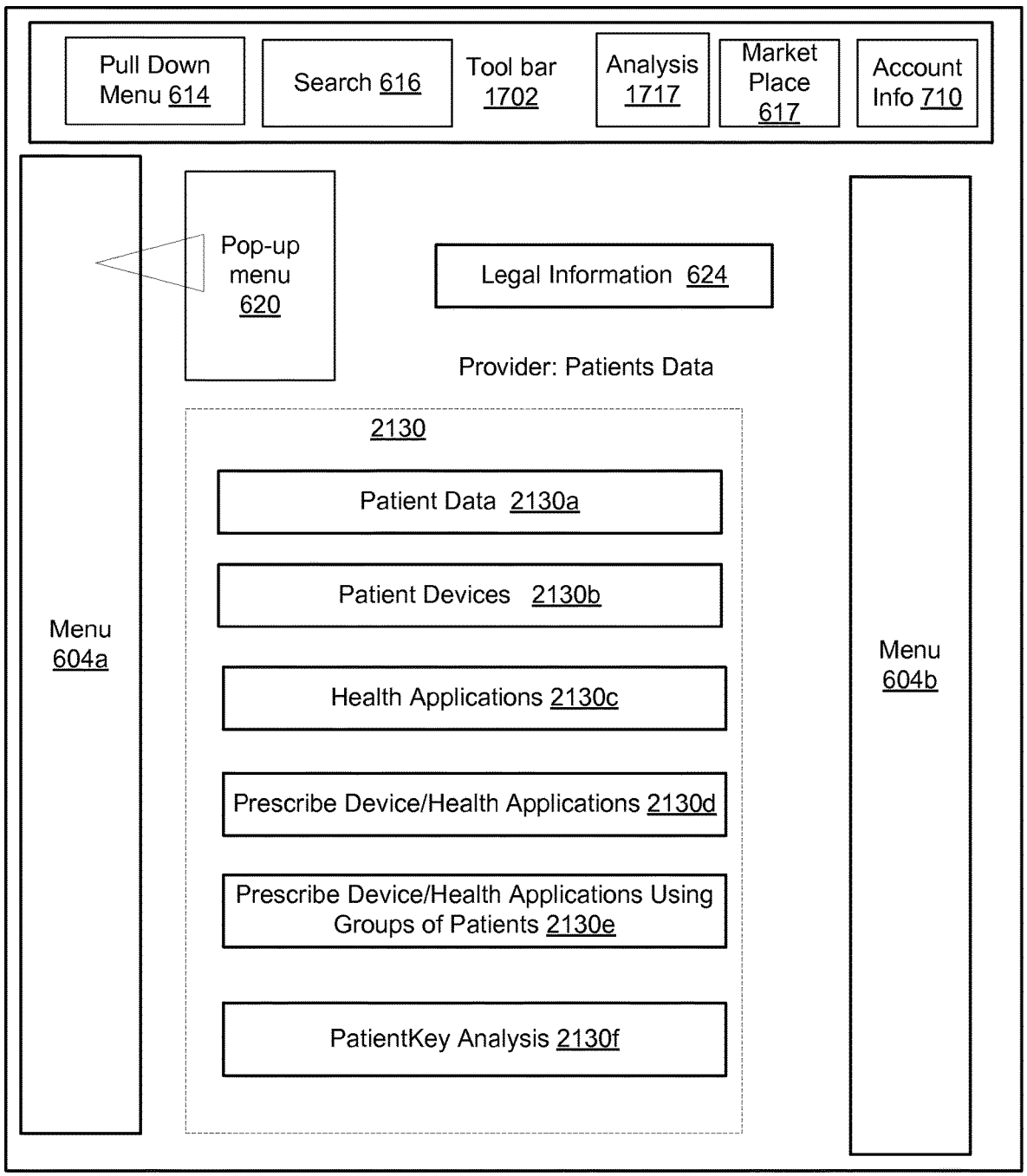
FIG. 21 illustrates a screenshot for patient data accessible by a provider in the process of FIGS. 15a and 15b.

FIG. 21 illustrates a screenshot 2100, which may be generated in response to selection of patient selection element 1730*d* (FIG. 17), for patient data accessible by a provider in the process of FIGS. 15*a* and 15*b*. Screenshot 2100 comprises a tool bar 1702, a plurality of menus 604*a* and 604*b*, a legal information selection element 624, and a patient data menu 2130.

Patient data menu 2130 comprises a patient data selection element 2130*a*, a patient devices selection element 2130*b*, a health application selection element 2130*c*, a patient prescribing selection element 2130*d*, a group based prescribing selection element 2130*e*, and a health information processing system 202 selection element 2130*f*. Patient data selection element 2130*a* allows provider 204 to access, add, or modify information related to patient data. In response to the selection of patient data selection element 2130*a*, health information processing system 202 may display the screenshot of FIG. 56. Patient devices selection element 2130*b* allows provider 204 to access, add, or modify information related to health data sources 227 that are used by patients 208 of provider 204. Health application selection element 2130*c* allows provider 204 to access, add, or modify information related to health applications that are used by patients 208 of provider 204. Patient prescribing selection element 2130*d* allows provider 204 to access, add, or modify information related to prescribing health data sources 227 or health applications or bundles thereof to patient 208. Prescriptions of health applications or health data sources 227 or bundles thereof may be made automatically based on criteria set by provider 204 or manual by provider 204. Group based prescribing selection element 2130*e* allows provider 204 to access, add, or modify information related to prescribing health data sources 227 or health applications or bundles thereof using groups of patients 208, or analysis of patient data, devices or health applications by health information processing system 202. Health information processing system 202 selection element 2130*f* allows provider 204 to access, add, or modify information related to analysis of patient data that is provided by provider 204 to health information processing system 202.

Figure 22:
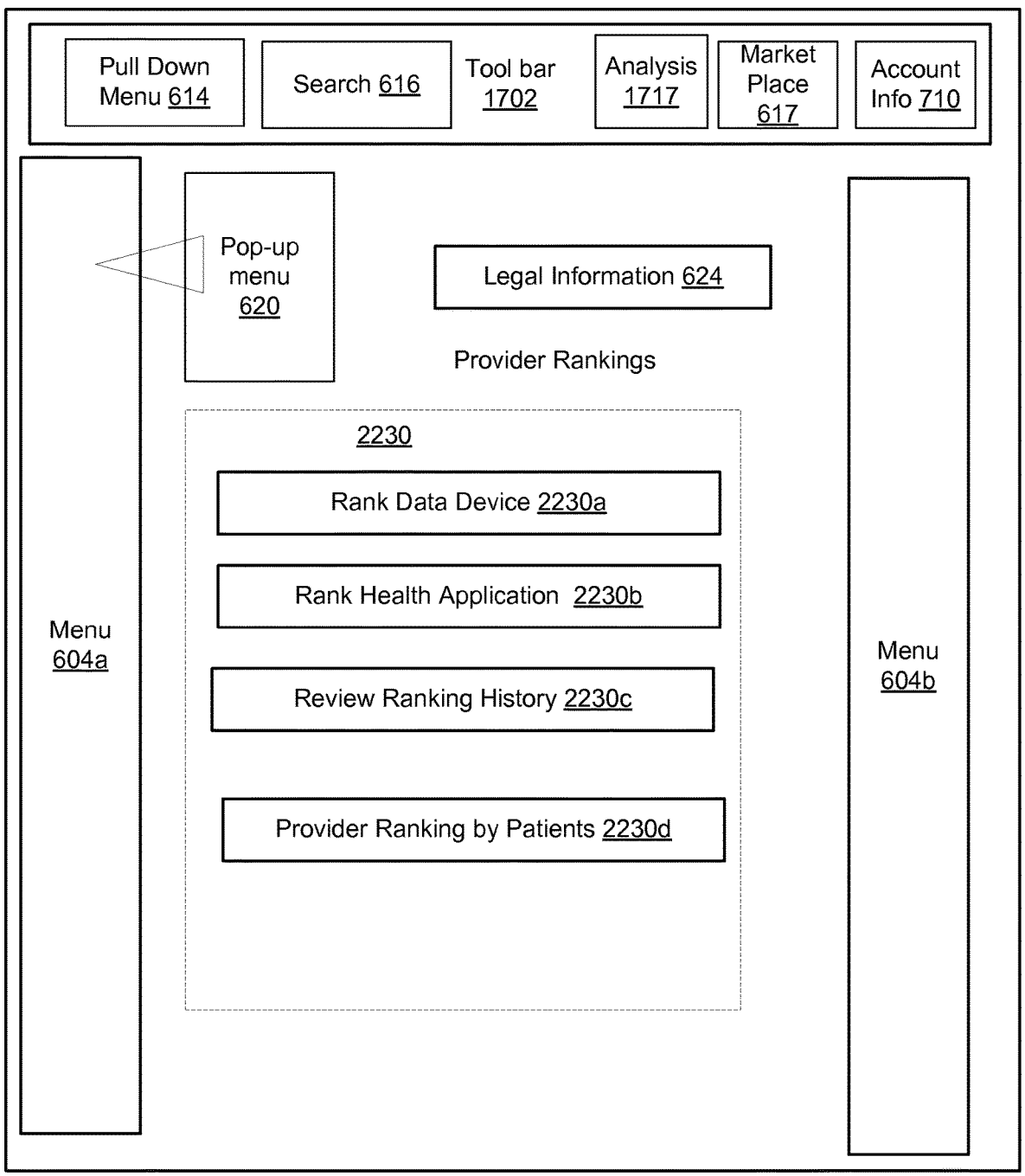
FIG. 22 illustrates a screenshot for rankings by a provider in the process of FIGS. 15a and 15b.

FIG. 22 illustrates a screenshot 2200, which may be generated in response to selection of rank selection element 1730*e* (FIG. 17), for rankings by a provider in the process of FIGS. 15*a* and 15*b*. Screenshot 2200 comprises a tool bar 1702, a plurality of menus 604*a* and 604*b*, a legal information selection element 624, and a ranking menu 2230.

Ranking menu 2230 comprises a rank data device selection element 2230*a*, a rank health application selection element 2230*b*, a review ranking history selection element 2230*c*, and a provider ranking selection element 2230*d*. Rank data device selection element 2230*a* allows provider 204 to access, add, or modify information related to rankings of health data sources 227. Rank health application selection element 2230*b* allows provider 204 to access, add, or modify information related to rankings of health applications. Review ranking history selection element 2230*c* allows provider 204 to access, add, or modify information related to the history of rankings by provider 204. Rankings are described in conjunction with FIGS. 39-46. Provider ranking selection element 2230*d* allows provider 204 to access, add, or modify information related to rankings of provider 204 by patients 208 of provider 204.

Figure 23:
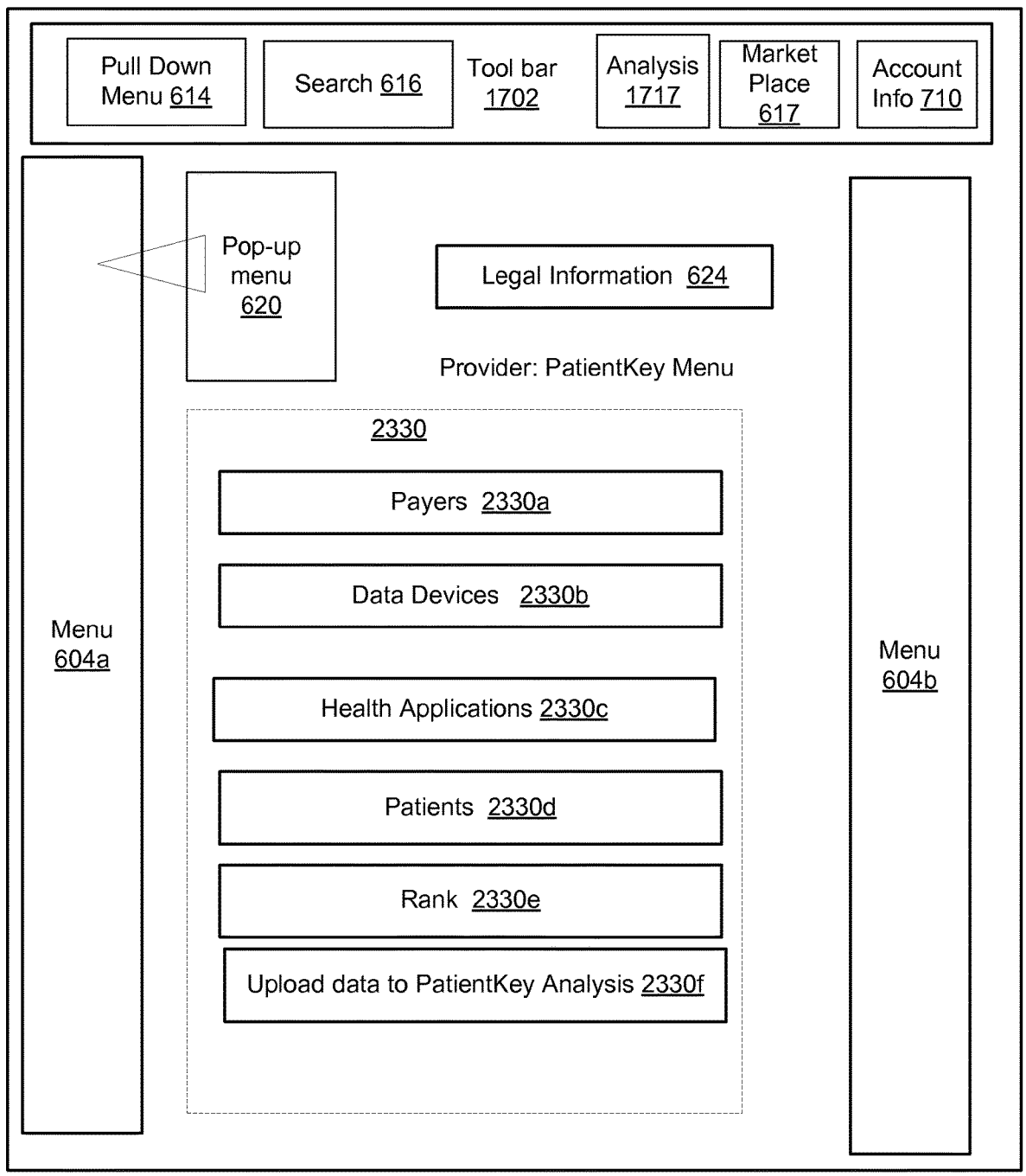
FIG. 23 illustrates a screenshot for the health data processing system of FIG. 2 accessible by a provider in the process FIGS. 15a and 15b.

FIG. 23 illustrates a screenshot 2300, which may be generated in response to selection of health information processing system 202 selection element 1730*f* (FIG. 17), for the health data processing system of FIG. 2 accessible by a provider in the process FIGS. 15*a* and 15*b*. Screenshot 2300 comprises a tool bar 1702, a plurality of menus 604*a* and 604*b*, a legal information selection element 624, and a health information processing system 202 menu 2330.

Health information processing system 202 menu 2330 comprises a payers selection element 2330*a*, a data device selection element 2330*b*, a health application selection element 2330*c*, a patient selection element 2330*d*, a ranking selection element 2330*e*, and an upload selection element 2330*f*. Payers selection element 2330*a* allows provider 204 to access, add, or modify information related to payers 206. Data device selection element 2330*b* allows provider 204 to access, add, or modify information related to health data sources 227 used by patients 208 of provider 204 or on the market or in development. Health application selection element 2330c allows provider 204 to access, add, or modify information related to health applications used by patients 208 of provider 204 or on the market or in development. Patient selection element 2330d allows provider 204 to access, add, or modify information related to patents 208 of provider 204. The information is information that patent 108 has authorized provider 204 to access (see FIG. 9). Ranking selection element 2330e allows provider 204 to access, add, or modify information related to rankings by provider 204 (see FIG. 22) or otherwise provided by health information processing system 202. Upload selection element 2330f allows provider 204 to upload new or modified information from provider 204 to health information processing system 202. Health information processing system 202 may provide analysis to providers 204, such as the number of patients 208 that are using a health application or health data source 227 recommended by the provider, improvement in health of patients 208 who are using a particular health application or health data source 227, comparison in health improvement of patients 208 who are using a health application or health data source 227 and others who are not using any health application or health data source 227, what their patients are saying about them, and the like.

FIGS. 24a and 24b illustrate a process for health information processing system 202 for a payer 206. At 2402, user application engine 320 generates a user interface, such as the screenshot 2500 of FIG. 25, which is described below, for display on an interface of payer 206 for payer 206 to login. At 2404, security engine 304 authenticates payer 206, and if authenticated, user application engine 320 generates a user interface, such as the screenshot 2600 of FIG. 26 or a screenshot 6000 of FIG. 60, which are described below, for display for payer 206 to select an action.

At 2406, user application engine 320 receives a request from payer 206. If, at 2408, payer 206 selects provider data, at 2410, user application engine 320 performs the requested action and generates a user interface of provider data, such as the screenshot 2700 of FIG. 27, which is described below, for display on an interface of payer 206 for payer 206 to select an action. User application engine 320 executes a payer 206 request from the screenshot generated at 2410 or returns to waiting to receive a payer 206 request at 2406.

If, at 2412, payer 206 selects device data, at 2414, user application engine 320 performs the requested action and generates a user interface of health data sources 227, such as the screenshot 2800 of FIG. 28, which is described below, for display on an interface of payer 206 for payer 206 to select an action. User application engine 320 executes a payer 206 request from the screenshot generated at 2414 or returns to waiting to receive a payer 206 request at 2406.

If, at 2416, payer 206 selects health application, at 2418, user application engine 320 performs the requested action and generates a user interface of health applications, such as the screenshot 2900 of FIG. 29, which is described below, for display on an interface of payer 206 for payer 206 to select an action. User application engine 320 executes a payer 206 request from the screenshot generated at 2418 or returns to waiting to receive a payer 206 request at 2406.

If, at 2420, payer 206 selects patient, at 2422, user application engine 320 performs the requested action and generates a user interface of patient data, such as the screenshot 3000 of FIG. 30, which is described below, for display on an interface of payer 206 for payer 206 to select an action. User application engine 320 executes a payer 206 request from the screenshot generated at 2422 or returns to waiting to receive a payer 206 request at 2406.

If, at 2428, payer 206 selects access to health information processing system 202, at 2430, user application engine 320 performs the requested action and generates a user interface for access to health information processing system 202, such as the screenshot 3100 of FIG. 31, which is described below, for display on an interface of payer 206 for payer 206 to select an action. User application engine 320 executes a payer 206 request from the screenshot generated at 2430 or returns to waiting to receive a payer 206 request at 2406.

Figure 24:
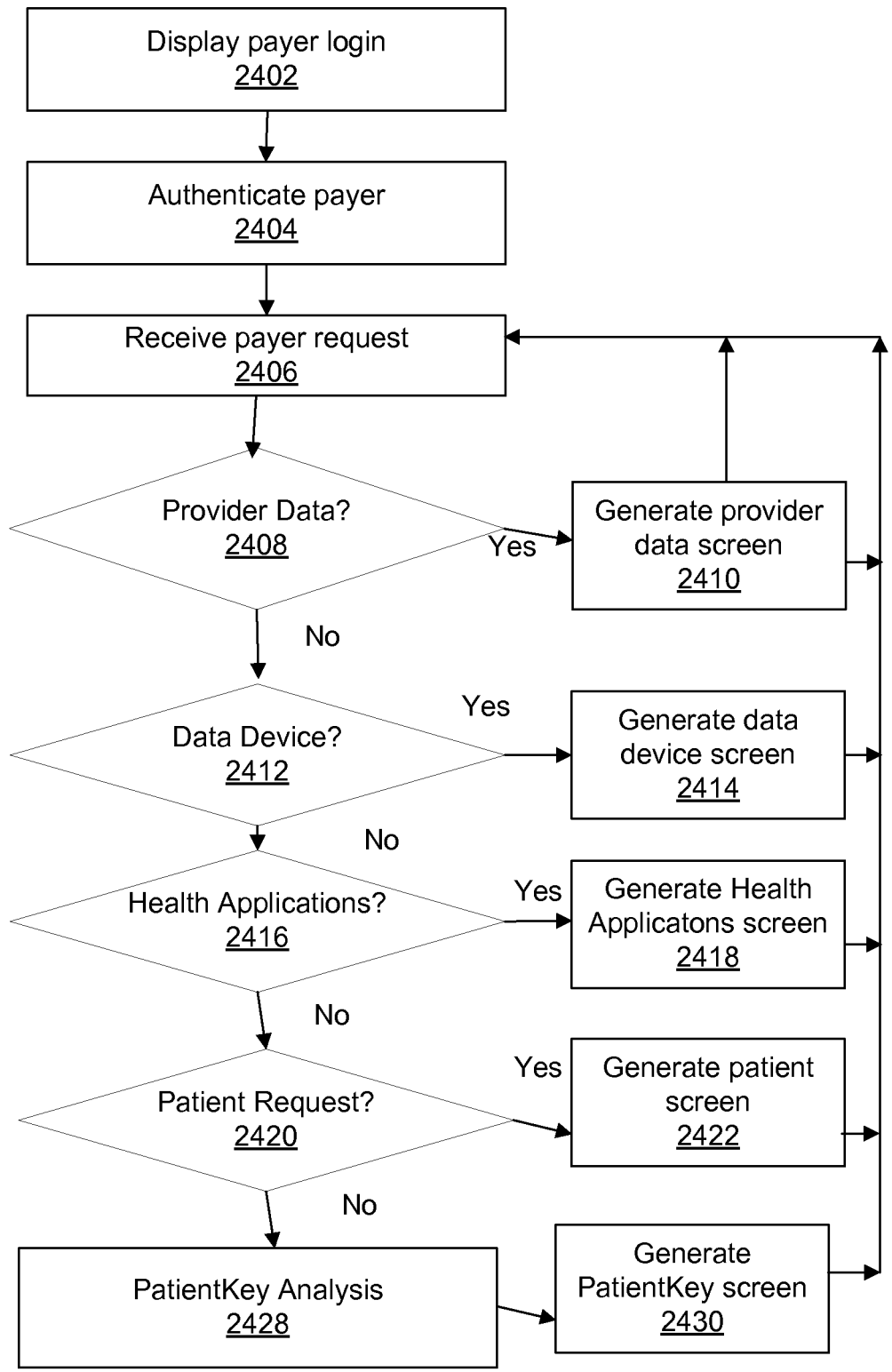
FIG. 24 illustrates a process for a payer of the health data processing system of FIG. 2.
Figure 25:
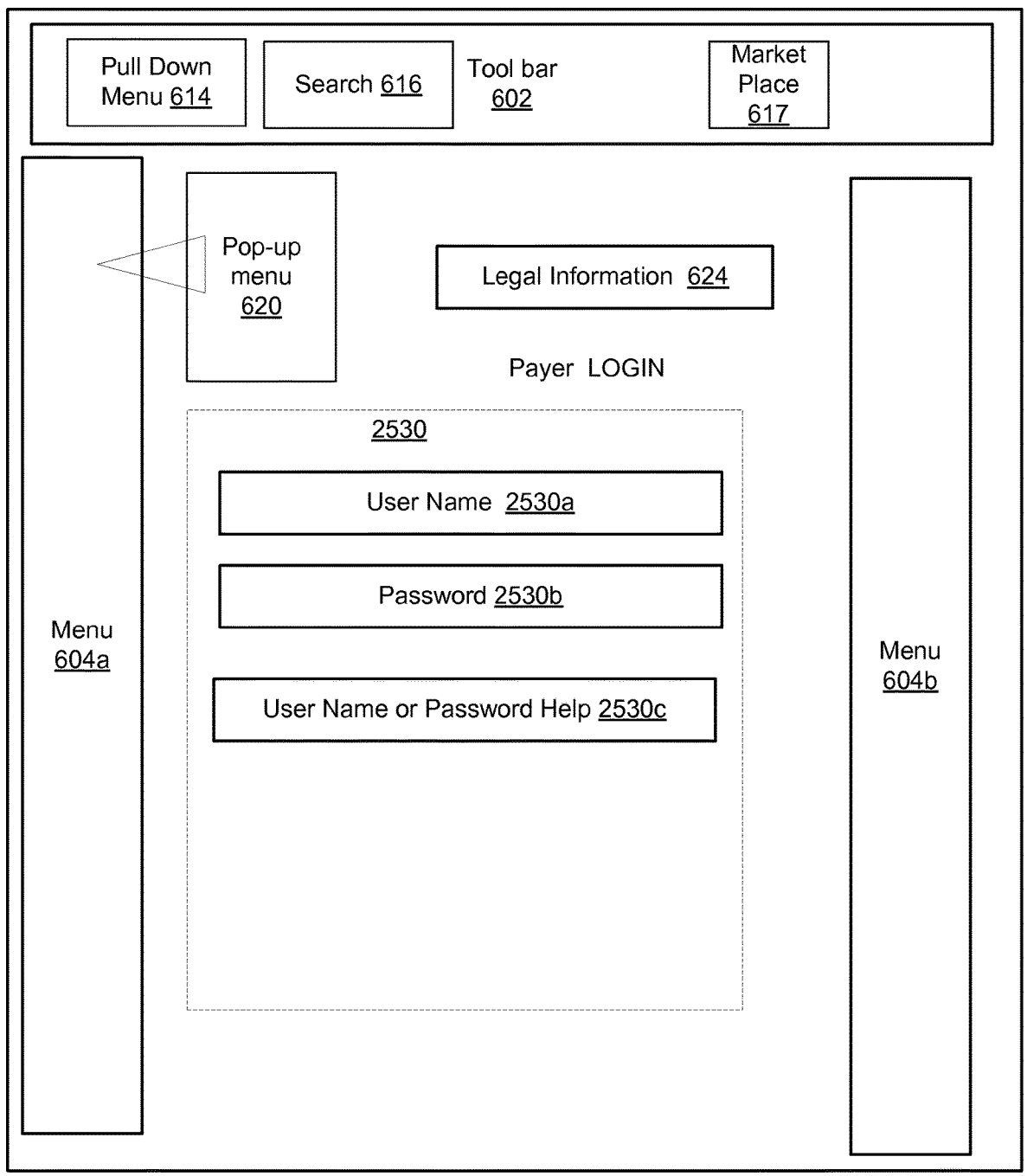
FIG. 25 illustrates a screenshot for payer login in the process of FIG. 24.

FIG. 25 illustrates a screenshot 2500 for the login of payer 206 in the process of FIG. 24. Screenshot 2500 comprises a tool bar 602, a plurality of menus 604a and 604b, a legal information selection element 624, and a login menu 2530.

Login menu 2530 comprises a user name selection element 2530a and a password selection element 2530b for payer 206 to enter a user name and password, respectively. Login menu 2530 further comprises a user name or password help selection element 2530c to assist payer 206 if payer 206 has forgotten the user name or password.

Figure 26:
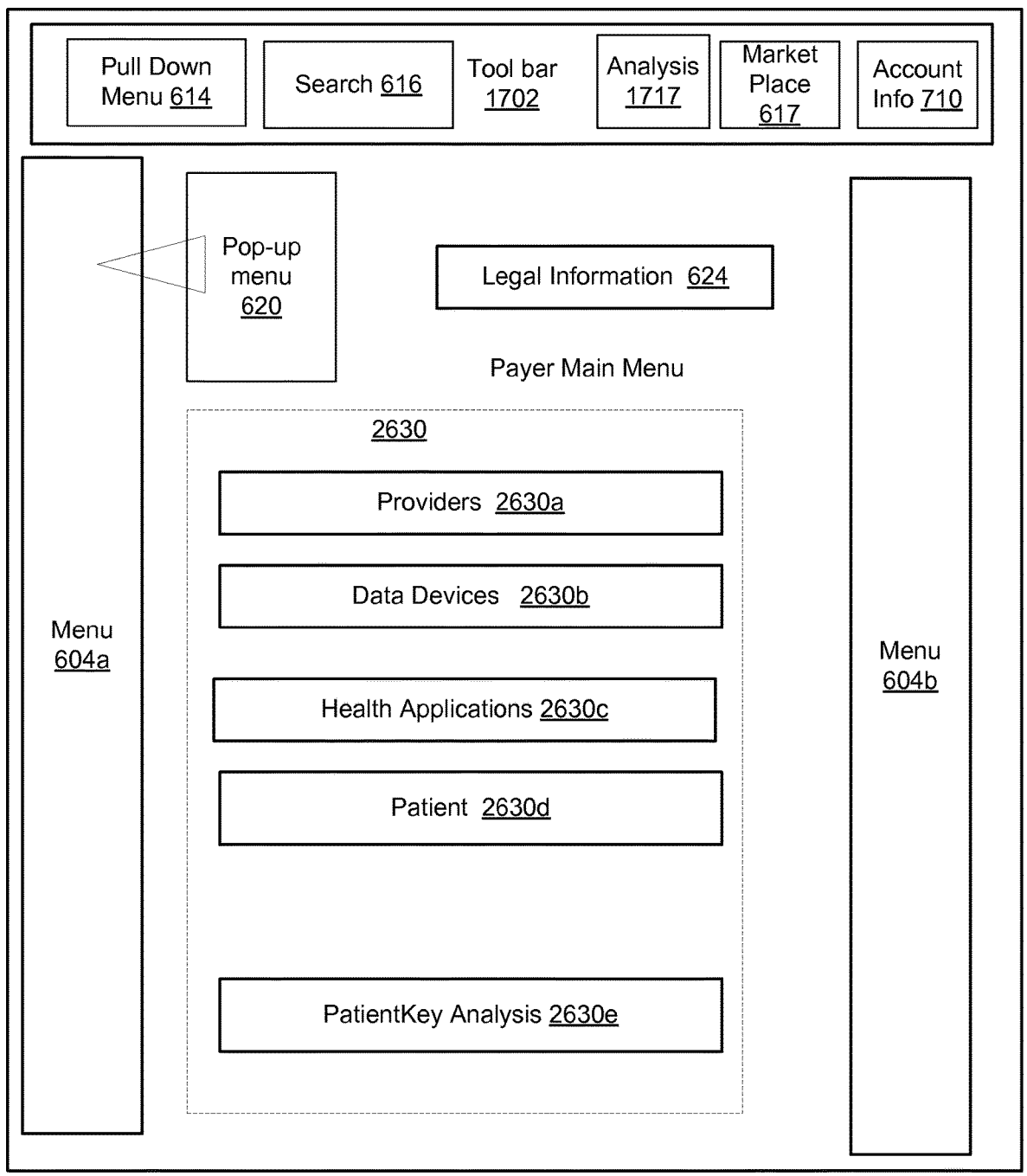
FIG. 26 illustrates a screenshot for payer main menu options in the process of FIG. 24.

FIG. 26 illustrates a screenshot 2600 for payer main menu options in health information processing system 202 for payer 206. Screenshot 2600 comprises a tool bar 1702, a plurality of menus 604a and 604b, a legal information selection element 624, and a payer option menu 2630.

Payer option menu 2630 comprises a provider data selection element 2630a, a data device selection element 2630b, a health applications selection element 2630c, a patient selection element 2630d, and a health information processing system 202 selection element 2630e. Provider data selection element 2630a allows payer 206 to access, add, or modify information related to payer 206, composite data of patients, and set up or change account information or features of health information processing system 202. Selecting provider data selection element 2630a is described below in conjunction with FIG. 27.

Data device selection element 2630b allows payer 206 to access, add, or modify information regarding health data sources 227, such as device data, health applications for health data sources 227, or device rankings, or analysis of health data sources 227 by health information processing system 202. Selecting data device selection element 2630b is described below in conjunction with FIG. 28.

Health applications selection element 2630c allows payer 206 to access, add, or modify information regarding health applications, or health application rankings, or analysis of health applications by health information processing system 202. Selecting health applications selection element 2630c is described below in conjunction with FIG. 29.

Patient selection element 2630d allows payer 206 to access, add, or modify information related to a patient 208, such as patient data or health data sources used by patient 208, information related to prescribed health data sources 227, health applications to the patient, or medications, or analysis of provider data, patient data, devices or health applications by health information processing system 202. Selecting patient selection element 2630d is described below in conjunction with FIG. 30.

Health information processing system 202 selection element 2630f allows payer 206 to access, add, or modify data on health information processing system 202, such as finances, efficacy, trends, provider or patient data, or upload data to health information processing system 202. Selecting health information processing system 202 selection element 2630f is described below in conjunction with FIG. 31.

Figure 27:
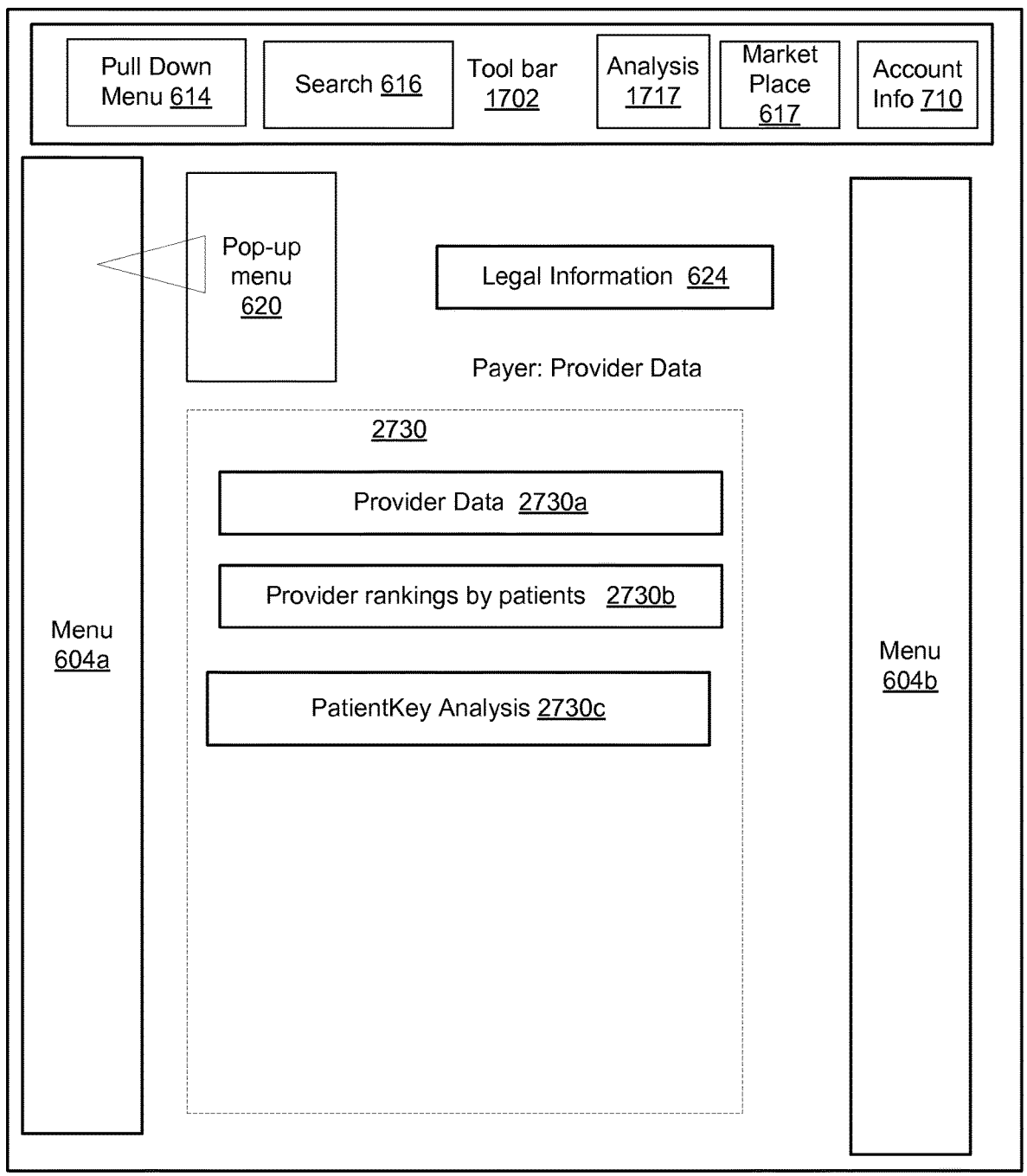
FIG. 27 illustrates a screenshot for provider data accessible by a payer in the process of FIG. 24.

FIG. 27 illustrates a screenshot 2700, which may be generated in response to selection of provider data selection element 2630a (FIG. 26), for provider data accessible by payer 206 in the process of FIG. 24. Screenshot 2700 comprises a tool bar 1702, a plurality of menus 604a and 604b, a legal information selection element 624, and a provider data menu 2730.

Provider data menu 2730 comprises a provider selection element 2730a, a provider ranking by patient data selection element 2730b, and a health information processing system 202 selection element 2730c. Provider selection element 2730a allows payer 206 to access, add, or modify information related to provider 204. Provider ranking by patient data selection element 2730b allows payer 206 to access, add, or modify information related to rankings of providers 204 that are made by patients 208. Health information processing system 202 selection element 2730c allows payer 206 to access, add, or modify analysis of providers 204 by health information processing system 202.

Figure 28:
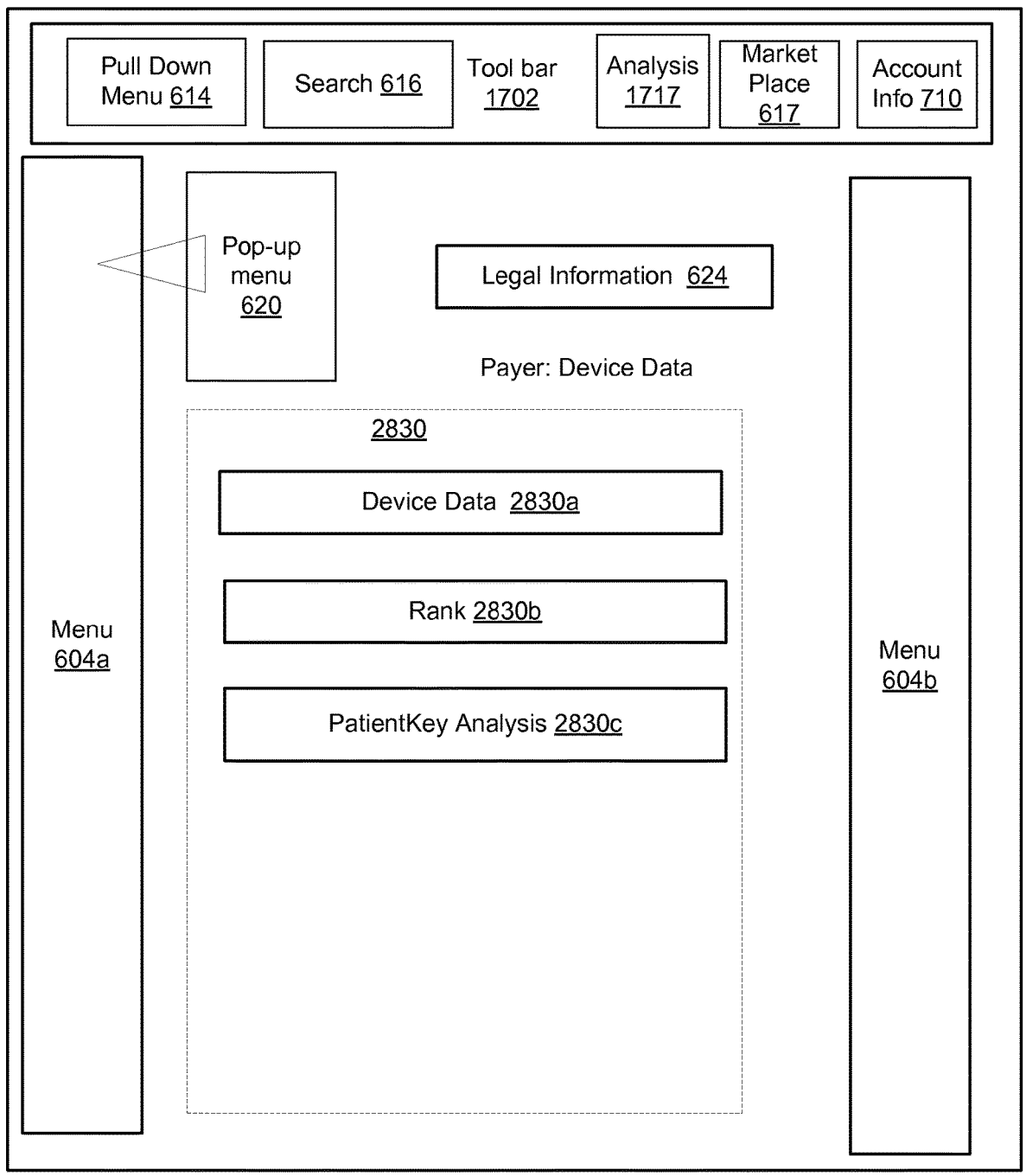
FIG. 28 illustrates a screenshot for device data accessible by a payer in the process of FIG. 24.

FIG. 28 illustrates a screenshot 2800, which may be generated in response to selection of data device selection element 2630b (FIG. 28), for device data accessible by payer 206 in the process of FIG. 24. Screenshot 2800 comprises a tool bar 1702, a plurality of menus 604a and 604b, a legal information selection element 624, and a device data menu 2830.

Device data menu 2830 comprises a device data selection element 2830a, a ranking selection element 2830b, and a health information processing system 202 selection element 2830c. Device data selection element 2830a allows payer 206 to access, add, or modify information related to health data sources 227. Ranking selection element 2830b allows payer 206 to access, add, or modify information related to ranking health data sources 227. Health information processing system 202 selection element 2830c allows payer 206 to access, add, or modify information related to health data sources 227 that is provided by payer 206 to health information processing system 202.

Figure 29:
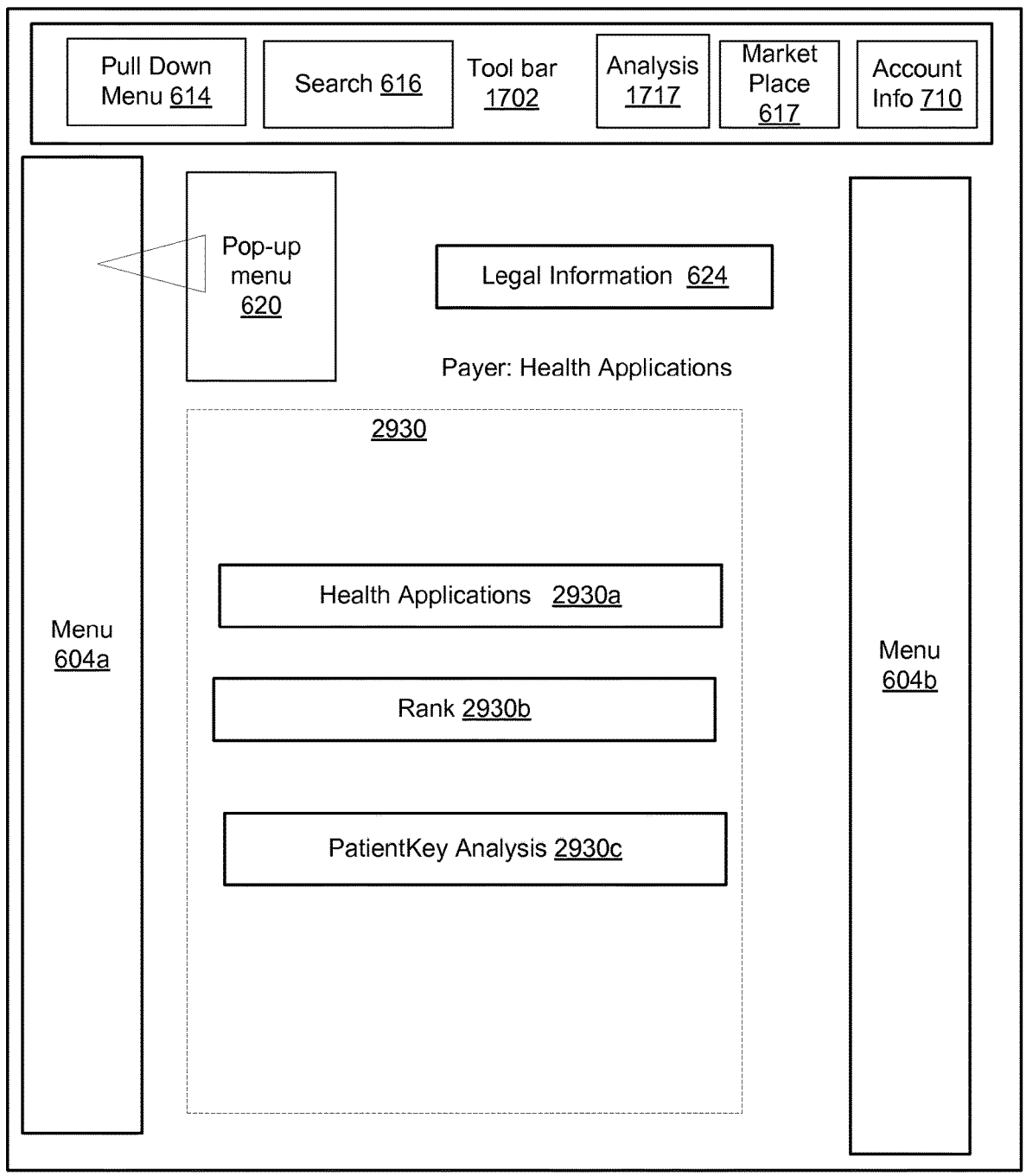
FIG. 29 illustrates a screenshot for health applications data accessible by a payer in the process of FIG. 24.

FIG. 29 illustrates a screenshot 2900, which may be generated in response to selection of health applications selection element 2630c (FIG. 26), for health applications data accessible by payer 206 in the process of FIG. 24. Screenshot 2900 comprises a tool bar 1702, a plurality of menus 604a and 604b, a legal information selection element 624, and a payer health applications menu 2930.

Payer health applications menu 2930 comprises a health applications selection element 2930a, a ranking selection element 2930b, and a health information processing system 202 selection element 2930c. Health applications selection element 2930a allows payer 206 to access, add, or modify information related to health applications. Ranking selection element 2930b allows payer 206 to access, add, or modify information related to ranking health applications. Health information processing system 202 selection element 2930d allows payer 206 to access, add, or modify information related to health applications that is provided by payer 206 to health information processing system 202.

Figure 30:
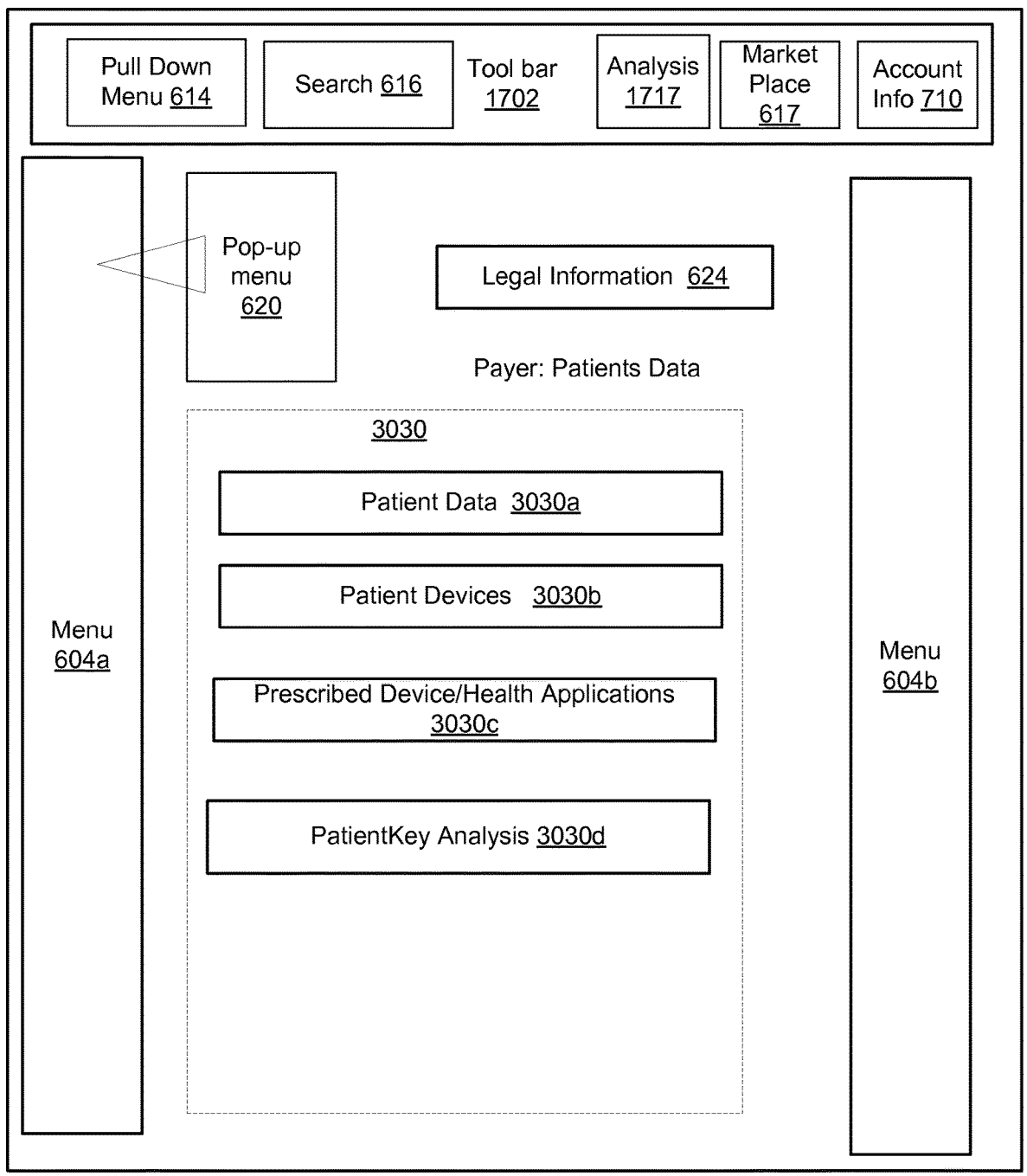
FIG. 30 illustrates a screenshot for patient data accessible by a payer in the process of FIG. 24.

FIG. 30 illustrates a screenshot 3000, which may be generated in response to selection of patient selection element 2630d (FIG. 26), for patient data accessible by a payer 206 in the process of FIG. 24. Screenshot 3000 comprises a tool bar 1702, a plurality of menus 604a and 604b, a legal information selection element 624, and a patient data menu 3030.

Patient data menu 3030 comprises a patient data selection element 3030a, a patient devices selection element 3030b, a patient prescribed selection element 3030c, and a health information processing system 202 selection element 3030e. Patient data selection element 3030a allows payer 206 to access, add, or modify information related to patient data. Patient devices selection element 3030b allows payer 206 to access, add, or modify information related to health data sources 227 that are used by patients 208 that are to be paid by payer 206. Patient prescribed selection element 3030c allows payer 206 to access, add, or modify information related to prescribed health data sources 227 or health applications to the patient. Health information processing system 202 selection element 3030d allows payer 206 to access, add, or modify information related to analysis of patient data that is provided by payer 206 to health information processing system 202.

Figure 31:
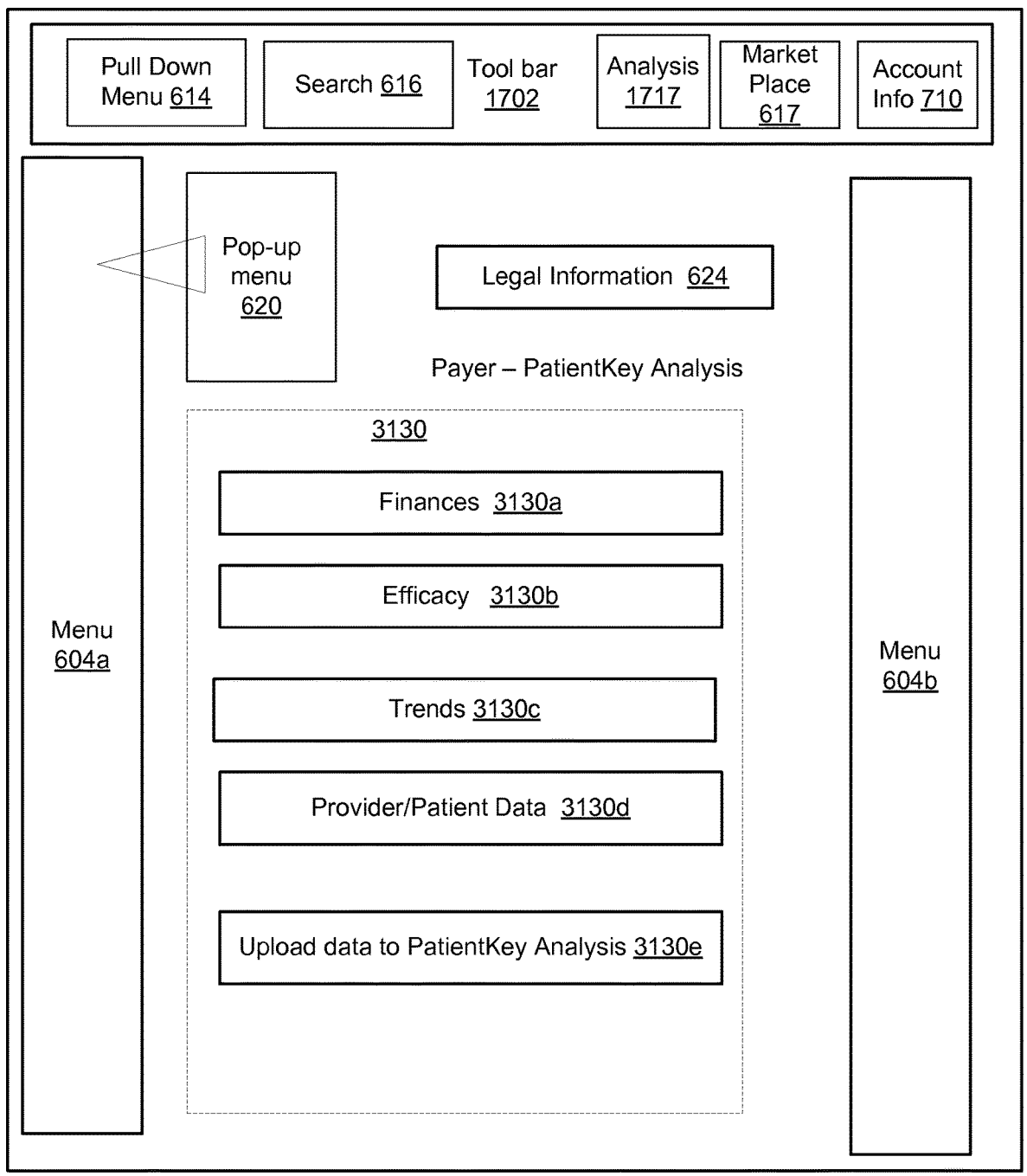
FIG. 31 illustrates a screenshot for the health data processing system of FIG. 2 accessible by a payer in the process of FIG. 24.

FIG. 31 illustrates a screenshot 3100, which may be generated in response to selection of health information processing system 202 selection element 2630f (FIG. 26), for the health data processing system of FIG. 2 accessible by payer 206 in the process of FIG. 24. Screenshot 3100 comprises a tool bar 1702, a plurality of menus 604a and 604b, a legal information selection element 624, and a health information processing system 202 menu 3130.

Health information processing system 202 menu 3130 comprises a finances selection element 3130a, an efficacy selection element 3130b, a trends selection element 3130c, a patient/provider selection element 3130d, and an upload data selection element 3130e. Finances selection element 3130a allows payer 206 to access, add, or modify information related to patients 208, providers 204, or payers 206. Efficacy selection element 3130b allows payer 206 to access, add, or modify information related efficacy of medications, health care, or treatment that is determined in data from other system users 201 by health information processing system 202. Trends selection element 3130c allows payer 206 to access, add, or modify information related to trends determined in data from other system users 201 by health information processing system 202. Patient/provider selection element 3130d allows payer 206 to access, add, or modify information related to patents 208 or providers 204. The information is information that patient 208 has authorized payer 206 to access (see FIG. 9). Upload data selection element 3130e allows payer 206 to upload information related to payer 206 to health information processing system 202. Health information processing system 202 may provide analysis to payers 206, such as the number of patients 208 that are using a health application or health data source 227 recommended by the payer, improvement in health of patients 208 who are using a particular health application or health data source 227, comparison in health improvement of patients 208 who are using a health application or health data source 227 and others who are not using any health application or health data source 227, what their patients are saying about them, and the like.

Figure 32A:
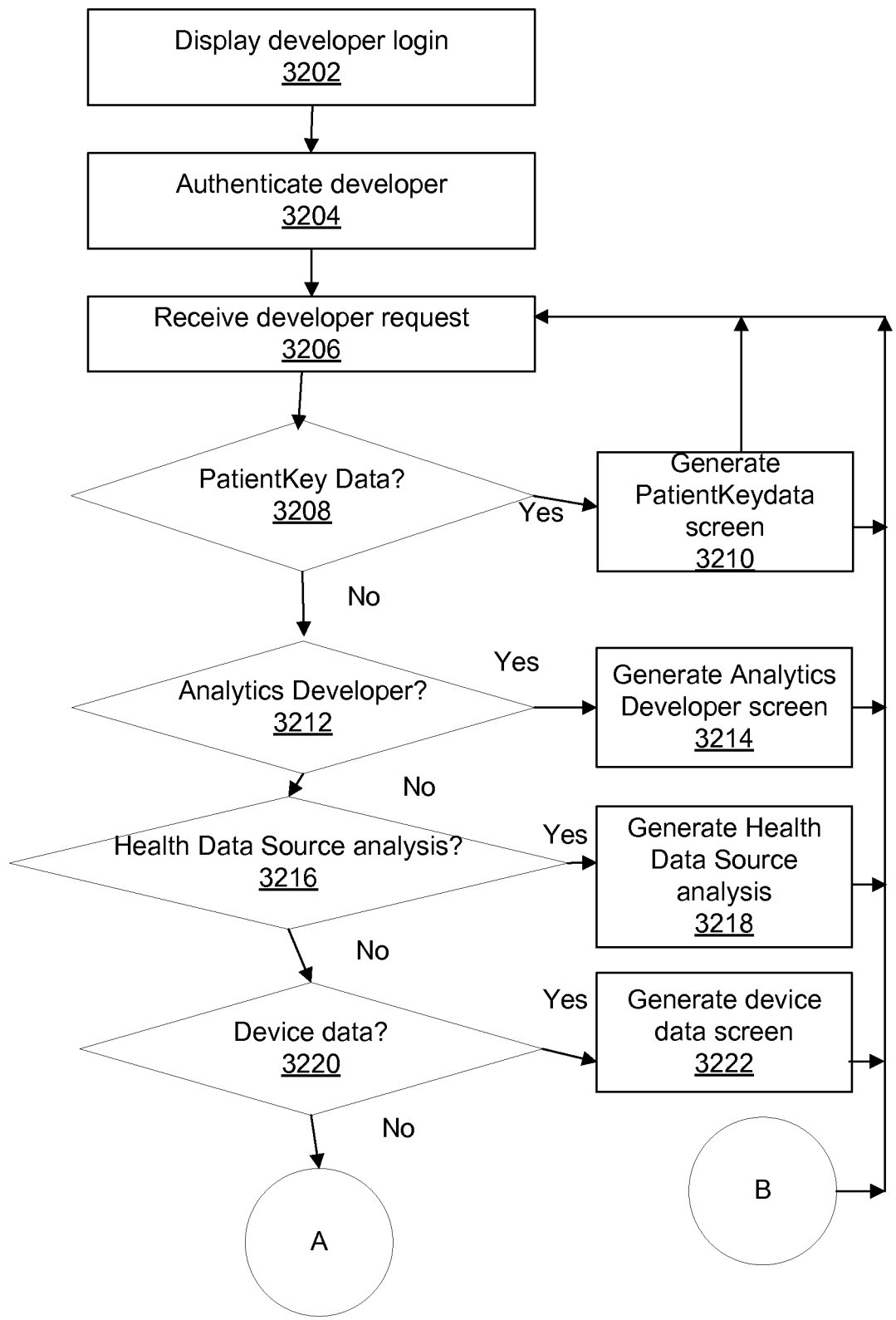
FIGS. 32a and 32b illustrate a process for a health data source developer of the health data processing system of FIG. 2.
Figure 32B:
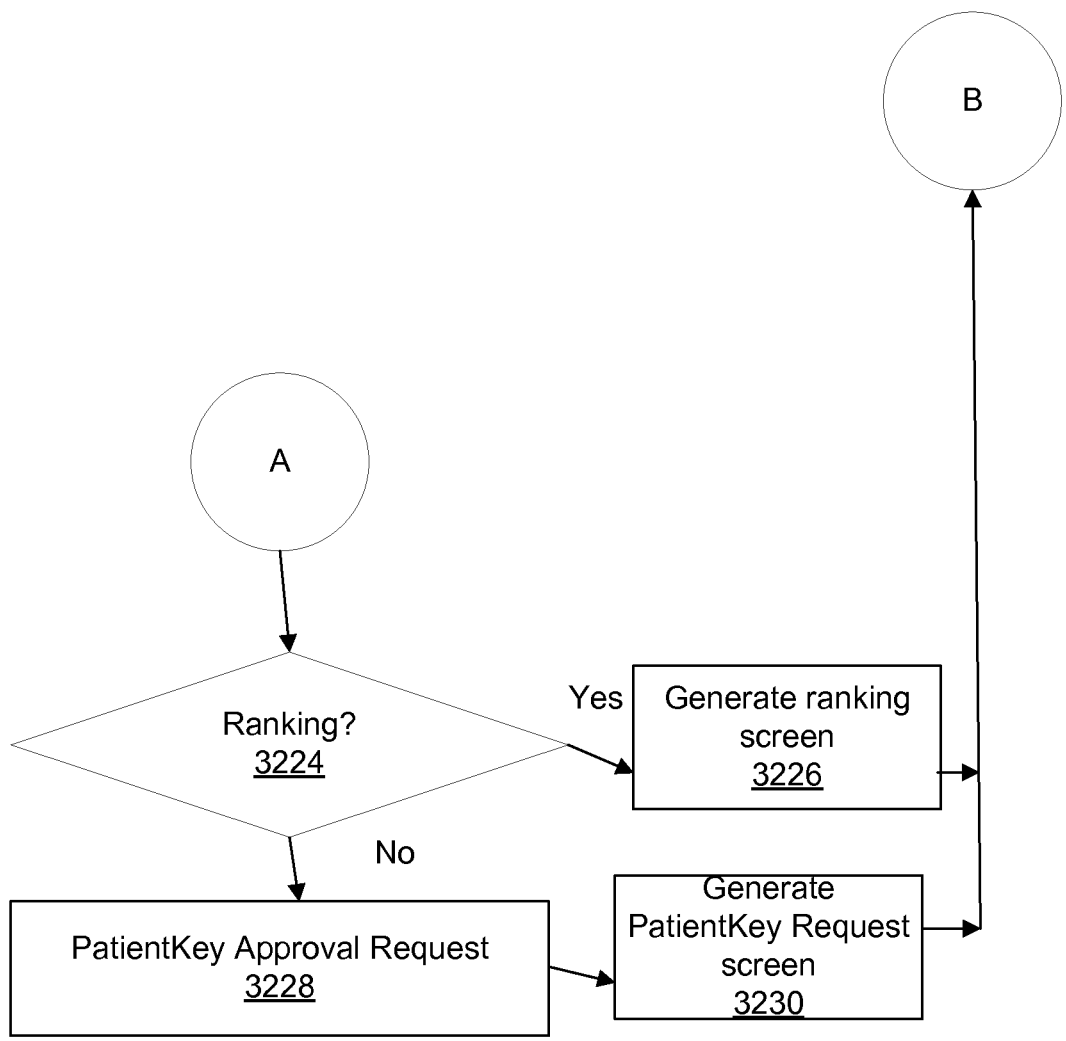

FIGS. 32a and 32b illustrate a process for health information processing system 202 for health data source developer 212. In various embodiments, health information processing system 202 provides a platform for health data source developers 212 to develop health data sources 227 and analytics developers 214 to develop health applications. In some embodiments, health data source developers 212 publish software development kits, application program interfaces, and interface specifications for their data in health information processing system 202. In some embodiments, health information processing system 202 has a standard or protocol for software development kits, application program interfaces, and interface specifications.

At 3202, user application engine 320 generates a user interface, such as the screenshot 3300 of FIG. 33, which is described below, for display on an interface of health data source developer 212 for health data source developer 212 to login. At 3204, security engine 304 authenticates health data source developer 212, and if authenticated, user application engine 320 generates a user interface, such as the screenshot 3400 of FIG. 34, which is described below, for display for health data source developer 212 to select an action.

At 3206, user application engine 320 receives a request from health data source developer 212. If, at 3208, health data source developer 212 selects access to health information processing system 202, at 3210, user application engine 320 performs the requested action and generates a user interface of data of health information processing system 202, such as a screenshot that is similar to screenshot 3100 (FIG. 31), for display on an interface of health data source developer 212 for health data source developer 212 to select an action. User application engine 320 executes a health data source developer 212 request from the screenshot generated at 3210 or returns to waiting to receive a health data source developer 212 request at 3206.

If, at 3212, health data source developer 212 selects analytics developer, at 3214, user application engine 320 performs the requested action and generates information from analytics developers 114 for display on a user interface of health data sources 227 for display on an interface of health data source developer 212 for health data source developer 212 to select an action. Health information processing system 202 may provide analysis to health data source developer 212 as to the effectiveness of their applications or devices, such as the number of patients 208 that are using a health application or health data source 227, comparison in health improvement patients 208 who are using a particular health application or health data source 227, comparison in health improvement of patients 208 who are using a health application or health data source 227 and others who are not using any health application or health data source 227, what their patients are saying about them, and the like. User application engine 320 executes a health data source developer 212 request from the screenshot generated at 3214 or returns to waiting to receive a health data source developer 212 request at 3206.

If, at 3216, health data source developer 212 selects health data sources analysis, at 3218, user application engine 320 performs the requested action and generates a user interface of information for analyzing health data sources 227, such as troubleshooting a defective product or simulation of design changes based on data from health information processing system 202, for display on an interface of health data source developer 212 for health data source developer 212 to select an action. User application engine 320 executes a health data source developer 212 request from the screenshot generated at 3218 or returns to waiting to receive a health data source developer 212 request at 3206.

If, at 3220, health data source developer 212 selects device data, at 3222, user application engine 320 performs the requested action and generates a user interface of device data for display on an interface of health data source developer 212 for health data source developer 212 to select an action, such as view or download device data. User application engine 320 executes a device data request from the screenshot generated at 3222 or returns to waiting to receive a health data source developer 212 request at 3206.

If, at 3224 health data source developer 212 selects ranking, at 3226, user application engine 320 performs the requested action and generates a user interface that displays ranking information and patient comments on health data sources 227 on an interface of health data source developer 212 for health data source developer 212 to select an action. User application engine 320 executes a health data source developer 212 request from the screenshot generated at 3226 or returns to waiting to receive a health data source developer 212 request at 3206.

If, at 3228, health data source developer 212 selects approval request to health information processing system 202, at 3230, user application engine 320 performs the requested action and generates a user interface for access to health information processing system 202 with an approval request of a new or modified health data source 227 for display on an interface of health data source developer 212 for health data source developer 212 to select an action. User application engine 320 executes a health data source developer 212 request from the screenshot generated at 3230 or returns to waiting to receive a health data source developer 212 request at 3206.

Figure 33:
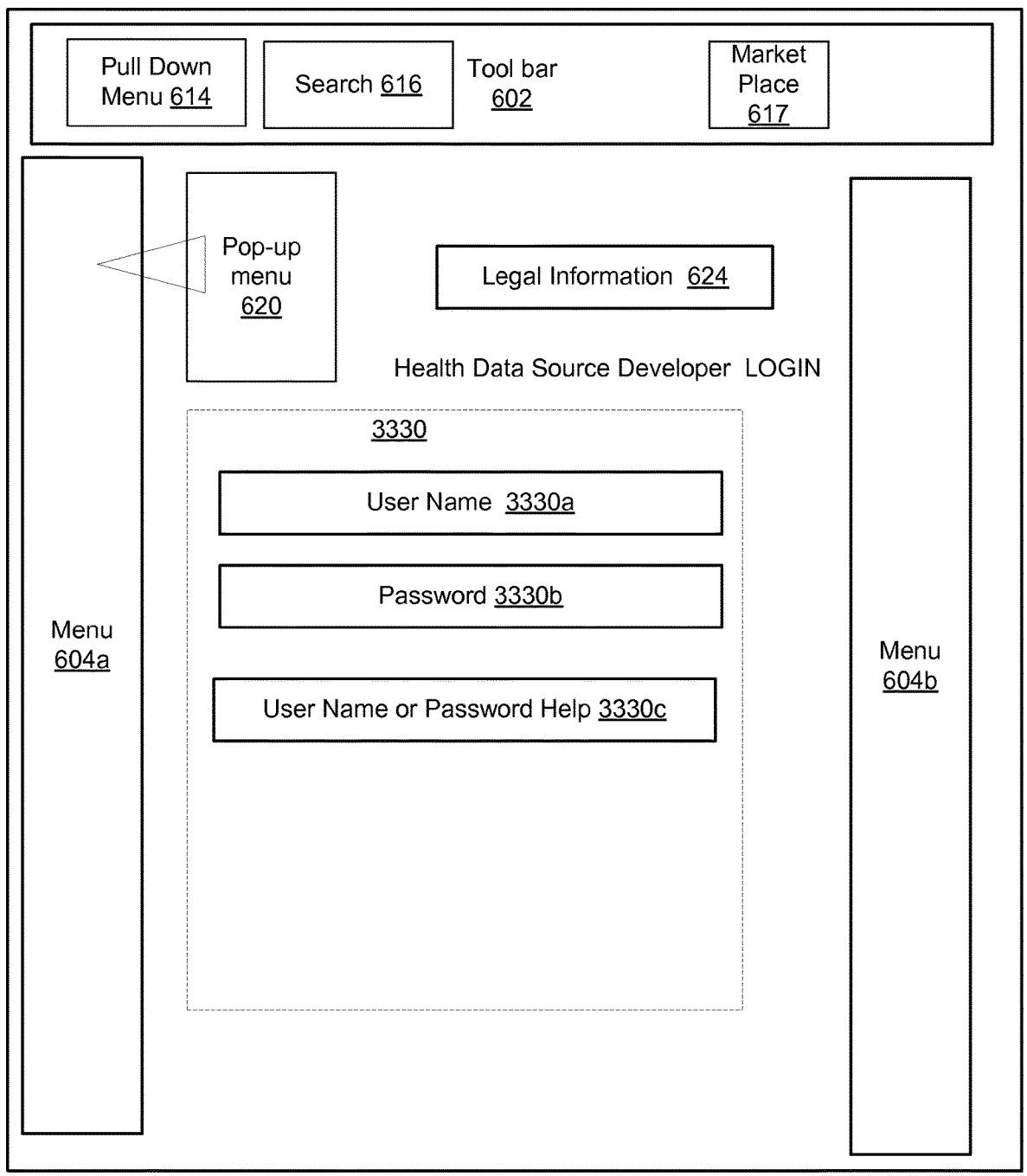
FIG. 33 illustrates a screenshot for health data source developer login in the process of FIGS. 32a and 32b.

FIG. 33 illustrates a screenshot 3300 for the login of health data source developer 212 in the process of FIG. 24. Screenshot 3300 comprises a tool bar 602, a plurality of menus 604a and 604b, a legal information selection element 624, and a login menu 3330.

Login menu 3330 comprises a user name selection element 3330a and a password selection element 3330b for health data source developer 212 to enter a user name and password, respectively. Login menu 3330 further comprises a user name or password help selection element 3330c to assist health data source developer 212 if health data source developer 212 has forgotten the user name or password.

Figure 34:
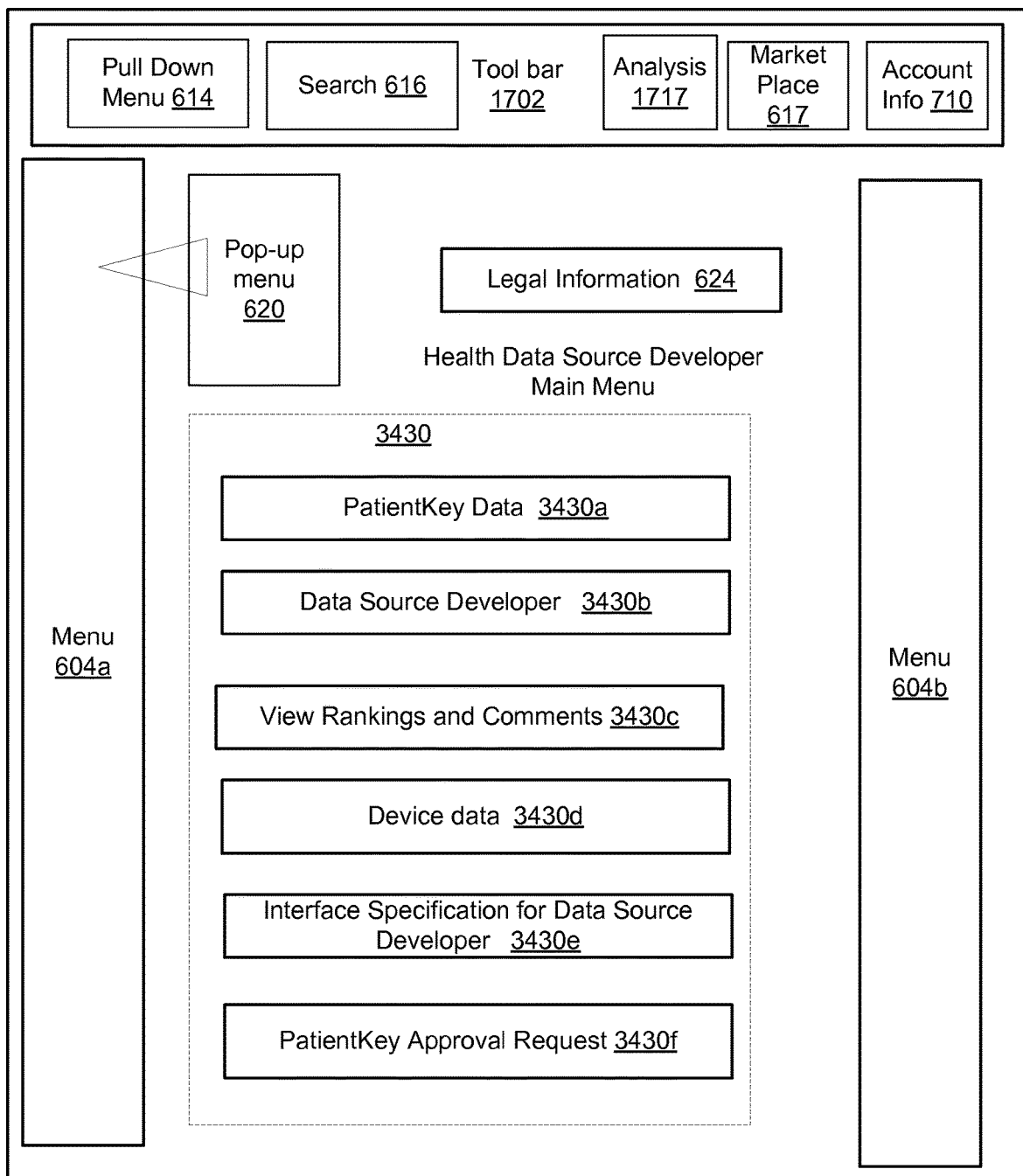
FIG. 34 illustrates a screenshot for health data source developer main menu options in the process of FIGS. 32a and 32b.

FIG. 34 illustrates a screenshot 3400 for health data source developer main menu options in the process of FIGS. 32a and 32b. Screenshot 3400 comprises a tool bar 1702, a plurality of menus 604a and 604b, a legal information selection element 624, and a health data source developer menu 3430.

Health data source developer menu 3430 comprises a health information processing system 202 selection element 3430a, an analytics developer data selection element 3430b, a "view rankings and comments" selection element 3430c, a device data selection element 3430d, an interface specification selection element 3430e, and a information processing system 202 approval selection element 3430f. Health information processing system 202 selection element 3430a allows health data source developer 212 to access, add, or modify information related to data exchanged with or analysis by health information processing system 202. Analytics developer data selection element 3430b allows health data source developers 212 to access, add, or modify information related to analytics developers 214 that are generating health applications for health data sources 227 of health data source developer 212. "View rankings and comments" selection element 3430c allows health data source developer 212 to access, add, or modify information related to rankings and comments by other system users 201. Device data selection element 3430d allows health data source developer 212 to access, add, or modify information related to health data sources 227 for which health data source developer 212 is writing or planning to write health applications. Interface specification selection element 3430e allows health data source developer 212 to access, add, or modify information related to uploading an interface specification for analytics developers 214 to write health applications for health data sources 227 of health data source developer 212 or obtain regulatory approval of the health data source 227. In response to the selection interface specification selection element 3430e, health information processing system 202 may execute the process of FIGS. 64a, 64b, and 64c, which is described below. Information processing system 202 approval selection element 3430f allows health data source developer 212 to access, add, or modify information related to requests by health data source developer 212 for approval of a new or modified health data source 227 by health information processing system 202.

Figure 35:
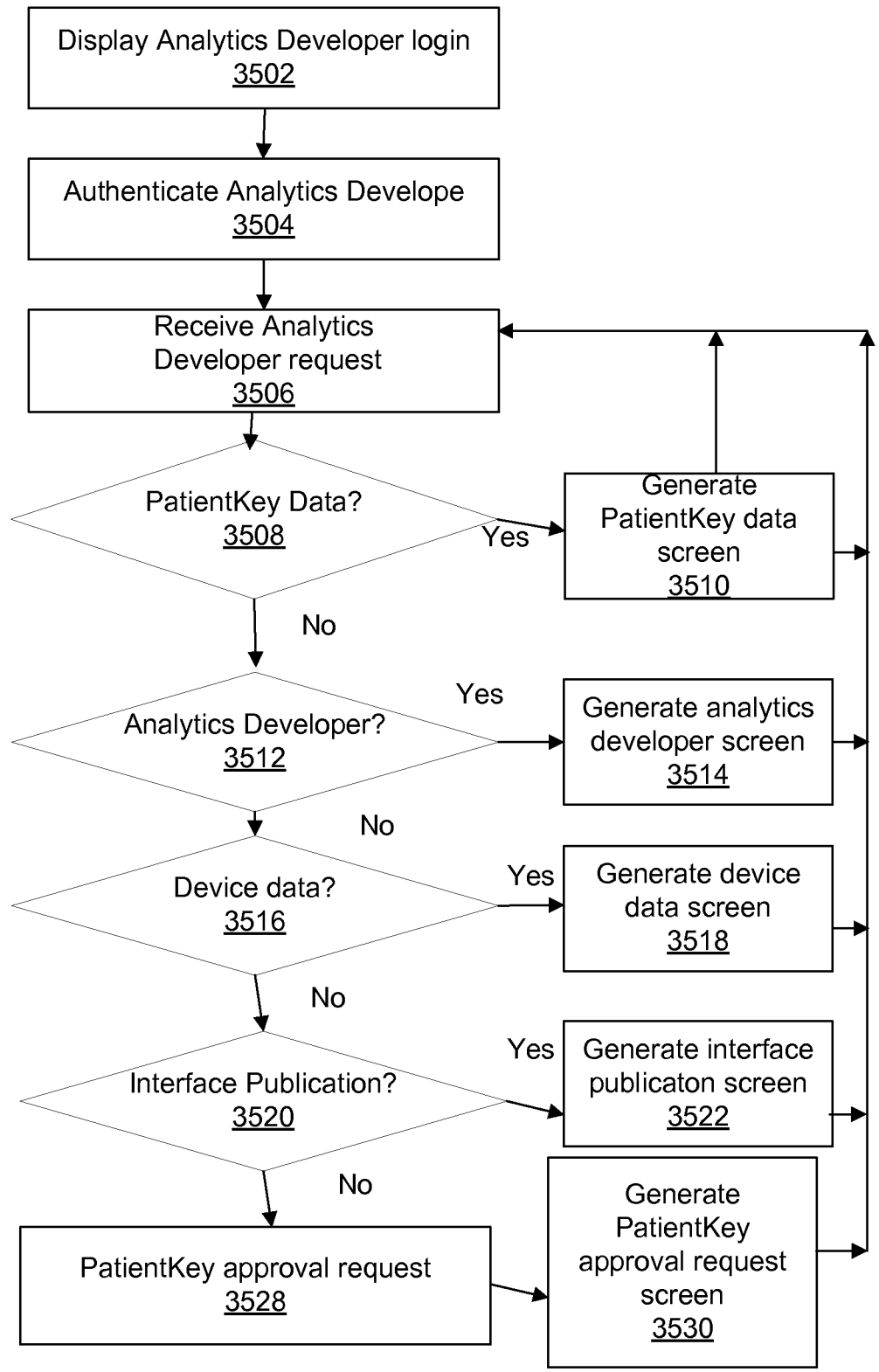
FIG. 35 illustrates a process for an analytics developer of the health data processing system of FIG. 2.

FIG. 35 illustrates a process for health information processing system 202 for analytics developer 214. At 3502, user application engine 320 generates a user interface, such as the screenshot 3600 of FIG. 36, which is described below, for display on an interface of analytics developer 214 for analytics developer 214 to login. At 3504, security engine 304 authenticates analytics developer 214, and if authenticated, user application engine 320 generates a user interface, such as the screenshot 3700 of FIG. 37, which is described below, for display for analytics developer 214 to select an action.

At 3506, user application engine 320 receives a request from analytics developer 214. The analytics developer 214 may, for example, want data related to patient age, body mass index, disease, vitals, allergies, medications, and the like. If, at 3508, analytics developer 214 selects access to health information processing system 202, at 3510, user application engine 350 performs the requested action and generates a user interface of data of health information processing system 202, such as a screenshot that is similar to screenshot 3100 (FIG. 31), for display on an interface of analytics developer 214 for analytics developer 214 to select an action. User application engine 320 executes an analytics developer 214 request from the screenshot generated at 3510 or returns to waiting to receive an analytics developer 214 request at 3506.

If, at 3512, analytics developer 214 selects analytics developer, at 3514, user application engine 320 performs the requested action and generates information from analytics developers 114 for display on a user interface of health data sources 227 for display on an interface of analytics developer 214 for analytics developer 214 to select an action. User application engine 350 executes an analytics developer 214 request from the screenshot generated at 3514 or returns to waiting to receive an analytics developer 214 request at 3506.

If, at 3516, analytics developer 214 selects device data, at 3518, user application engine 350 performs the requested action and generates a user interface of data of health data source 227 for display on an interface of analytics developer 214 for analytics developer 214 to select an action. User application engine 350 executes an analytics developer 214 request from the screenshot generated at 3518 or returns to waiting to receive an analytics developer 214 request at 3506.

If, at 3520, analytics developer 214 selects interface publication, at 3522, user application engine 350 performs the requested action and generates a user interface for publication of interface specification of the health application for display on an interface of analytics developer 214 for analytics developer 214 to select an action, such as view or download the interface specification. User application engine 320 executes a device data request from the screenshot generated at 3522 or returns to waiting to receive an analytics developer 214 request at 3506.

If, at 3528, analytics developer 214 selects approval request to health information processing system 202, at 3530, user application engine 320 performs the requested action and generates a user interface for access to health information processing system 202 with an approval request of a new or modified health application for display on an interface of analytics developer 214 for analytics developer 214 to select an action. User application engine 350 executes an analytics developer 214 request from the screenshot generated at 3530 or returns to waiting to receive an analytics developer 214 request at 3506.

Figure 36:
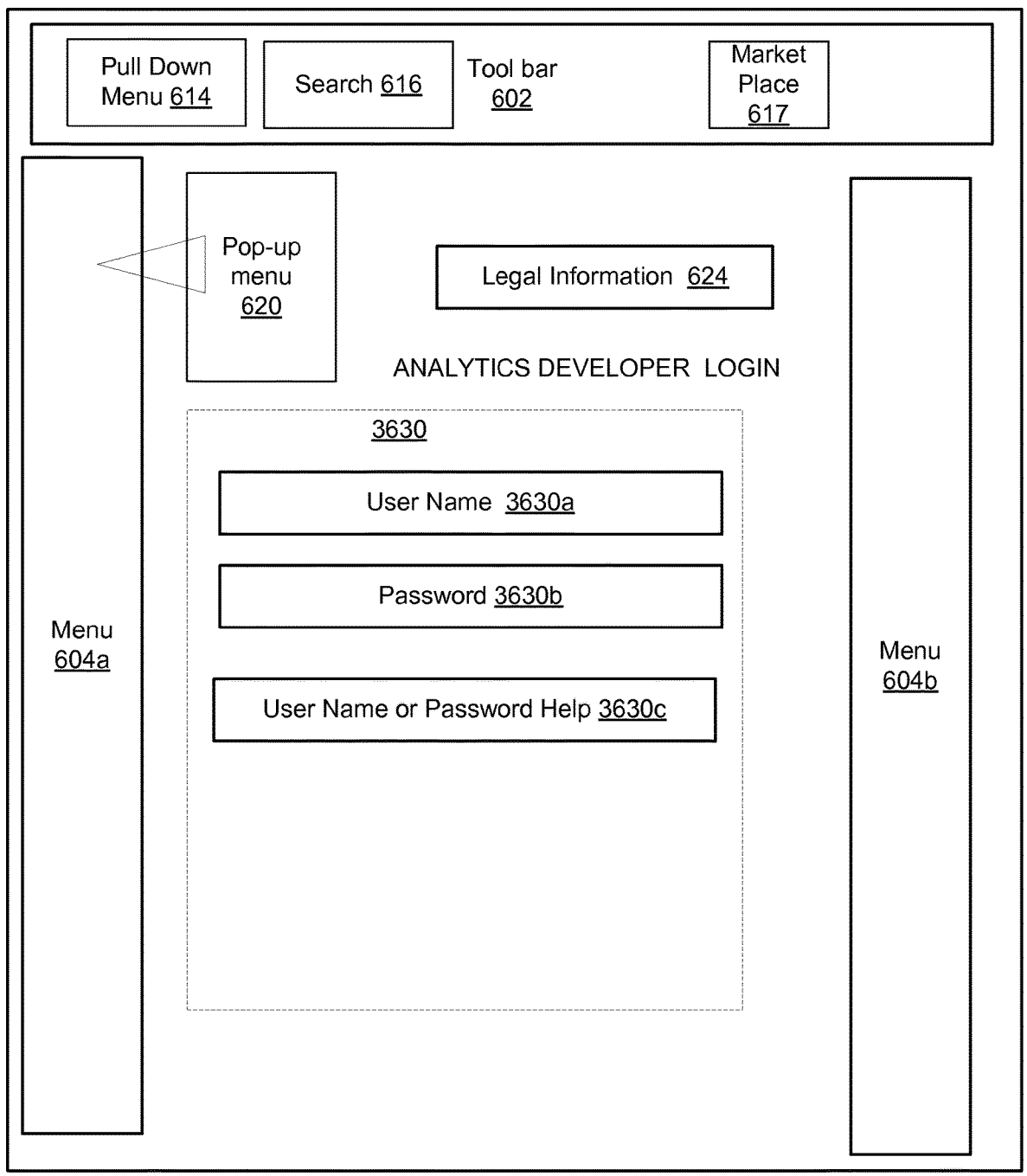
FIG. 36 illustrates a screenshot for analytics developer login in the process of FIG. 35.

FIG. 36 illustrates a screenshot 3600 for the login of analytics developer 214 in the process of FIG. 24. Screenshot 3600 comprises a tool bar 602, a plurality of menus 604a and 604b, a legal information selection element 624, and a login menu 3630.

Login menu 3630 comprises a user name selection element 3630a and a password selection element 3630b for analytics developer 214 to enter a user name and password, respectively. Login menu 3630 further comprises a user name or password help selection element 3630c to assist analytics developer 214 if analytics developer 214 has forgotten the user name or password.

Figure 37:
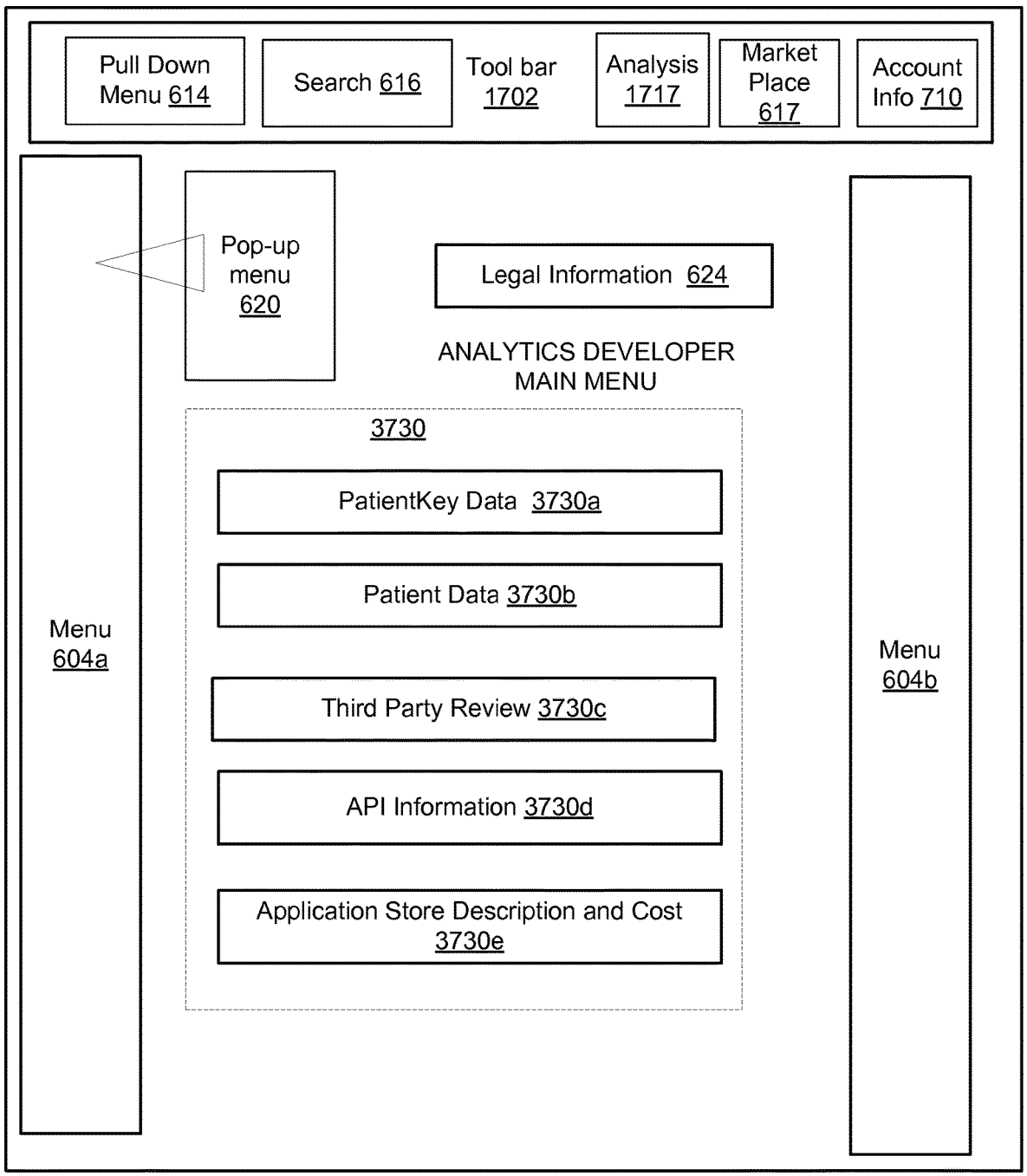
FIG. 37 illustrates a screenshot for analytics developer main menu options in the process of FIG. 35.

FIG. 37 illustrates a screenshot 3700 for analytics developer main menu options for analytics developer 214 in the process of FIG. 35. Screenshot 3700 comprises a tool bar 1702, a plurality of menus 604a and 604b, a legal information selection element 624, and an analytics developer main menu 3700.

Analytics developer main menu 3700 comprises a health information processing system 202 selection element 3730a, a patient data selection element 3730b, a third party review selection element 3730c, an API information selection element 3730d, and an application store selection element 3730e. Health information processing system 202 selection element 3730a allows analytics developer 214 to access, add, or modify information related to data exchanged with or analysis by health information processing system 202. Patient data selection element 3730b allows analytics developer 214 to access, add, or modify information related to patient data that patient 208 has authorized to be shared with analytics developer 214 or grouped data processed or analyzed by health information processing system 202. Third party review selection element 3730c allows analytics developer 214 to access, add, or modify information related to third party review of health applications. Third parties may be, for example, regulatory agencies or testing and validation entities. An API information selection element 3730d allows analytics developer 214 to access, add, or modify information and instructions related to application programming interface (API) instructions and information of health information processing system 202 for health application development by analytics developer 214. Selecting application data selection element 3730d is described below in conjunction with FIG. 38. Application store selection element 3730e allows analytics developer 214 to access, add, or modify information related to an application store that may be an ecommerce website operated by analytics developer 214 or a third party. Selection of application store selection element 3730e allows analytics developer 214 to place a new or modified health application for availability for download by patient 208, remove or alter health applications that are currently available, or post announcements on the health application store.

Figure 38:
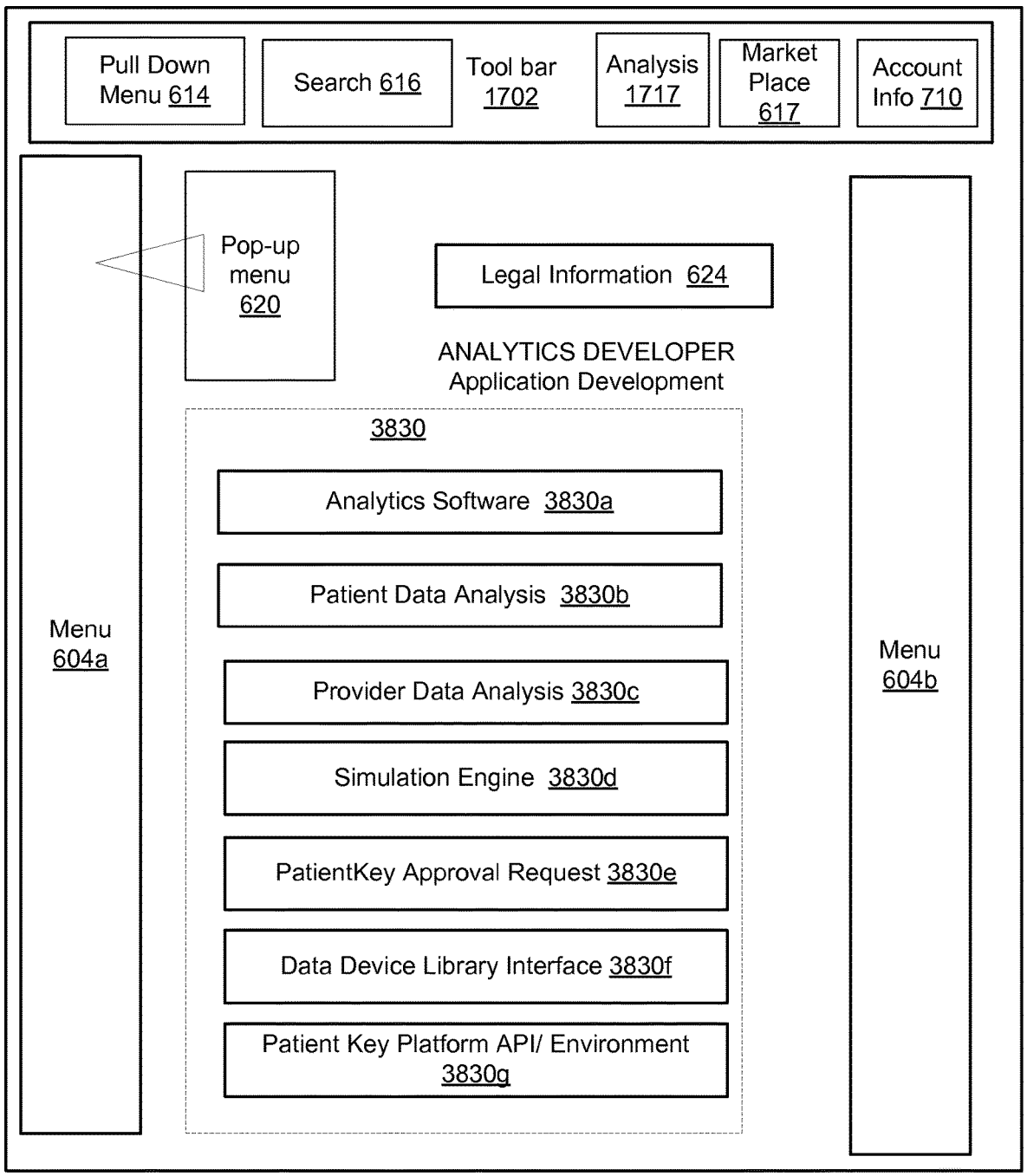
FIG. 38 illustrates a screenshot for application development by an analytics developer in the process of FIG. 35.

FIG. 38 illustrates a screenshot 3800, which may be generated in response to selection of application data selection element 3730d (FIG. 37), for application development by analytics developer 214 in the process of FIG. 35. Screenshot 3800 comprises a tool bar 1702, a plurality of menus 604a and 604b, a legal information selection element 624, and an application development menu 3830.

Application development menu 3830 comprises an analytics software selection element 3830a, a patient data analysis selection element 3830b, a provider data analysis selection element 3830c, a simulation engine selection element 3830d, an information processing system 202 approval selection element 3830e, a data device library interface selection element 3830f, and a health information processing system 202 platform selection element 3830g. Analytics software selection element 3830a allows analytics developer 214 to access, add, modify, or analyze information related to analytics software that analytics developers 214 has or is developing for health applications for health data sources 227. Patient data selection element 3830b allows analytics developer 214 to access, add, or modify information related to patient 208 related to health applications of analytics developer 214 for which patient 208 has authorized access by analytics developer 214. Provider data analysis selection element 3830c allows analytics developer 214 to access, add modify, or analyze information related to provider 204 related to health applications of analytics developer 214 for which provider 204 has authorized access by analytics developer 214. Simulation engine s selection element 3830d allows analytics developer 214 to access, add, or modify information related to a simulation engine that tests and evaluates health applications under development or developed by analytics developer 214 using data from health information processing system 202. Information processing system 202 approval selection element 3830e allows analytics developer 214 to access, add, or modify information related to requests by analytics developer 214 for approval of a new or modified health application by health information processing system 202. Data device library interface selection element 3830f allows analytics developer 214 to access, add, or modify information related to an interface for a library of the data device. Health information processing system 202 platform selection element 3830g allows analytics developer 214 to access, add, or modify information related to a platform API and environment for health information processing system 202.

Figure 39:
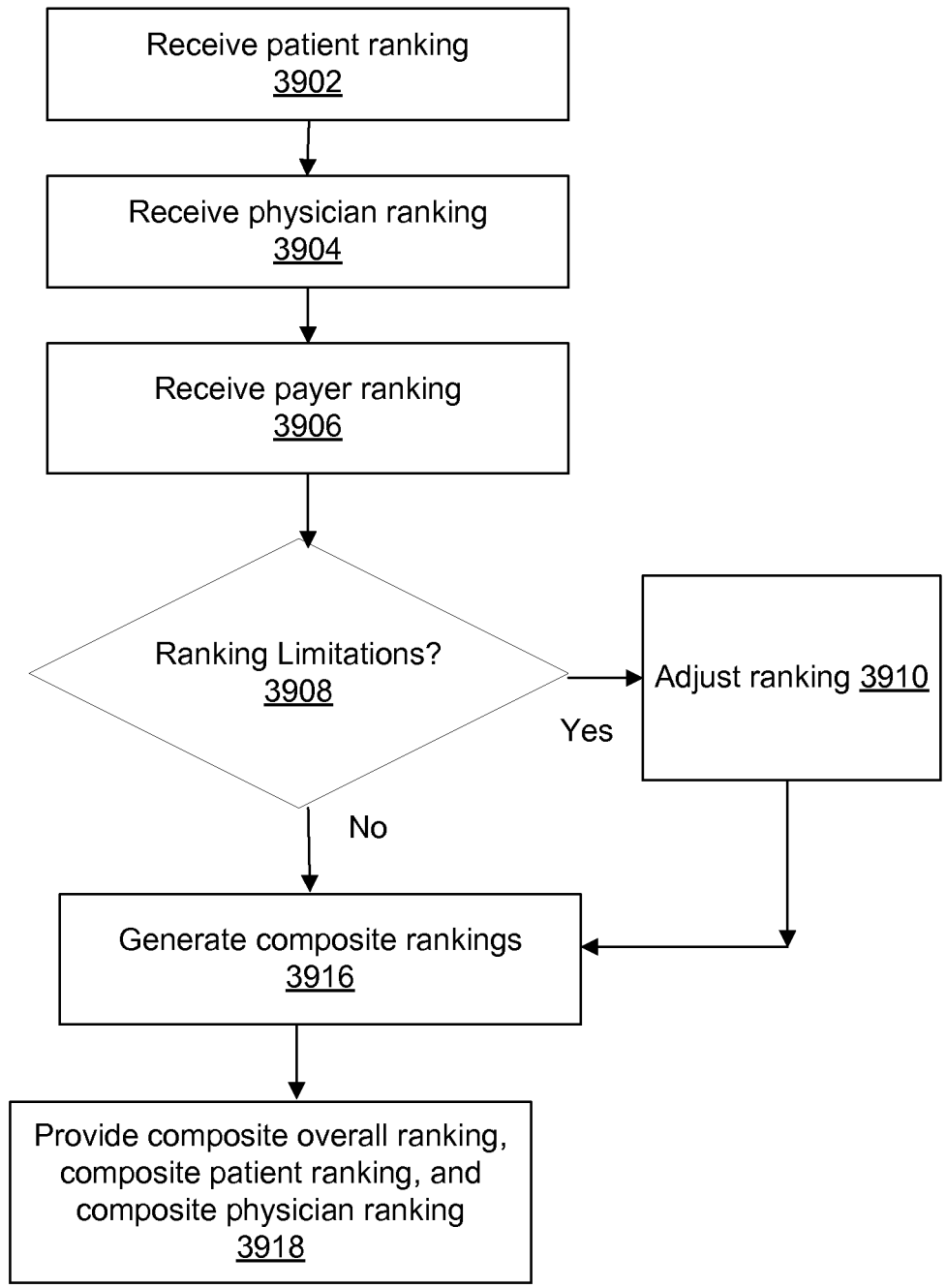
FIG. 39 illustrates a process for a ranking engine of the health information processing system of FIG. 3.

FIG. 39 illustrates a process for ranking engine 310. At 3902, ranking engine 310 receives a patient ranking for a provider 204, a health application, or a health data source 227, such as provided at 534 (FIG. 5) or a selection from screenshot 1400 (FIG. 14). At 3904, ranking engine 310 receives a provider ranking for a health application or a health data source 227, such as provided at 1526 (FIG. 15) or a selection from screenshot 2200 (FIG. 22). At 3906, ranking engine 310 receives a payer ranking for a health application or a health data source 227, such as provided from a selection from screenshot 2800 (FIG. 28). At 3908, ranking engine 310 determines whether the ranking from patient 208, provider 204, or payer 206 is to be limited. The limitation may be based on usage of a health application or health data source 227, other medical conditions of patient 208, If the ranking is to be limited at 3908, ranking engine 310, at 3910, executes the process of FIG. 40 for patient 208 or the process of FIG. 41 for provider 204 or payer 206.

If the ranking is not limited at 3908 or after the ranking has been limited at 3910, ranking engine 310 at 3916, determines a composite ranking based on the ranking of patient 208, provider 204, and payer 206. At 3918, ranking engine 310 provides the composite overall ranking, composite patent ranking, composite physician ranking and composite payer rankings to patient 208, payer 206 and provider 204.

Figure 40:
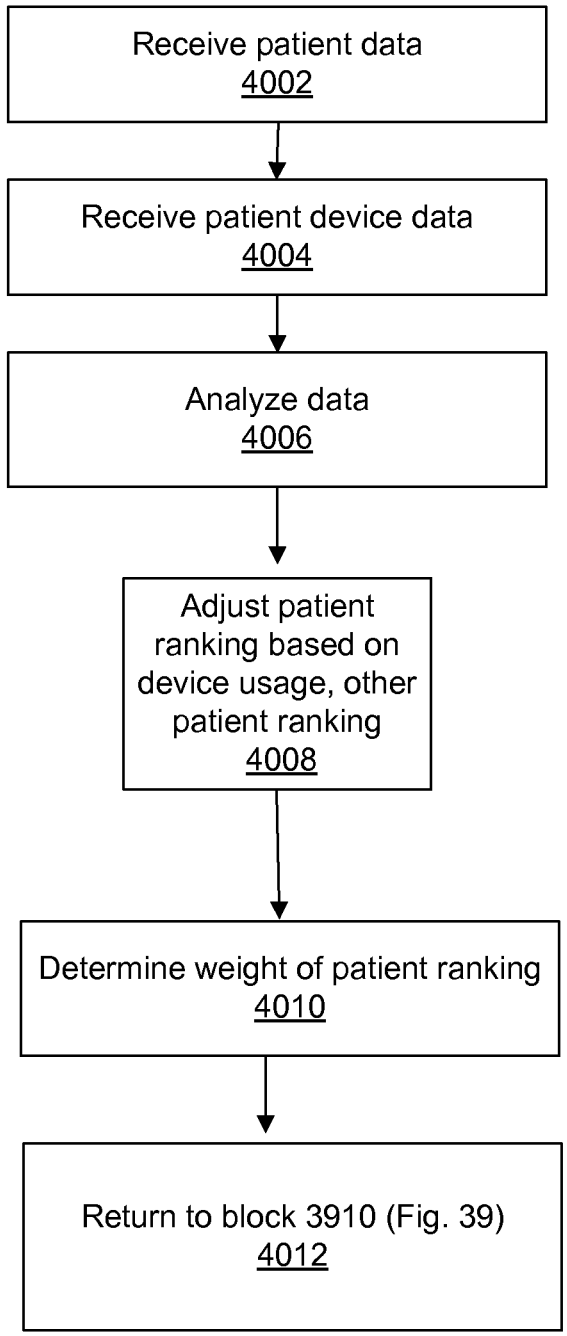
FIG. 40 illustrates a process for adjusting a ranking of a patient for the process of FIG. 39.

FIG. 40 illustrates a process for adjusting a ranking of patient 208 for the process of FIG. 39. At 4002, ranking engine 310 receives patient data from data store 330. At 4004, ranking engine 310 receives patient device data from data store 330. At 4006, ranking engine 310 analyzes the patient data and patient device data to determine whether rankings should be adjusted or limited. At 4008, ranking engine 310 adjusts the patient ranking based on various factors, such as device usage, patient medical history, patient past history of rankings, and other patient rankings At 4010, ranking engine 310 determines a weight of the patient ranking for use in the composite overall ranking and overall patient ranking. At 4012, ranking engine 310 returns to block 3910 of FIG. 39.

Figure 41:
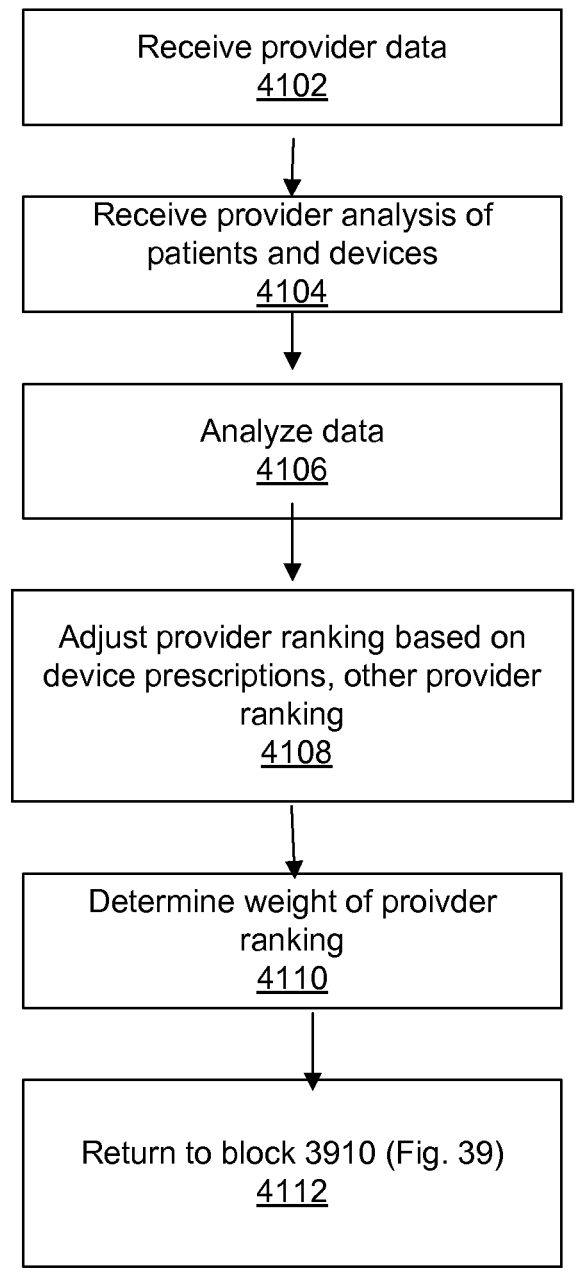
FIG. 41 illustrates a process for adjusting a ranking of a provider for the process of FIG. 39.

FIG. 41 illustrates a process for adjusting a ranking of provider 204 or payer 206 for the process of FIG. 39. Although the process of FIG. 41 applies for both provider 204 or payer 206, the process will be described only for provider 204. At 4102, ranking engine 310 receives provider data from data store 330. At 4104, ranking engine 310 receives providers analysis of patients and devices from data store 330 At 4106, ranking engine 310 analyzes the provider data and provider analysis to determine whether rankings should be adjusted or limited. At 4108, ranking engine 310 adjusts the provider ranking based on various factors, such as device prescriptions, and other provider rankings. At 4110, ranking engine 310 determines a weight of the provider ranking for use in the composite overall ranking and overall provider ranking. At 4112, ranking engine 310 returns to block 3910 of FIG. 39.

Figure 42:
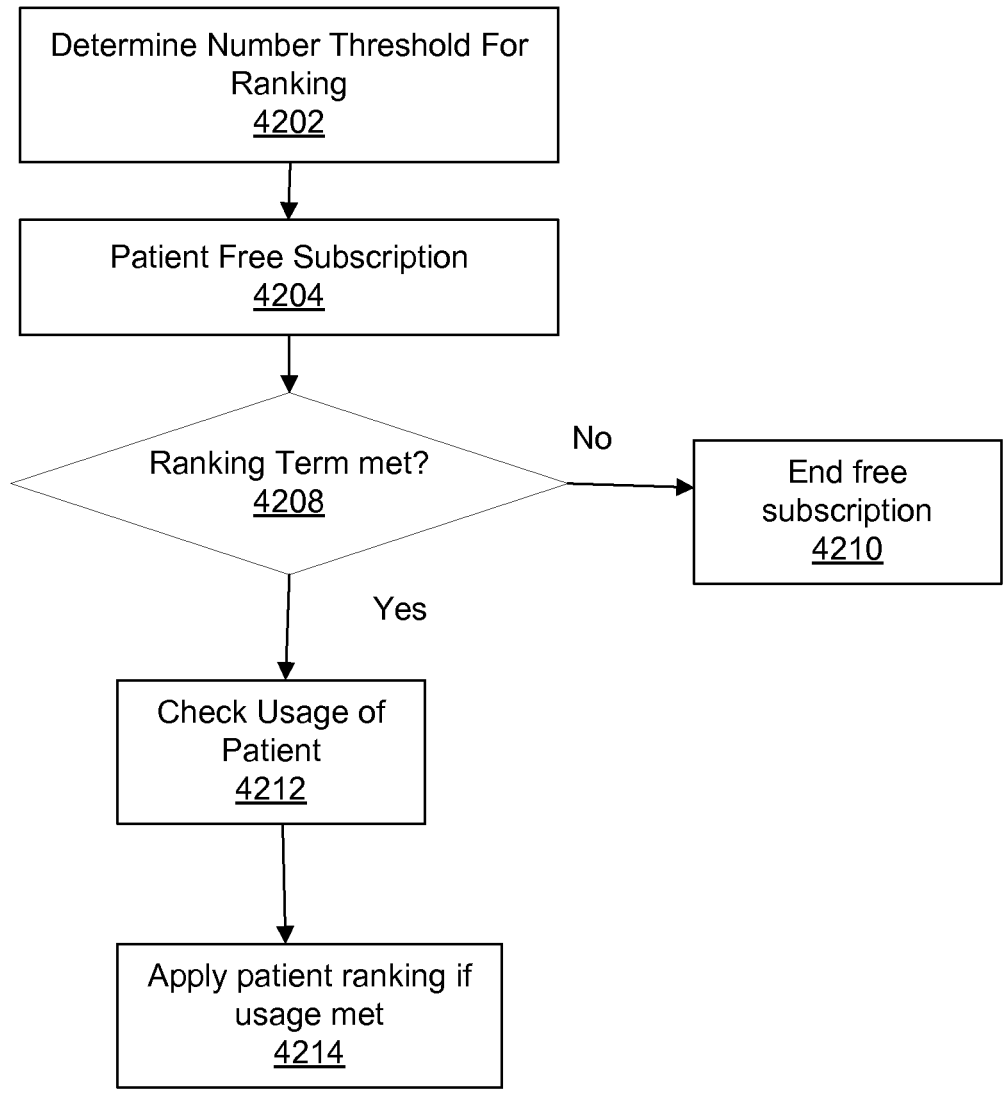
FIG. 42 illustrates a process for a ranking engine of the health information processing system of FIG. 3 for ranking a new health application or health data source.

FIG. 42 illustrates a process for processing rankings for a new health application or health data source 227 by ranking engine 310. At 4202, ranking engine 310 determines a threshold or thresholds for the number or numbers of system users 201 before ranking engine 310 generates a composite ranking or displays rankings of system users 201. For example, the threshold may be a number X of patients 208 that must rank a new health application or health data source 227 before ranking engine 310 generates a composite ranking of the new health application or health data source 227 by patients 208. Further, the threshold may be a number Y of physicians 222 that must rank a new health application or health data source 227 before ranking engine 310 generates a composite ranking of the new health application or health data source 227 by physicians 222. Yet further, both the threshold X of patients 208 and the threshold Y of physicians 222 must be met before ranking engine 310 generates a composite ranking of the new health application or health data source 227. For the sake of illustration, the process of FIG. 42 is described for a patient 208, but the process applies for other system users 201.

In various embodiments, patient 208 is provided with an incentive to use and evaluate a new health application or health data source 227. For example, the incentive may be that patient 208 gets a free subscription or license to use the new health application or health data source 227 for a limited time (e.g., six months), if patient 208 ranks the new health application or health data source 227 before the expiration of the limited time (e.g., before four months). At 4204, patient 208 receives a free subscription or license to use the new health application or health data source 227. At 4208, ranking engine 310 determines whether a patient ranking is received, such as provided at 534 (FIG. 5) within the ranking term. If the ranking is not received within the ranking term at 4208, ranking engine 310 terminates, at 4210, the free subscription of patient 208.

If the ranking is received within the ranking term at 4208, ranking engine 310 check, at 4212, the usage of the new health application or health data source 227 by the patient 208. If the usage is sufficient, ranking engine 310 accepts, at 4214, the patient ranking and stores the ranking in ranking data 410. The evaluation of the usage by patient 208 determines whether patient 208 is a regular user of the new health application or health data source 227 to avoid fake rankings by family or friends. In some embodiments, ranking engine 310 may allow patient 208 a limited number (e.g., one) opportunity to submit a ranking for evaluation. In some embodiments, ranking engine 310 may terminate the subscription if the ranking is rejected.

Figure 43:
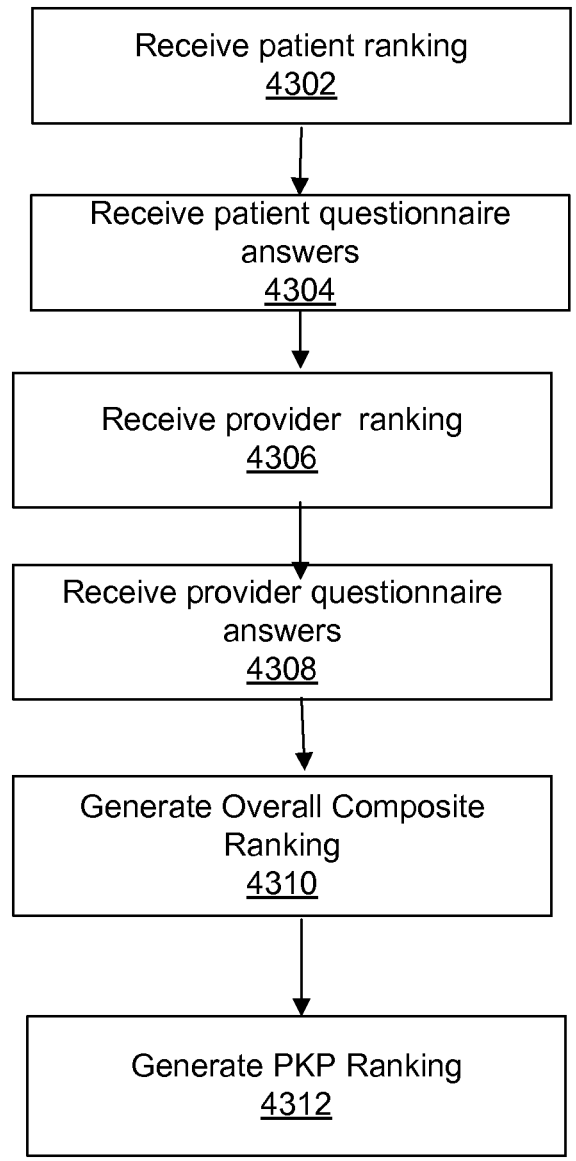
FIG. 43 illustrates a process for a ranking engine of the health information processing system of FIG. 3 for generating composite overall rankings for a health application or health data source.

FIG. 43 illustrates a process for generating composite overall rankings for a health application or health data source 227 by ranking engine 310.

At 4302, ranking engine 310 receives a patient ranking from patient 208 for a health application or a health data source 227, such as provided at 534 (FIG. 5) or a selection from screenshot 1400 (FIG. 14). At 4304, ranking engine 310 generates and provides a questionnaire to patient 208 for patient 208 to provide a rationale for the ranking, and receives answers from patient 208.

At 4306, ranking engine 310 receives a provider ranking from provider 204 for a health application or a health data source 227, such as provided at 1526 (FIG. 15) or a selection from screenshot 2200 (FIG. 22). At 4308, ranking engine 310 generates and provides a questionnaire to provider 204 for provider 204 to provide a rationale for the ranking, and receives answers from provider 204.

At 4310, ranking engine 310 generates a composite patient ranking from rankings from patients 208, a composite provider ranking from rankings from providers 204, and an overall composite ranking from rankings from patients 208 and rankings from providers 204.

At 4312, ranking engine 310 generates a system overall ranking (referred to as "PKP ranking" in FIG. 45, described below) from the patient ranking at 4302, the questionnaire at 4304, the provider ranking at 4306, the questionnaire at 4308.

Figure 44:
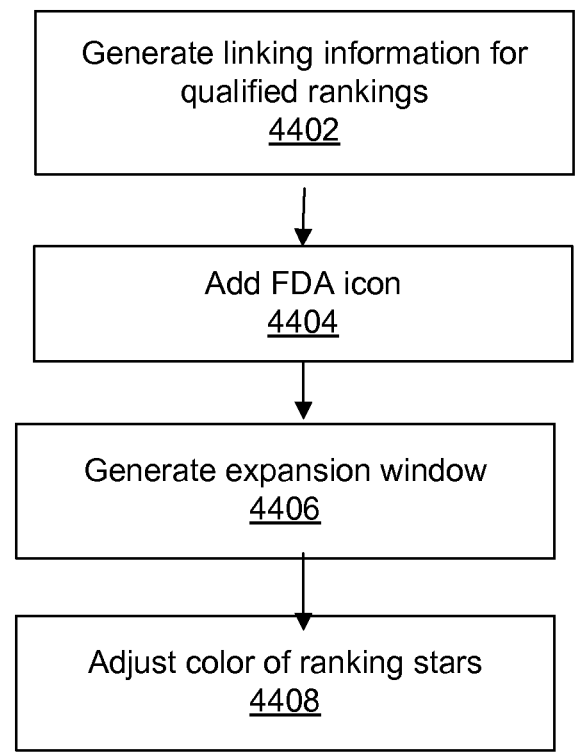
FIG. 44 illustrates a process for generating display information for screenshots of ranking information.

FIG. 44 illustrates a process for generating display information for screenshots of ranking information. The process of FIG. 44 is described in conjunction with the screenshot of FIG. 45, which illustrates a screenshot for rankings of a health data source 227. As an illustrative example, a health data source 227 is described. The display information for a ranking may be included in any screenshot that shows the health application or health data source 227 corresponding to the ranking.

At 4402, ranking engine 310 generates an icon or popup that includes the name of a provider 204 that has ranked a health application or health data source 227, and may include a link to a profile of that provider 204, if the provider 204 has ranked the health data source 227 above a threshold (e.g., four stars in a five star ranking system, with five stars being highest). One such example is link 4502 (FIG. 45) for "Dr. Amy James" who gave a five star ranking to health data source 227.

At 4404, ranking engine 310 generates an icon to indicate that health data source 227 is approved by an entity. For example, health data source 227 may be approved by the Food and Drug Administration (FDA). One such example is icon 4504 (FIG. 45) for an FDA icon.

At 4406, ranking engine 310 may generate an expansion or pop up window to expand on the rankings that are displayed. For example, the rankings may be the composite patient ranking from rankings from patients 208, the composite provider ranking from rankings from providers 204, and that overall composite ranking from rankings from patients 208 and rankings from providers 204 generated at 4310 (FIG. 43). The expansion may also provide quantitative information about the rankings, such as number of patients 208 providing rankings and number of providers 204 providing rankings. The quantitative information may be displayed with the ranking information. One such example is expansion 4506 (FIG. 45) that shows that 1,135 patients 208 and 3 providers 204 ranked the device.

At 4408, ranking engine 310 adjusts the color of the ranking indicators. For example, if a number N of patients 208 ranked an application is more than a threshold "A1", ranking engine 310 sets the ranking stars to be a color C1. If the number N is more than the threshold A1, but less than a second threshold "A2", ranking engine 310 sets the ranking stars to be a color C2. If the number N is more than the threshold A2, ranking engine 310 sets the ranking stars to be a color C3.

Figure 46:
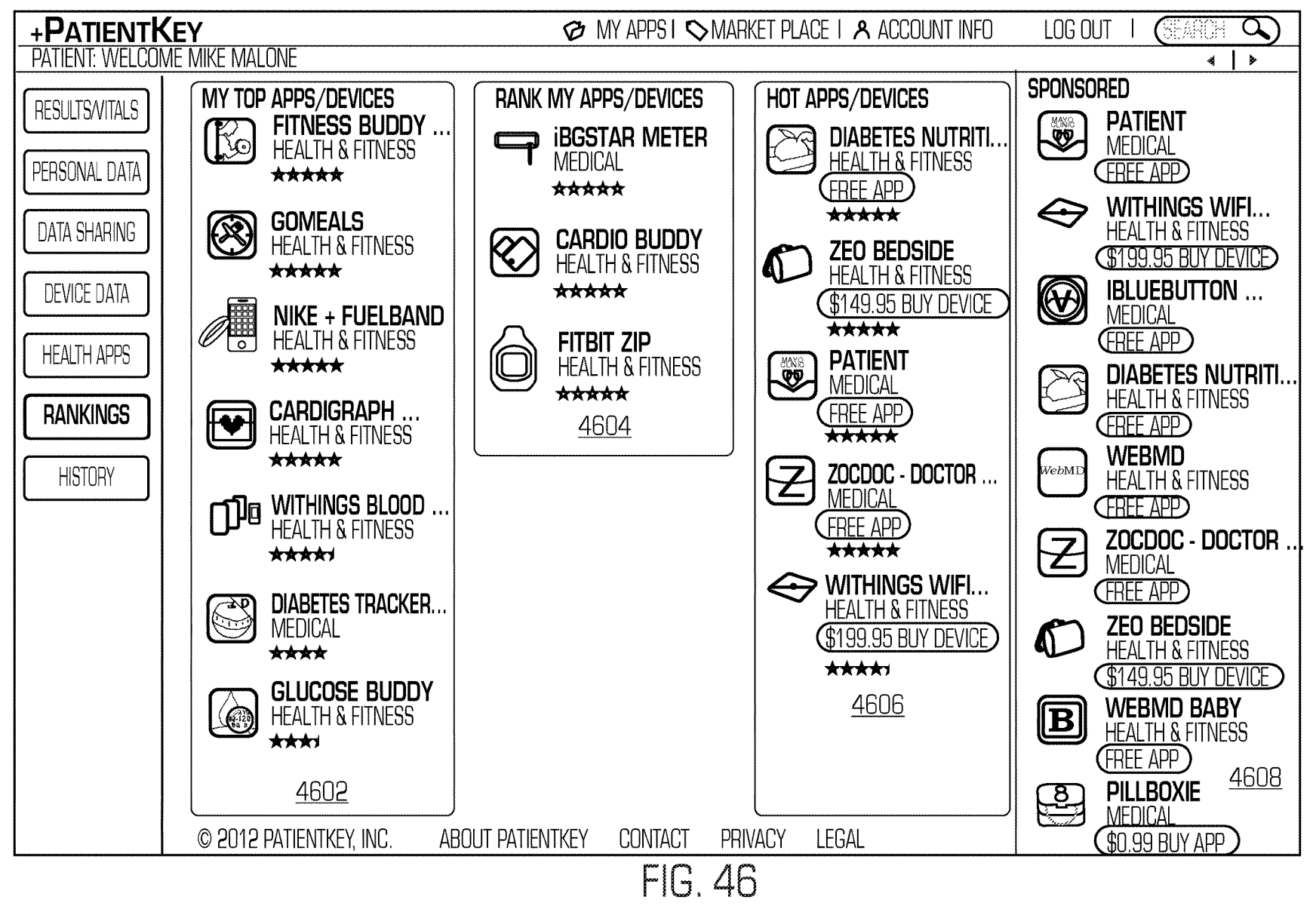

FIG. 46 illustrates a screenshot for ranking health applications and health data sources 227 of patient 208. FIG. 46 is an illustrative embodiment of the screenshot of FIG. 14. The screenshot includes a region 4602 that displays all or the top health applications and health data sources 227 that patient 208 has. The screenshot also includes a region 4604 that displays the health applications and health data sources 227 that patient 208 has not ranked. The region 4604 may also include a time indication left for new health applications and health data sources 227 that have free subscriptions that impose a time limit, such as those described above in conjunction with FIG. 42. The screenshot also includes a region 4606 that displays health applications and health data sources 227 that are "hot," such as most popular, recently reviewed in the media, trade journals, or by trade associations, recently approved by a regulatory agency or insurance company, positive trend in rankings, or the like. The screenshot further includes a region 4608 that displays advertising for health applications and health data sources 227.

Figure 47:
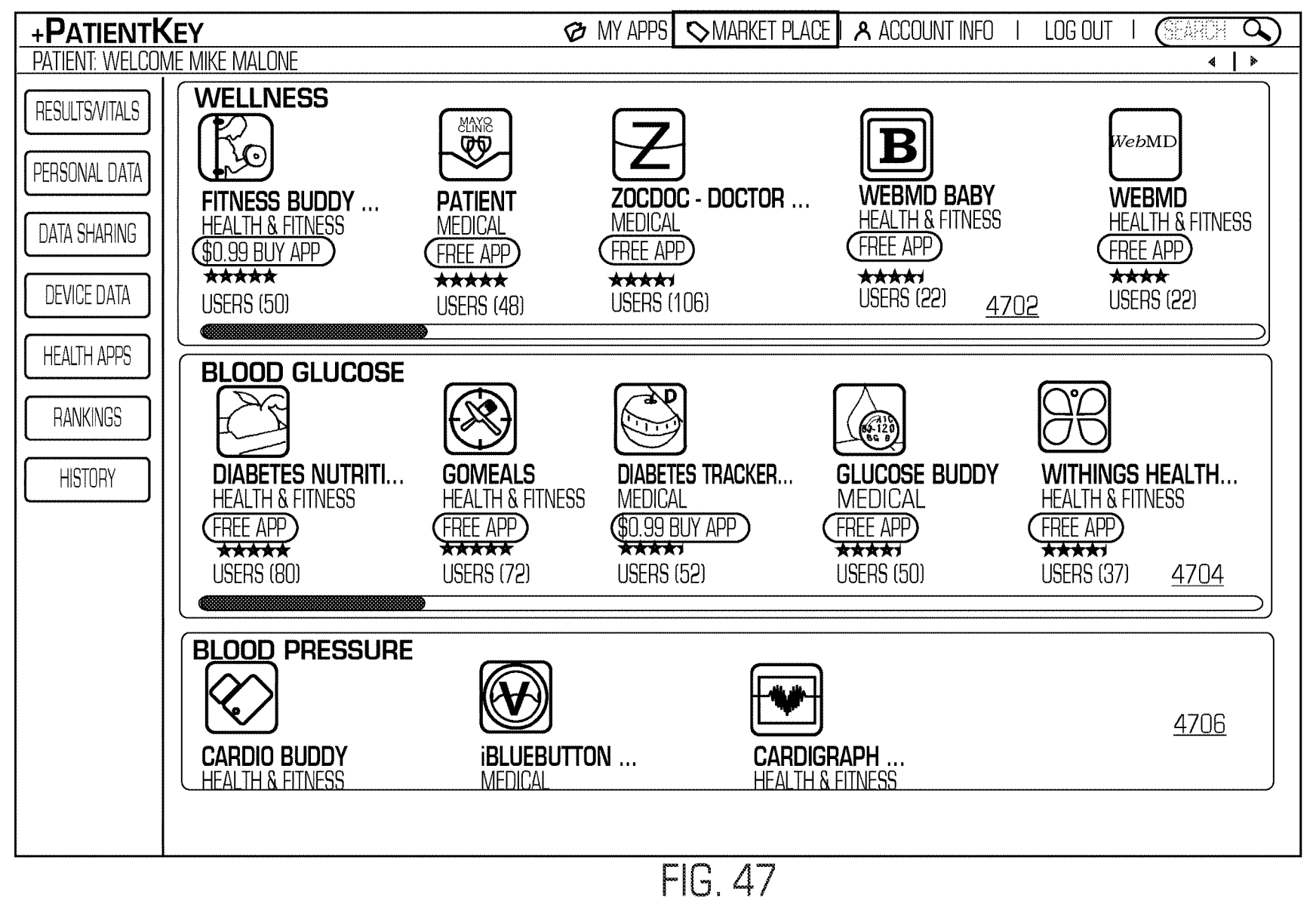

FIG. 47 illustrates a screenshot for health applications available to patient 208 in the marketplace. The screenshot of FIG. 47 may be displayed in response to the selection of the marketplace icon in FIGS. 6-14 by patient 208 or selection of search health applications selection element 1130e (FIG. 11). The screenshot may display health applications based on health data sources 227 that patient 208 has, are prescribed or recommended by physician 222, determined as being of interest based on searches by patient 208, In various embodiments, the screenshot includes health applications arranged by health categories. The screenshot includes a region 4702, a region 4704, and a region 4706 that display health applications for wellness, blood glucose, and blood pressure, respectively.

FIG. 48 illustrates a screenshot for a health data source 227 that physician 222 can evaluate for recommending or prescribing patients 208. The screenshot of FIG. 48 may be displayed in response to the selection of the marketplace icon in FIGS. 16-23 by physician 222 or other provider 204 or selection of search devices selection element 1930c (FIG. 19). As an illustrative example, the screenshot shows a glucose device with descriptive text and technical specifications.

FIG. 49 illustrates a screenshot for a health data source 227 that patient 208 can evaluate for purchase. The screenshot of FIG. 49 may be displayed in response to the selection of the marketplace icon in FIGS. 6-14 by patient 208, data device search selection element 1030e (FIG. 10), or a selection element of FIG. 47. As an illustrative example, the screenshot shows a glucose device with descriptive text and technical specifications.

Figure 50:
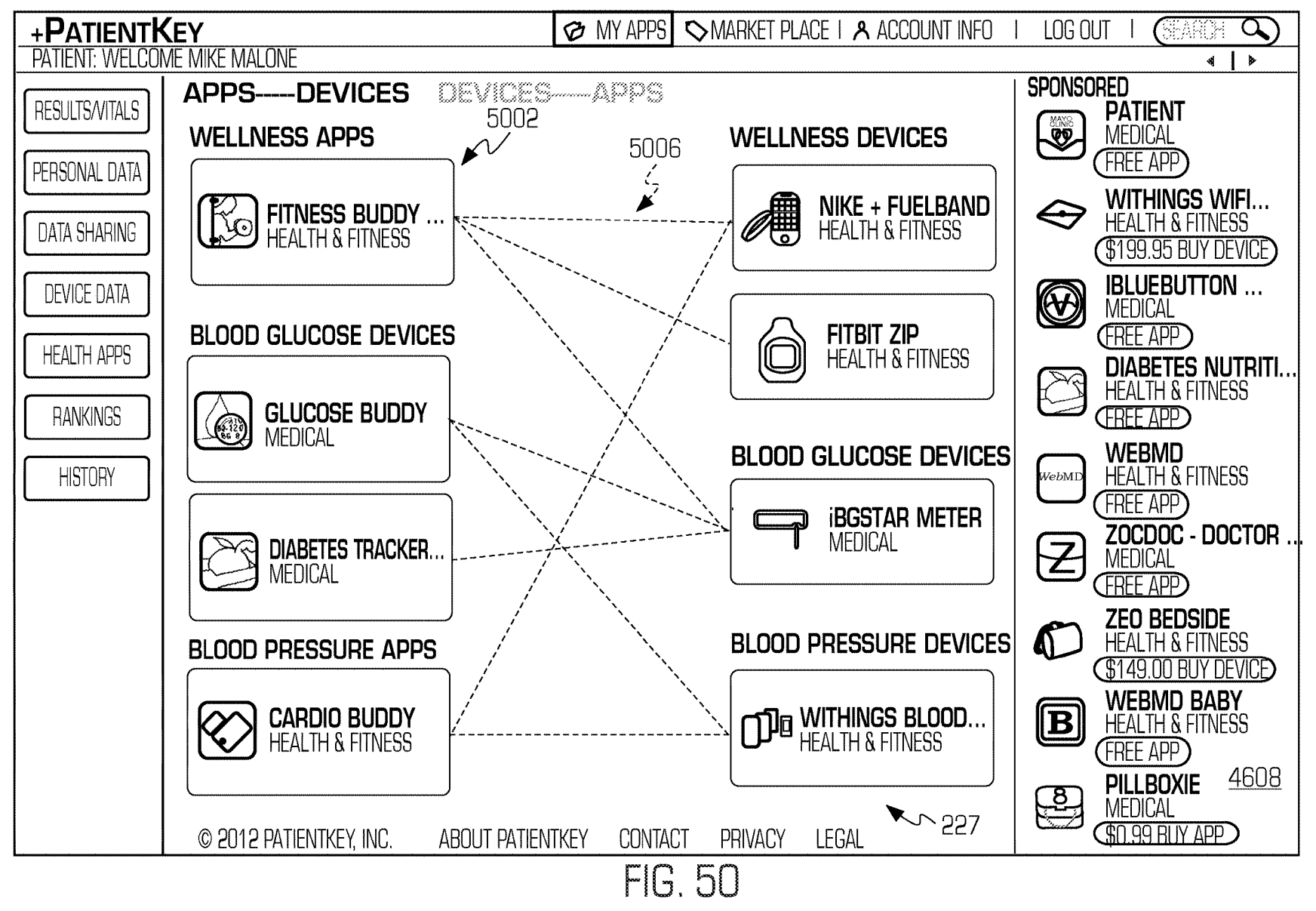

FIG. 50 illustrates a screenshot of consolidation of health applications and health data sources 227 of patient 208. The screenshot of FIG. 50 may be displayed, for example, in response to the selection of results/vitals selection element 730h (FIG. 7) or one of the results selection elements 1230 (FIG. 12). The screenshot includes a plurality of health applications 5002 that patient 208 has. As an illustrative example, patient 208 has one wellness health application 5002, two blood glucose health applications 5002, and one blood pressure health application 5002. The screenshot also includes a plurality of health data sources 227 that patient 208 has. As an illustrative example, patient 208 has two wellness health data sources 227, one blood glucose health data source 227, and one blood pressure health data source 227.

Links 5006 connect health applications 5002 to associated health data sources 227. One health application 5002 may be connected to one or more health data sources 227 by one or more links 5006. A fitness health application is linked to two wellness devices and a blood glucose meter. Associations are described more generally below in conjunctions with FIG. 52. One health data source 227 may be connected to one or more health applications 5007 by one or more links 5006. Associations are described more generally below in conjunctions with FIG. 53. By linking health applications and health data sources 227, patient 208 may consolidate health data so that the patient may display data from related or linked devices and health applications, such as wellness data from fitness devices and blood glucose devices. Similarly, blood glucose information may be displayed with exercise, diet, and blood glucose device measurements. The links 5006 may be displayed with visible variations to indicate characteristics or correlations between health applications 5002, health data sources 227 and characteristics of patients, such as patient's usage or adherence, or refresh rate, synchronization rate and the like of the health applications with health information processing system 202. The visible variations may be, for example, different colors of lines, different types of lines (such as dotted lines), different line thickness, and different line density. Another example of consolidated data is shown in FIG. 51

Figure 51:
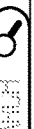
FIG. 51 illustrates a screenshot of consolidated data of medications.

FIG. 51 illustrates a screenshot 5100 of consolidated data for medications. Screenshot 5100 may be displayed, for example, in response to the selection of results/vitals selection element 730h (FIG. 7) or one of the results selection elements 1230 (FIG. 12). Screenshot 5100 illustrates the reading of a health data source 227, such as a pillbox, that detects when patient 208 takes medication. In an illustrative example, screenshot 5100 shows that patient 208 takes two medications, namely Coreg and Sulfonylureas, the compliance with the medications times for the past two days, and a compliance rate. Screenshot 5100 also consolidates data from a health data source 227 that detects cardio activity and displays associated data.

Figure 52:
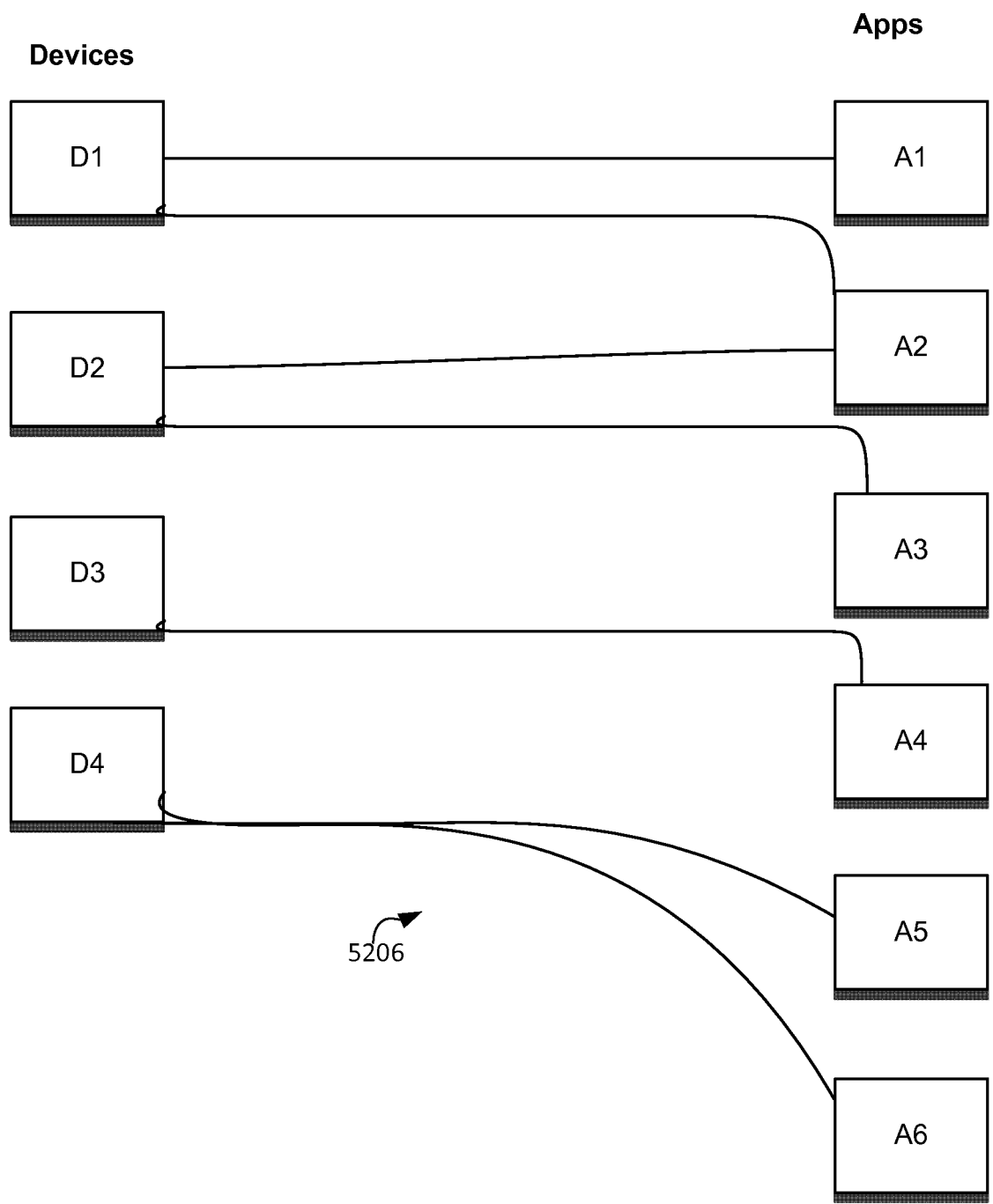
FIG. 52 illustrates a block diagram of associations between health data sources and one or more health applications as one embodiment of the consolidation of FIG. 50.

FIG. 52 illustrates a block diagram of associations between health data sources 227 and one or more health applications. In an illustrative embodiment, health data sources 227 are labeled D1 through D4, and health applications are labeled A1 through A6. Device D1 is linked to multiple health applications, namely applications A1 and A2. Likewise, device D1 is linked to multiple health applications, namely applications A2 and A3, and device D4 is linked to multiple health applications, namely applications A5 and A6. However, device D3 is linked to a single health application, namely application A4. Links 5206 between, health data sources 227 (labeled D1 through D4), and health applications (labeled A1 through A6) may be displayed with visible variations in a similar manner as links 5006 described above.

Figure 53:
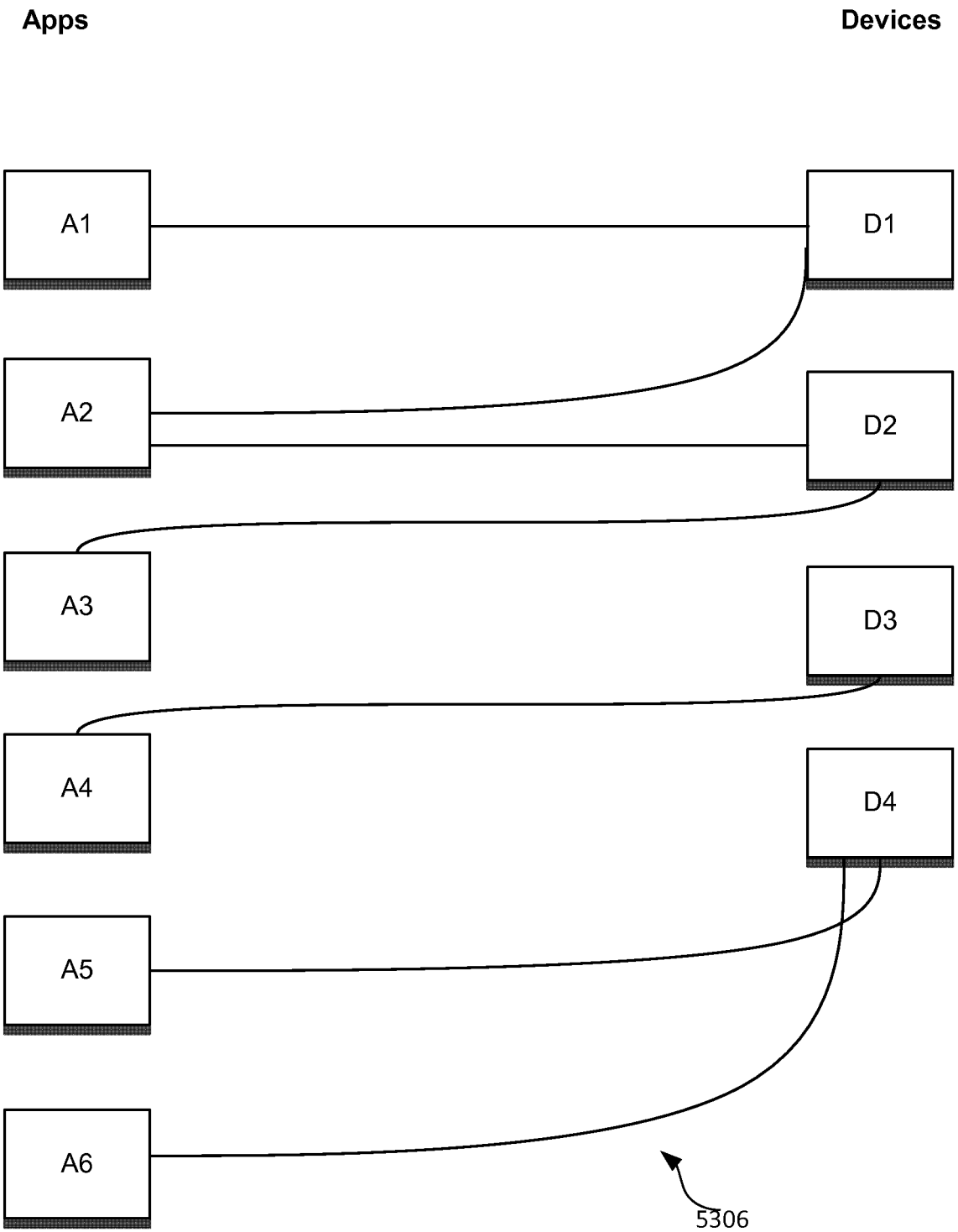
FIG. 53 illustrates a block diagram of associations between health applications and one or more health data sources of the consolidation of FIG. 50.

FIG. 53 illustrates a block diagram of associations between health applications and one or more health data sources 277. In an illustrative embodiment, health data sources 227 are labeled D1 through D4, and health applications are labeled A1 through A6. Application A1 is linked to a single device, namely D1. Application A2 is linked to multiple devices, namely D1 and D2. Application A3 is linked to a single device, namely DD. Application A4 is linked to a single device, namely D3. Application A5 is linked to a single device, namely D4. Application A6 is linked to a single device, namely D4. Links 5306 between, health data sources 227 (labeled D1 through D4), and health applications (labeled A1 through A6) may be displayed with visible variations in a similar manner as links 5006 described above.

Figure 54:
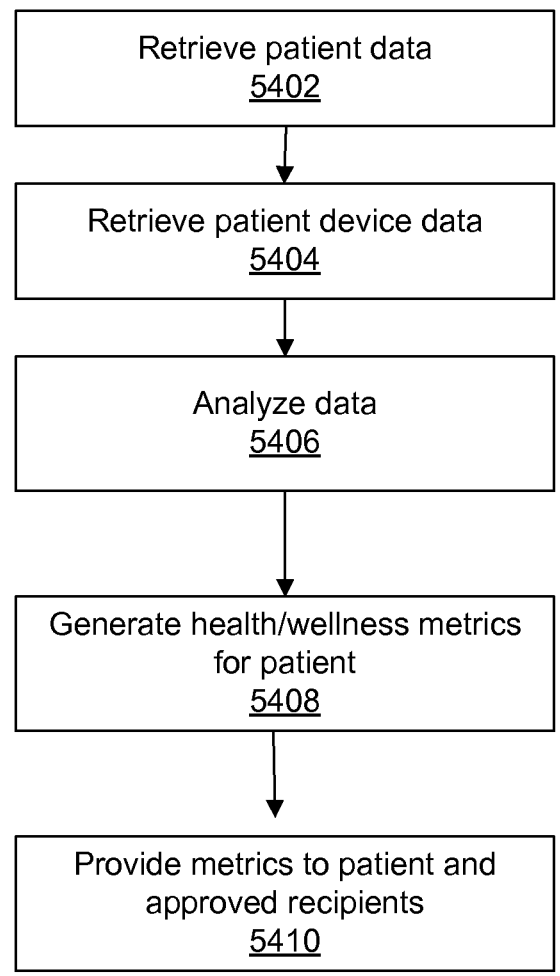
FIG. 54 illustrates a process for generating health or wellness metrics by the health data processing system of FIG. 2.

FIG. 54 illustrates a process for generating health or wellness metrics by health information processing system 202. At 5402, ranking engine 310 retrieves patient data from data store 330. At 5404, ranking engine 310 retrieves patient device data from data store 330. At 5406, ranking engine 310 analyzes the retrieved data, and generates, at 5408, health and wellness metrics for patient 208. At 5410, user application engine 320 provides the metrics to patient 208 and approved recipients. Data analytics engine 312 may analyze the metrics to determine whether patient 208 has indication or has a chronic condition. For example, data analytics engine 312 may monitor blood sugar level on a first health data source 227 of patient 208, and may determine that patient 208 has indications of diabetes. Data analytics engine 312 may also monitor weight of patient 208 from a second health data source 227 of patient 208, and based on an analysis of both blood sugar and weight, determine that patient 208 is showing signs of diabetes.

Figure 55:
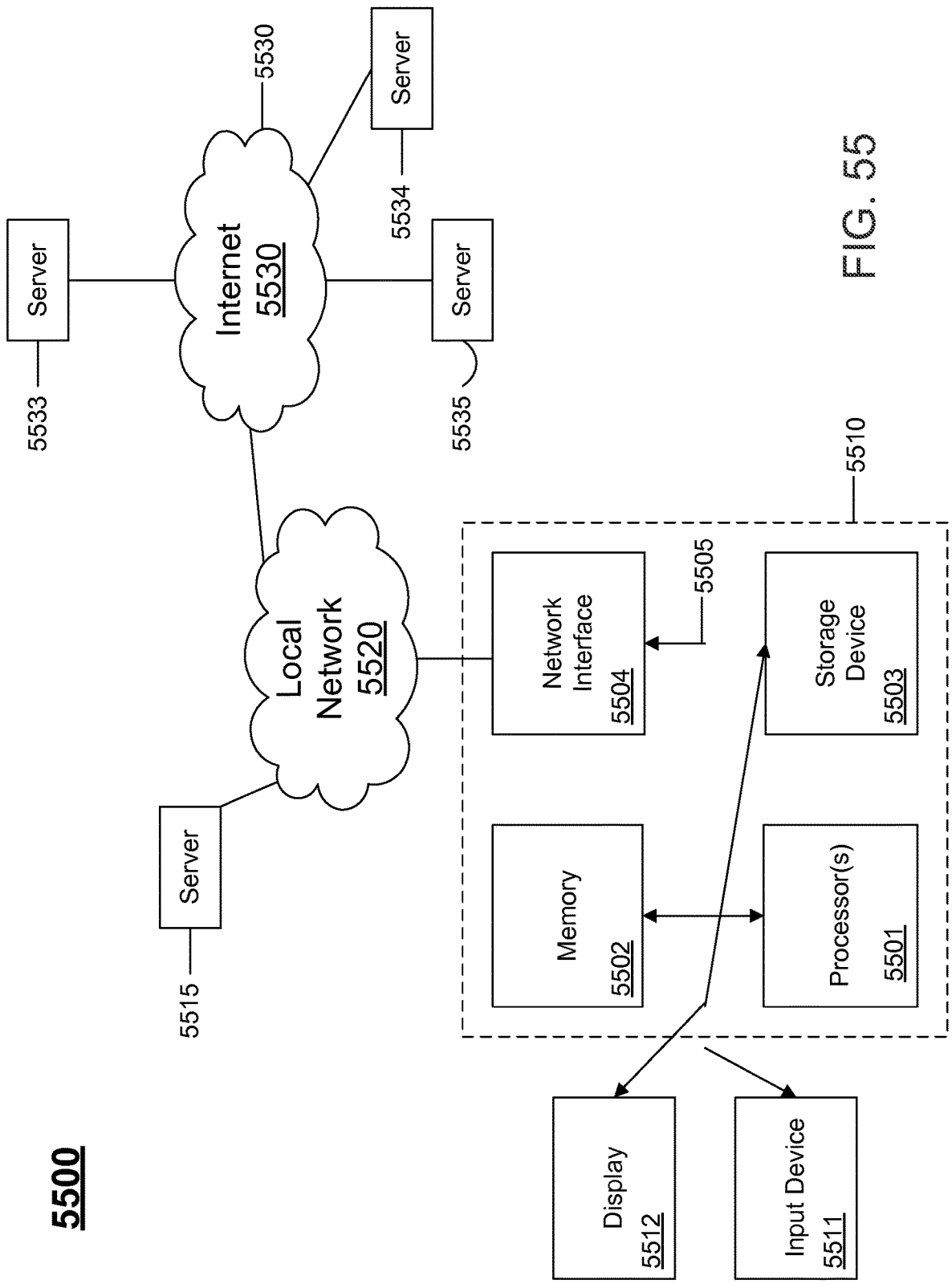
FIG. 55 illustrates hardware used to implement embodiments of the health data processing system of FIG. 2.

FIG. 55 illustrates hardware used to implement embodiments of health data processing system 200. An example computer system 5510 is illustrated in FIG. 55. Computer system 5510 includes a bus 5505 or other communication mechanism for communicating information, and one or more processors 5501 coupled with bus 5505 for processing information. Computer system 5510 also includes a memory 5502 coupled to bus 5505 for storing information and instructions to be executed by processor 5501, including information and instructions for performing the techniques described above, for example. This memory may also be used for storing variables or other intermediate information during execution of instructions to be executed by processor 5501. Possible implementations of this memory may be, but are not limited to, random access memory (RAM), read only memory (ROM), or both. A machine readable storage device 5503 is also provided for storing information and instructions. Common forms of storage devices include, for example, a non-transitory electromagnetic medium such as a hard drive, a magnetic disk, an optical disk, a CD-ROM, a DVD, Blu-Ray, a flash memory, a USB memory card, or any other medium from which a computer can read. Storage device 5503 may include source code, binary code, or software files for performing the techniques above, for example. Storage device 5503 and memory 5502 are both examples of computer readable mediums.

Computer system 5510 may be coupled via bus 5505 to a display 5512, such as a cathode ray tube (CRT), plasma display, light emitting diode (LED) display, LED-backlit multi-touch display with in-plane switching (IPS) technology, or liquid crystal display (LCD), for displaying information to a computer user. An input device 5511 such as a keyboard, mouse and/or touch screen is coupled to bus 5505 for communicating information and command selections from the user to processor 5501. The combination of these components allows the user to communicate with the system, and may include, for example, user interface 105. In some systems, bus 5505 may be divided into multiple specialized buses. Each system user 201 interfaces with an input device 5511 and a display 5512.

Computer system 5510 also includes a network interface 5504 coupled with bus 5505. Network interface 5504 may provide two-way data communication between computer system 5510 and the local network 5520, for example. The network interface 5504 may be a wireless network interface, a cable modem, a digital subscriber line (DSL) or a modem to provide data communication connection over a telephone line, for example. Another example of the network interface is a local area network (LAN) card to provide a data communication connection to a compatible LAN. Wireless links are another example. In any such implementation, network interface 5504 sends and receives electrical, electromagnetic, or optical signals that carry digital data streams representing various types of information.

Computer system 5510 can send and receive information, including messages or other interface actions, through the network interface 5504 across a local network 5520, an Intranet, or the Internet 5530. For a local network, computer system 5510 may communicate with a plurality of other computer machines, such as server 5515. Accordingly, computer system 5510 and server computer systems represented by server 5515 may be programmed with processes described herein. In the Internet example, software components or services may reside on multiple different computer systems 5510 or servers 5533-5535 across the network. Some or all of the processes described above may be implemented on one or more servers, for example. Specifically, health data processing system 200 or elements thereof might be located on different computer systems 5510 or one or more servers 5515 and 5533-5535, for example. A server 5533 may transmit actions or messages from one component, through Internet 5530, local network 5520, and network interface 5504 to a component on computer system 5510. The software components and processes described above may be implemented on any computer system and send and/or receive information across a network, for example.

FIG. 56 illustrates a screenshot 5600 of patients 208 of physician 222. Screenshot 5600 may be displayed, for example, in response to the selection of analysis icon 1717 (FIGS. 17-23) or patient data selection element 2130a (FIG. 21). Screenshot 5600 comprises a "patients" icon 5602, a marketplace icon 5604, an account information icon 5606, and a log out icon 5608. The term "icon" is used interchangeably herein with the term "selection element."

Patients icon 5602 allows provider 204 to access, add, or modify information related to patients 208 of provider 204. Screenshot 5600 includes a priority list 5632 listing patients 208 that are in a first (or highest or top) priority level of medical care, such as patients 208 that are in emergency, in an ambulance or hospitalized. Screenshot 5600 further includes a watch list 5634 listing patients 208 that are in a second priority level of medical care, such as patients 208 that provider 204 monitors at some frequency. Screenshot 5600 further includes an alert list 5636 listing any patient 208 having results from health care device 227, health application, medical test, or medical evaluation that falls outside of a normal or patient-specific range. Screenshot 5600 further includes an others list 5638 that includes all patients 208 of provider 204 that are not any of lists 5632, 5634 or 5636. Selection of a patient 208, e.g., by clicking on the name or selecting a box and selecting, opens a screenshot associated with that patient 208. For example, in response to selecting a patient, health information processing system 202 may display the screenshot of FIG. 57 described below. Lists 5632, 5634, 5636, 5638 may include name, status (which may be changed from priority, watch, alert and other), adherence, next appointment (or last appointment with provider 204), and results/vitals of patient 208.

Marketplace icon 5604 allows provider 204 to access, add, or modify information related to the available health care devices 227 and health care applications including the ranking and number of users 201. In various embodiments, marketplace icon 5604 is similar to marketplace icon 617.

Account information icon 5606 allows provider 204 to access, add, or modify account information such as password, contact information (such as email address, physical address, or phone number) or user name. In various embodiments, account information icon 5606 is similar to account information selection element 710. Log out icon 5608 allows provider 204 to logout of health information processing system 202.

Screenshot 5600 further comprises a results/vitals icon 5612, a provider data icon 5614, a device data icon 5616, a health applications icon 5618, a prescriptions icon 5620, a rankings icon 5622, and an analytics icon 5624.

In response to selection of results/vitals icon 5612, health information processing system 202 generates a screenshot for provider 204 that displays a snapshot or summary of data from health data devices 227 and health applications of a patient 208 of provider 204. The screenshot may be, for example, the screenshot or a subset of the screenshot generated in response to selection of results/vitals selection element 730h, or may include further information generated by health information processing system 202.

Provider data icon 5614 allows provider 204 to access, add, or modify information related to provider data, such as provider name, contact information, specialty, medical group, and the like, for provider 204.

Device data icon 5616 allows provider 204 to access, add, or modify information related to health care devices 227 recommended by provider 204 and used by patients 208 of provider 204, rankings, number of users, analysis by health information processing system 202 of the health care devices 227, and a search icon for provider 204 to search available health care devices 227 for a specific medical condition. The analysis by health information processing system 202 may provide overall effectiveness of health care device 227 and patient satisfaction with health care device 227. In various embodiments, device data icon 5616 is similar to data device selection element 1730b. In various embodiments, health information processing system 202 generates screenshot 1900 in response to selection of device data icon 5616.

Health applications icon 5618 allows provider 204 to access, add, or modify information related to health applications recommended by provider 204 and used by patients 208 of provider 204, rankings, number of users, analysis by health information processing system 202 of the health applications, and a search icon for provider 204 to search available health applications for a specific medical condition. The analysis by health information processing system 202 may provide overall effectiveness of health applications and patient satisfaction with health applications. In various embodiments, health applications icon 5618 is similar to health applications selection element 1730c. In various embodiments, health information processing system 202 generates screenshot 2000 in response to selection of health applications icon 5618.

Prescriptions icon 5620 allows provider 204 to access, add, or modify information related to prescribing health data sources 227 or health applications or bundles thereof to a particular patient 208 or groups of patients 208. In various embodiments, provider 204 recommends health data sources 227 or health applications or bundles thereof to a particular patient 208 or groups of patients 208 via email, short message service (SMS) text, phone call or the like based on patient profile (age, gender) or medical vitals (e.g., body mass index or blood pressure) or a specific medical condition.

Health information processing system 202 may provide a future patient 208 of this provider 204 with recommendations based on patient profiles, medical vitals, or specific medical condition in response to the future patient 208 connecting or linking to the provider 204.

In various embodiments, selection of prescriptions icon 5620 provides similar information in screenshots as selection of patient prescribing selection element 2130d and group based prescribing selection element 2130e.

Rankings icon 5622 allows provider 204 to access, add, or modify information related to ranking of health care devices 227, health applications, review health ranking history, or provider ranking by patients 208 of provider 204. In some embodiments, rankings icon 5622 is similar to rank selection element 1730e (FIG. 17). In various embodiments, health information processing system 202 displays screenshot 2200 (FIG. 22) in response to selection of rankings icon 5622.

Analytics icon 5624 allows provider 204 to access, add, or modify information related to analysis performed by health information processing system 202 that is accessible by provider 204. In various embodiments, provider 204 may compare patients 208, health data devices 227, and health applications based on various factors, such as results for same patient from different health applications or health data devices 227, adherence, or number of users. In various embodiments, the analytics are displayed pictorially in pie charts, bar charts, line charts, and the like.

In various embodiments, health information processing system 202 generates analytics of vitals or improvements or changes in vitals of patients 208 of provider 204. For example, health information processing system 202 may generate the screenshot of FIG. 58 to show improvements in vitals of a selected patient 208. In some embodiments, the vitals are displayed in bar charts to show the health applications used by patients 208 for each vital. Each chart shows a vital with each bar indicating a health application.

In various embodiments, health information processing system 202 generates analytics of patients 208 For example, health information processing system 202 generates analytics and corresponding charts of numbers of patients 208 of provider 204 that are part of system 202 and using health applications relative to patients of other providers 204. In response to a selection of a chart element, health information processing system 202 may list or chart all patients (e.g., by name) in groups based on attributes (e.g., age ranges and body mass index).

In various embodiments, health information processing system 202 generates analytics of health applications or health data source 227 or bundles thereof. For example, health information processing system 202 generates analytics and corresponding charts of health applications or health data sources 227 or bundles thereof recommended by system users 201 that are logged in and adherence by patients 208 and corresponding improvements or changes in vitals of patients of provider 204.

Figure 57:
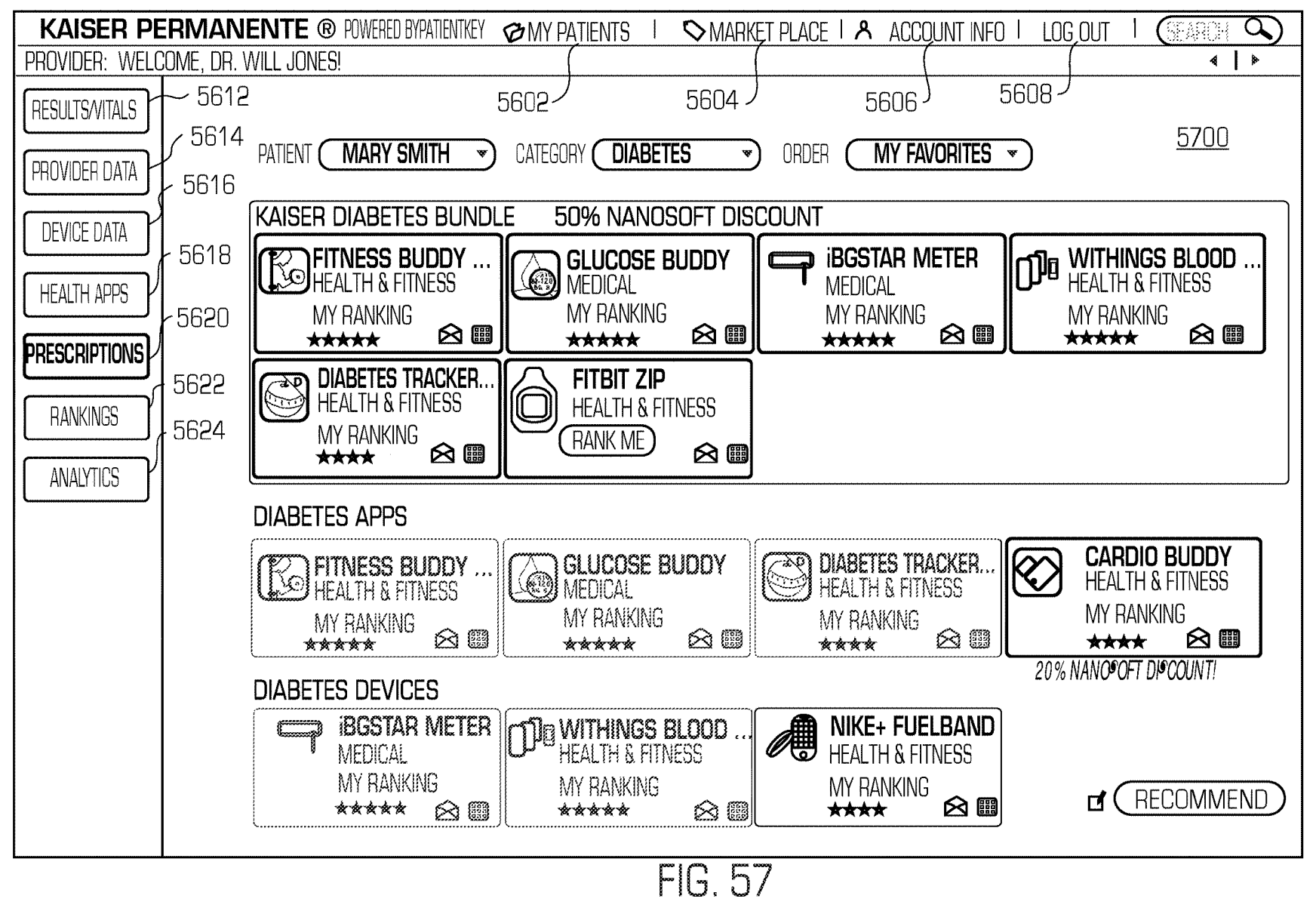

FIG. 57 illustrates a screenshot 5700 of a patient 208 selected by provider 204 from screenshot 5600. Screenshot 5700 comprises results/vitals icon 5612, provider data icon 5614, device data icon 5616, health applications icon 5618, prescriptions icon 5620, rankings icon 5622, and analytics icon 5624. In the illustrative example shown in FIG. 57, provider 204 has selected prescriptions icon 5620. In this illustrative example, provider 204 is prescribing a diabetes bundle including fitness devices and health applications, blood glucose device and health applications and blood pressure monitoring device. Other patients of the provider 204 use these devices and health applications. In this illustrative example of screenshot 5700, the displayed health applications and health data sources 227, which are ranked (a five star PKP ranking), of the physician 222 are displayed. A discount is shown by the employer of the associated patient. Discounts are described in conjunction with FIG. 61.

Figure 58:
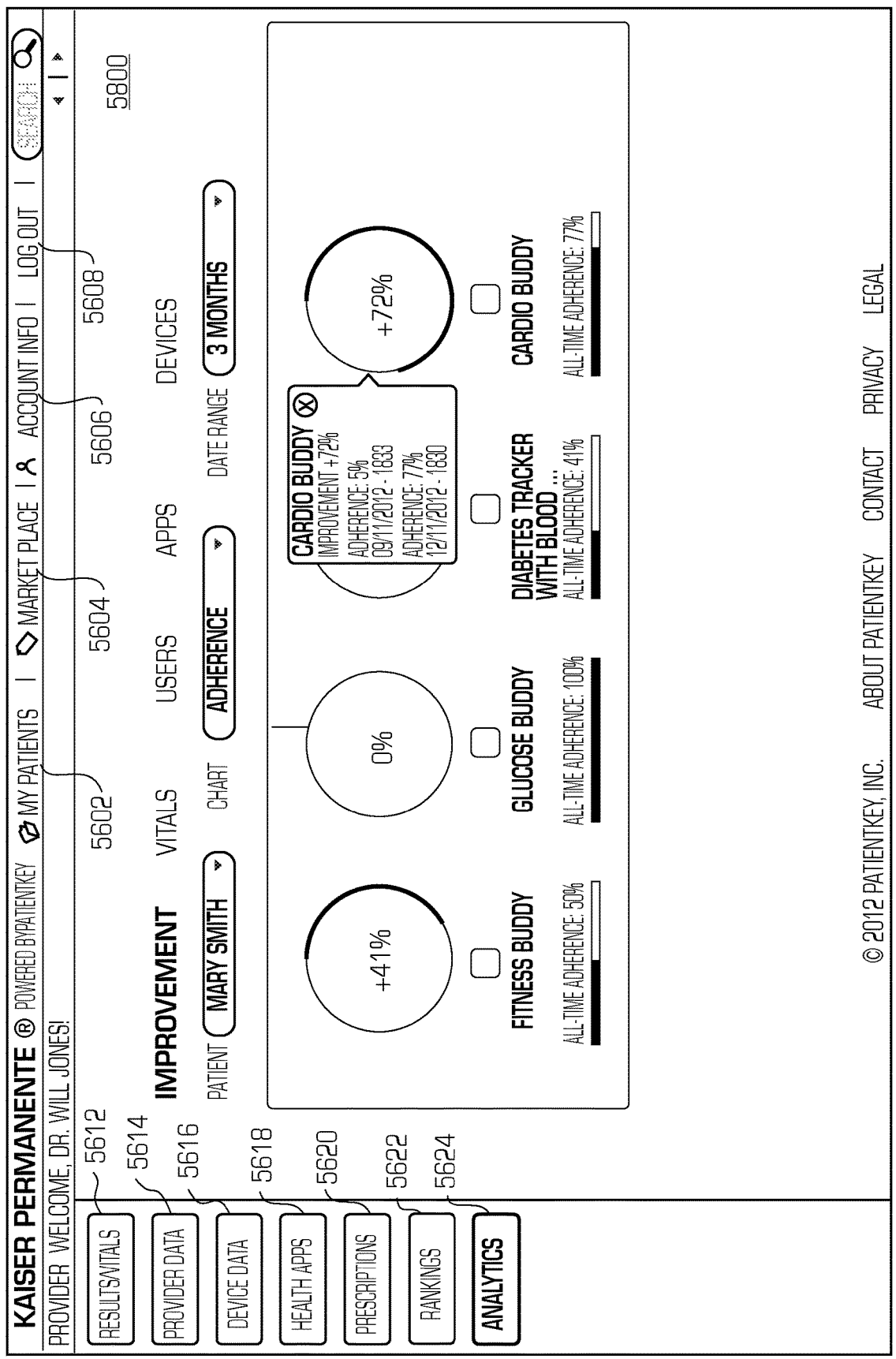
FIG. 58 illustrates a screenshot of analytics of medical data of the patient of the screenshot of FIG. 57.

FIG. 58 illustrates a screenshot 5800 of analytics of medical data of the patient of the screenshot 5700. Health information processing system 202 displays, in screenshot 5800, vitals and adherence data of patient 208. Provider 204 can select the vitals and the time periods to view short and long-term usage of health care devices 227, health applications, or bundles, and determine whether patient 208 understands the prescribed health care devices 227, health applications, or bundles, and assess whether compliance and commitment of patient 208 to treatment and regiment for improving or maintaining health.

FIG. 59 illustrates a screenshot 5900 of consolidated data of health data device 227 of patient 208. Screenshot 5900 may be displayed, for example, in response to the selection of "my applications icon" 717 (FIGS. 7-14), results/vitals selection element 730h (FIG. 7), or, if patient 208 has authorized access by provider 204, patient data selection element 2130a (FIG. 21). Screenshot 5900 comprises a "my apps" icon 5902, a marketplace icon 5904, an account information icon 5906, and a log out icon 5908. "My apps" icon 5902 allows patient 208 to access, add, or modify information related to health data devices 227 and health applications of patient 208. Marketplace icon 5904 allows patient 208 to access, add, or modify information related to the available health care devices 227 and health care applications including the ranking and number of users 201. In various embodiments, marketplace icon 5904 is similar to marketplace icon 617. Account information icon 5906 allows patient 208 to access, add, or modify account information such as password, contact information (such as email address, physical address, or phone number) or user name. In various embodiments, account information icon 5906 is similar to account information selection element 710. Log out icon 5908 allows patient 208 to logout of health information processing system 202.

Screenshot 5900 further comprises a results/vitals icon 5912, a personal data icon 5914, a data sharing icon 5916, a device data icon 5918, a health applications icon 5920, a rankings icon 5922, and a history icon 5924.

In response to selection of results/vitals icon 5912, health information processing system 202 generates a screenshot for patient that displays a snapshot or summary of data from health data devices 227 and health applications of patient 208. Screenshot 5900 includes may be, for example, the screenshot or a subset of the screenshot generated in response to selection of results/vitals selection element 730h, or may include further information generated by health information processing system 202. In some embodiments, screenshot 5100 (FIG. 51) may be displayed instead of screenshot 5900.

Personal data icon 5914 allows patient 208 to access, add, or modify information related to patient data, such as patient name, contact information, health information and the like, for patient 208.

Data sharing icon 5916 allows patient 208 to access, add, or modify information related to sharing data with providers 204, family, friends, caregivers, conservators, lawyers, or social workers, or groups. In various embodiments, data sharing icon 5916 is similar to of data disclosure selection element 730b (FIG. 7).

Device data icon 5918 allows patient 208 to access, add, or modify information related to health care devices 227 used by patients 208, recommended for use by provider 204, rankings, number of users, analysis by health information processing system 202 of health care devices 227, and a search icon for patients 208 to search available health care devices 227 for a specific medical condition. The analysis by health information processing system 202 may provide overall effectiveness of health care device 227 and patient satisfaction with health care device 227. In various embodiments, device data icon 5918 is similar to data device selection element 730c (FIG. 7). In various embodiments, health information processing system 202 generates screenshot 1000 in response to selection of device data icon 5918.

Health applications icon 5920 allows patient 208 to access, add, or modify information related to health applications recommended by provider 204 and used by patients 208 of provider 204, rankings, number of users, analysis by health information processing system 202 of the health applications, and a search icon for patient 208 to search available health applications for a specific medical condition. The analysis by health information processing system 202 may provide overall effectiveness of health applications and patient satisfaction with health applications. In various embodiments, health applications icon 5920 is similar to health applications selection element 730d (FIG. 7). In various embodiments, health information processing system 202 generates screenshot 1100 in response to selection of health applications icon 5920.

Rankings icon 5922 allows patient 208 to access, add, or modify information related to ranking of health care devices 227, health applications, or providers 204, and review health ranking history. In some embodiments, rankings icon 5922 is similar to rank selection element 730g (FIG. 7). In various embodiments, health information processing system 202 displays screenshot 1400 (FIG. 14) in response to selection of rankings icon 5922.

Figure 60:
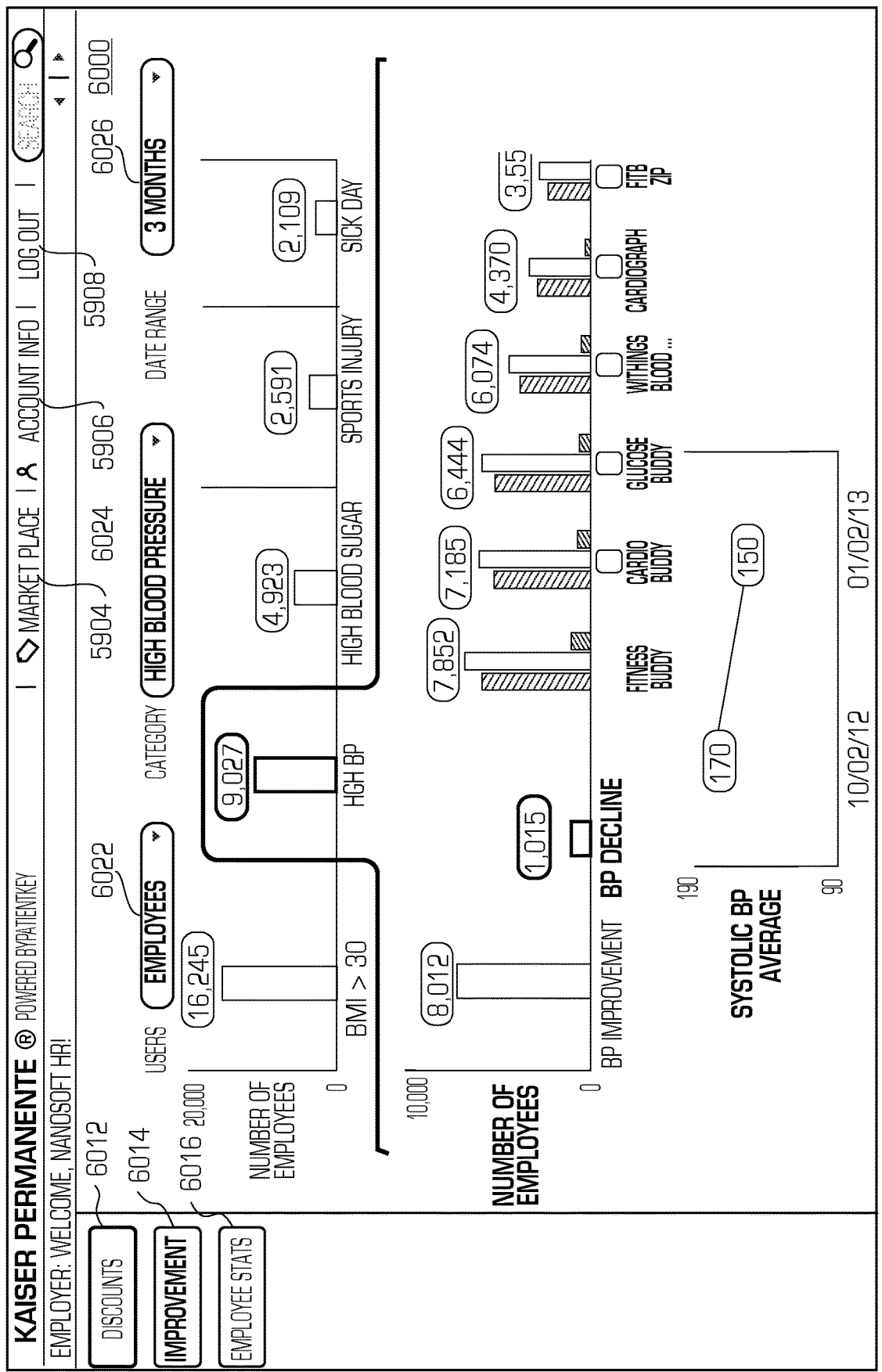
FIG. 60 illustrates a screenshot of improvements of employees of an employer in the process of FIG. 24.

FIG. 60 illustrates a screenshot 6000 of health care sponsor 230 that is an employer. Screenshot 6000 may be displayed, for example, at 2404 (FIG. 24) for health care sponsor 230 that is an employer. For simplicity and clarity, health care sponsor 230 is referred to as employer 230 herein in conjunction with FIGS. 60 and 61. Screenshot 6000 comprises marketplace icon 5604, account information icon 5606, log out icon 5608, a discount icon 6012, an improvement icon 6014, and an employee stats icon 6016.

Discount icon 6012 allows employer 230 to access, add, or modify information related to discounts offered to employees on health data devices 227, health applications, or bundles thereof. In some embodiments, health information processing system 202 analyzes data of employees and determines medical conditions or health conditions that warrant improvement and determines recommendations of health data devices 227, health applications, or bundles thereof. Employer 230 may offer discounts to employees based on the recommendations. In some embodiments, health information processing system 202 generates screenshots, such as bar graphs, of numbers of employees having health conditions (e.g., high blood pressure (9027), body mass index-BMI>30 (16,245), high blood sugar (4,923), sick day (2109), and sport Injury (2,591)). Below the bar graph, health information processing system 202 lists medical conditions that should be fixed and recommended health applications with overall (PKP) ranking and discount offered by employer 230 to employees. In some embodiments, the discount is visible in screenshot 6000 only to employees of employer 230.

Improvement icon 6014 allows employer 230 to access, add, or modify information related to changes or improvements in employee's health. Screenshot 6000 shows an illustrative example of health of employees of employer 230 while improvement icon 6014 is selected. Screenshot 6000 displays changes in employees' health over a selected period (1 month, 3 months, 6 months, 12 months, date range) as well as variable period or during special time period (e.g., Thanks giving and Christmas).

Screenshot 6000 further comprises a user icon 6022, a category icon 6024, and a time period icon 6026. User icon 6022 allows employer 230 to access, add, or modify information related to types of users of health information processing system 202 that are employees of employer 230. The users may be, for example, all users, executives, managers, or employees.

Category icon 6024 allows employer 230 to access, add, or modify information related to types of medical condition, vitals, health condition, or status of user. The categories may be, for example, medical condition, body mass index, blood pressure, blood glucose, sport injury, or sick day (off day).

Time period icon 6026 allows employer 230 to access, add, or modify information related to the time period for which the data is analyzed. The time period may be, for example, distribution over time, all day, top quarter, top half, or selected top percent, or selected time period (e.g., 1 month, 3 month, 6 month, 12 month, or user selected time period).

Upon selection of icons 6022, 6024 and 6026, health information processing system 202 displays the data. For example, a graph is displayed with average (e.g., black color graph) with improvements in one color (e.g., green) and declines in another color (e.g., red). The graph may also include numbers of employees. The graphs may include information about health data devices 227 and health applications that are being used and the improvements or changes in users of such devices and applications.

Employee stats icon 6016 allows employer 6001 to access, add, or modify information related to employee statistics. Employee statistics may include, for example, information on when employees joined health information processing system 202 or how many joined during specific time periods (e.g., last week, last month or last three months), and numbers of employees that synchronize data of their health data devices 227 and health applications.

Figure 61:
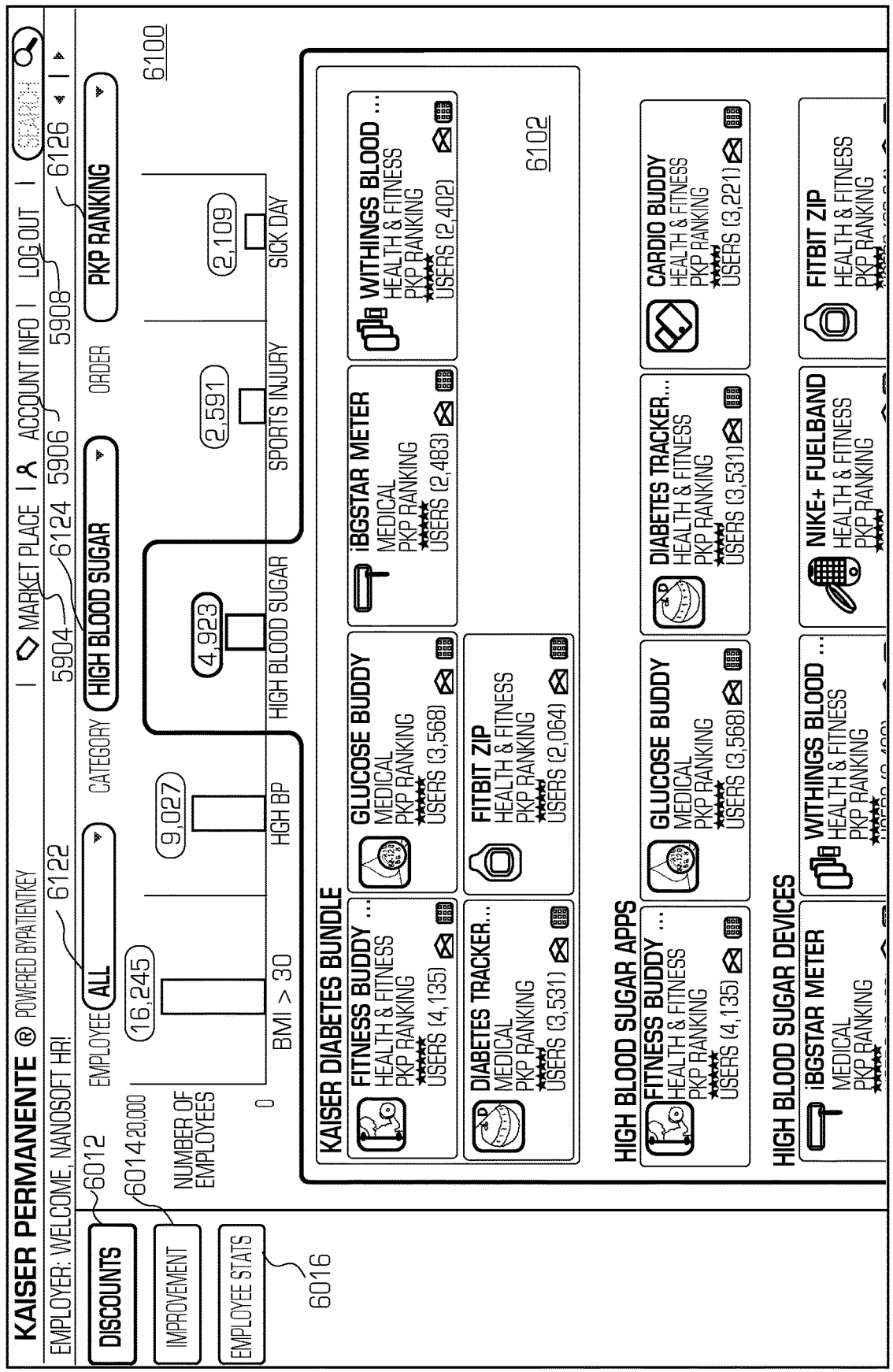
FIG. 61 illustrates a screenshot of discounts offered to employees of an employer in the process of FIG. 24.

FIG. 61 illustrates a screenshot 6100 of employer 230 in response to selection of discount icon 6012. Screenshot 6100 comprises marketplace icon 5604, account information icon 5606, log out icon 5608, discount icon 6012, improvement icon 6014, and employee stats icon 6016. Screenshot 6100 shows an illustrative example of discounts upon selection of discount icon 6012. Screenshot 6100 further comprises an employee icon 6122, a category icon 6124, and an order ranking 6126.

Employee icon 6122 allows employer 230 to access, add, or modify information related to types of users of health information processing system 202 that are employees of employer 230 for which discounts will be offered to employees. The users may be, for example, all users, executives, managers, or employees. Category icon 6124 allows employer 230 to access, add, or modify information related to types of health data devices 227, health applications, or bundles thereof for which discounts will be offered to employees. Order ranking icon 6126 allows employer 230 to access, add, or modify information related to an order health data devices 227, health applications, or bundles thereof will be displayed. The order may be, for example, based on overall (e.g., PKP) ranking, patient ranking, provider ranking, price, priority of health issues, and the like.

Figure 62:
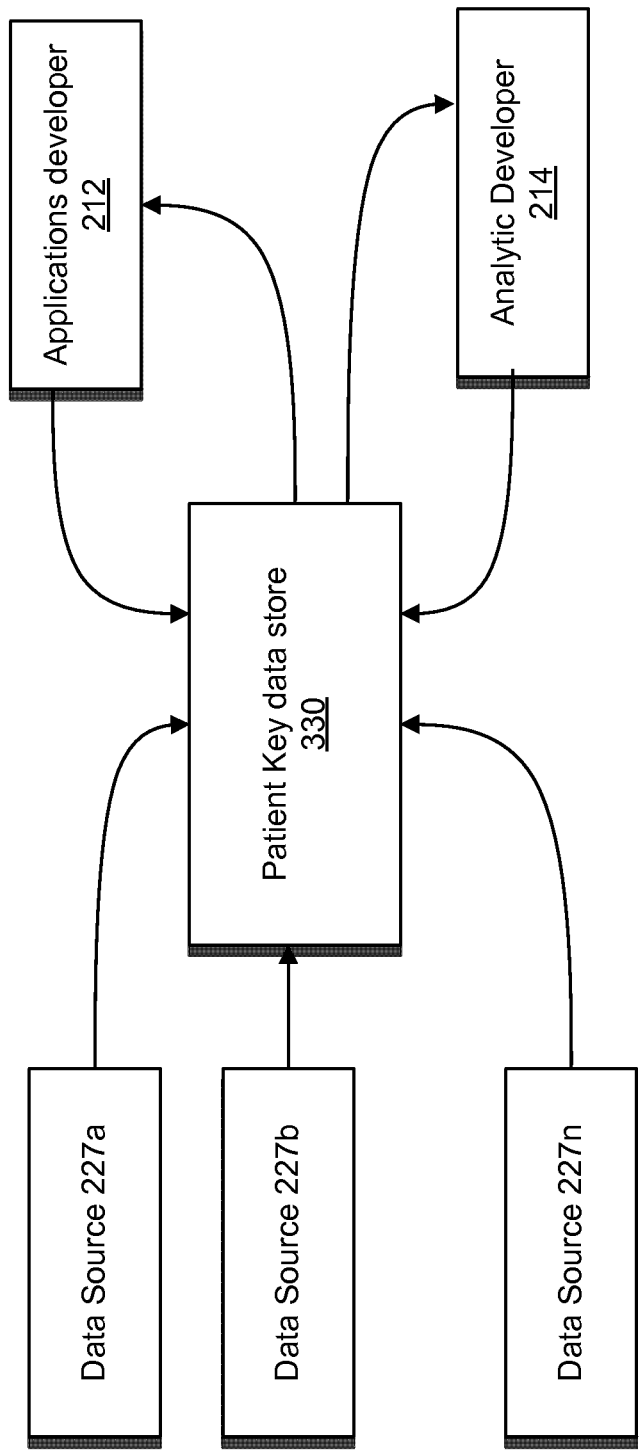
FIG. 62 illustrates a block diagram of application interfaces for applications developers and analytics developers of the health data processing system of FIG. 2.
Figure 63A:
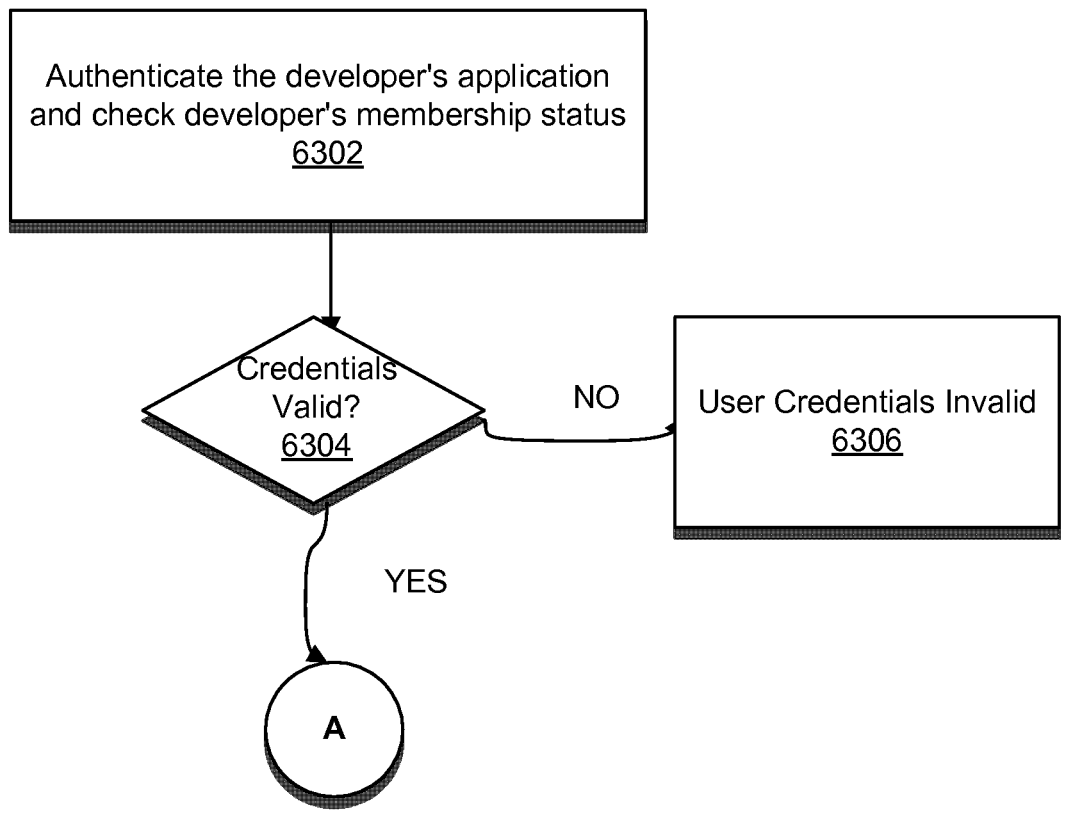
FIGS. 63a, 63b, 63c, and 63d illustrate a process for accessing by, a health application developer, data of the health data processing system of FIG. 2.
Figure 63B:
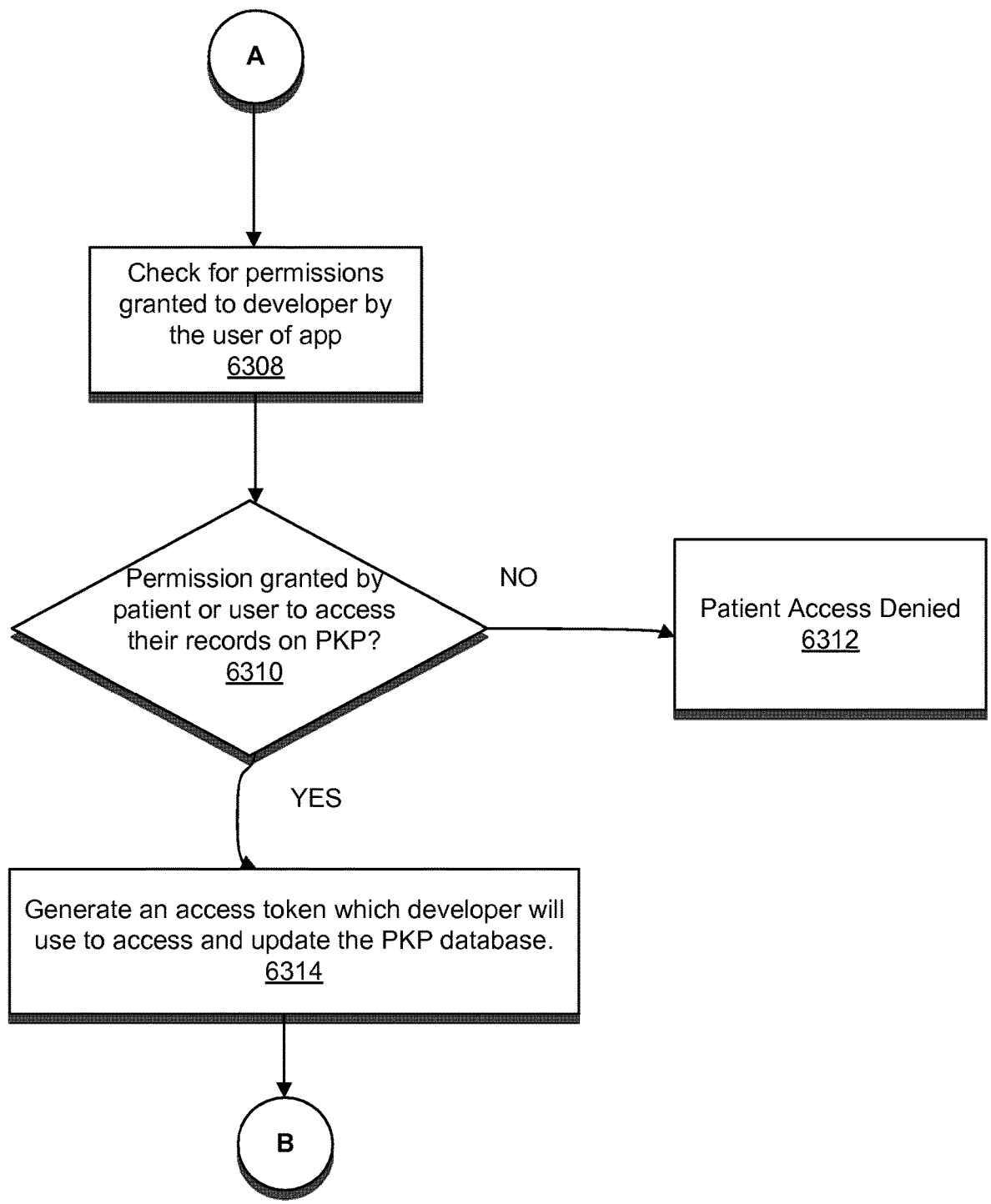
Figure 63C:
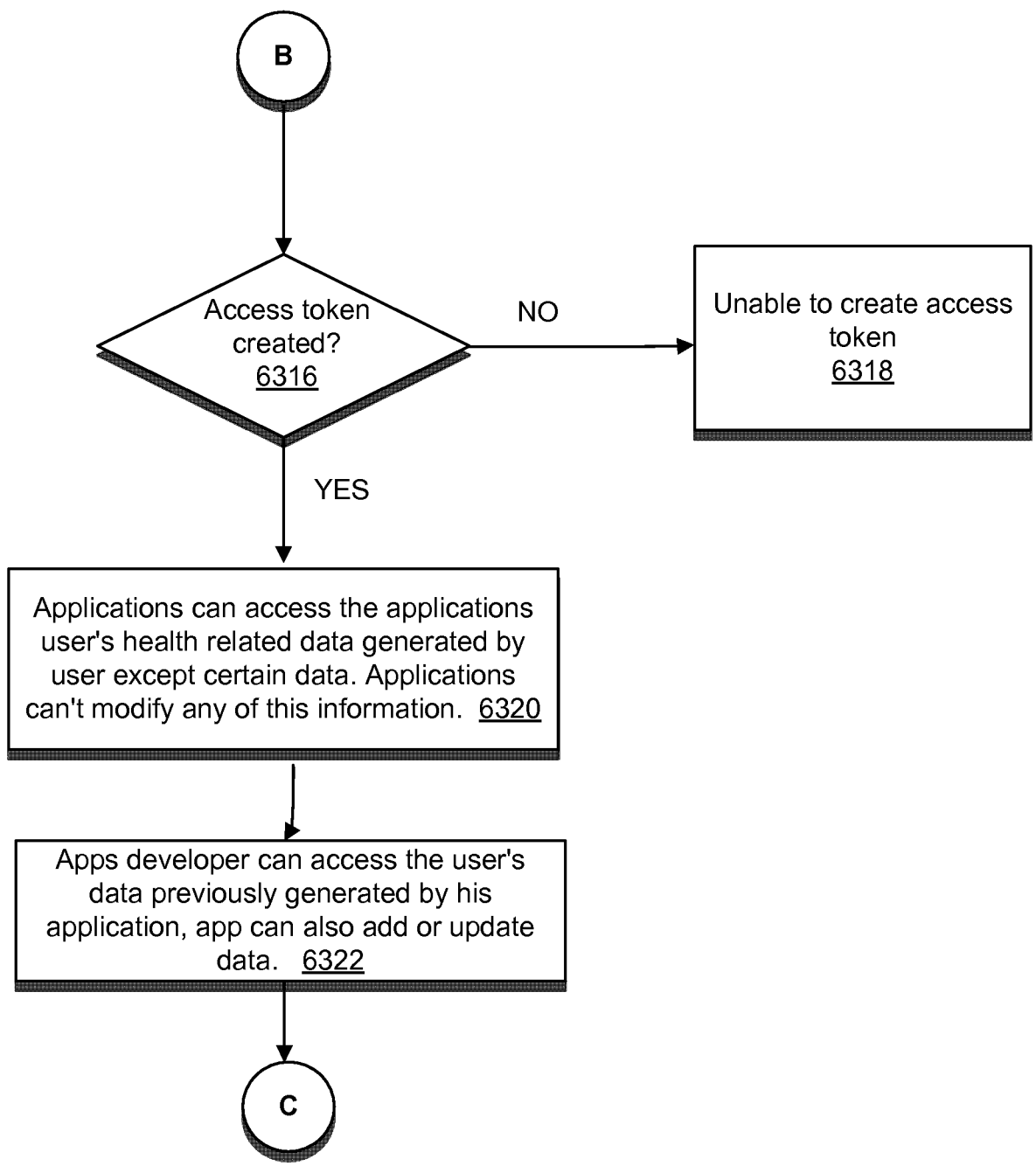
Figure 63D:
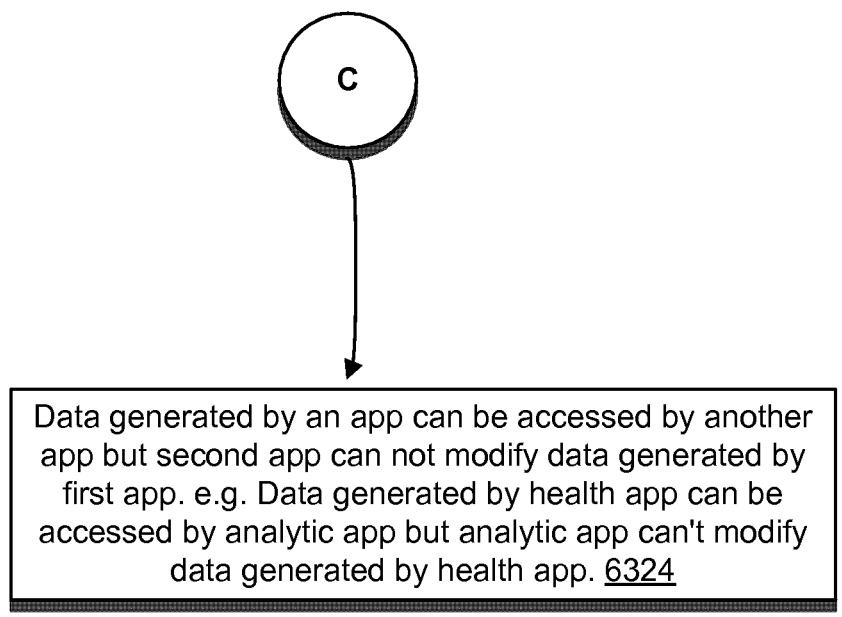

FIG. 62 illustrates a block diagram of application interfaces for applications developers 212 and analytics developers 214. Data store 330 stores data from data sources 227a, 227b, through 227n. As described above, patients 208 authorize the access of data stored in data store 330 to other system users 201 based on type of system user 201 as well as specific system user 201. Health information processing system 202 generates a software development kit (SDK) and application programming interface (API) for reading and writing information into data store 330.

Health data source developer 212 generates a SDK/API for health data source 227 and publishes them on health information processing system 202. Analytics developers 214 retrieve the SDK/API for generating health applications, and retrieve the data of patients 208 to generate the health applications. Applications developers 212 and analytics developers 214 determine the fields of data that are to be read, written or updated.

An application programming interface may be in hierarchical and object-oriented programming languages and use sophisticated programming language constructs. The API may include data mining functionality. The API may include a mining object repository maintaining data mining metadata, a plurality of mining project objects with each mining project object including data mining objects created and used by a user 201 and a plurality of mining session objects. A mining session object may include data mining processing performed on behalf of a user 201 and a plurality of data mining tables.

FIGS. 63a, 63b, 63c, and 63d illustrate a process for accessing by, a health application developer 212, data of the health data processing system 200. Software development engine 314 provides an interface through client interface 302 to health data source developers 212 and analytics developers 214 to access health information processing system 202 for reading and writing information in data store 330 and software development engine 314 for developing software.

In various embodiments, health data source developers 212 and analytics developers 214 can access information stored in data store 330 by using a set of APIs. First, health data source developers 212 and analytics developers 214 pass their credentials to create a secure connection to software development engine 314. Health data source developers 212 and analytics developers 214 can choose the fields they want to read or update.

At 6302, security engine 304 authenticates the developer's application and checks the developer's membership status. If, at 6304, the credentials are not valid, at 6306, security engine 304 rejects the attempt to access software development engine 314. If, at 6304, the credentials are valid, at 6308, security engine 304 checks for permissions that are granted to the developer by the user of the health application.

If, at 6310, permissions are not granted by patient 208 or the user to access their records in data store 330, at 6312, security engine 304 denies access to patient data. If, at 6310, permission is granted by patient 208 or the user to access their records in data store 330, at 6314, security engine 304 allows access to the associated data in data store 330, such as by generating an access token that the developer uses to access and update data store 330.

If, at 6316, an access token had not been created, at 6318, security engine 304 indicates that an access token was not created. In some embodiments, security engine 304 provides a help screen or a request for the developer to reattempt to create an access token. If, at 6316, an access token had been created, at 6320, security engine 304 allows the developer to access data store 330 and the health related data generated by system users 201. In some embodiments, data is redacted so that the developer cannot access certain information such as user name, identifiers, such as social security number or complete contact information. In some embodiments, the developers cannot modify any of the user information.

At 6322, security engine 304 allows the developer to access the user's data that the developer had previously generated by his application. Further, security engine 304 allows the developer to add or update the data. At 6324, security engine 304 allows a developer to access, but not modify, the data developed by another developer. For example, an analytics developer 214 can access, but cannot modify, the data generated by a health data source developer 212.

Figure 64A:
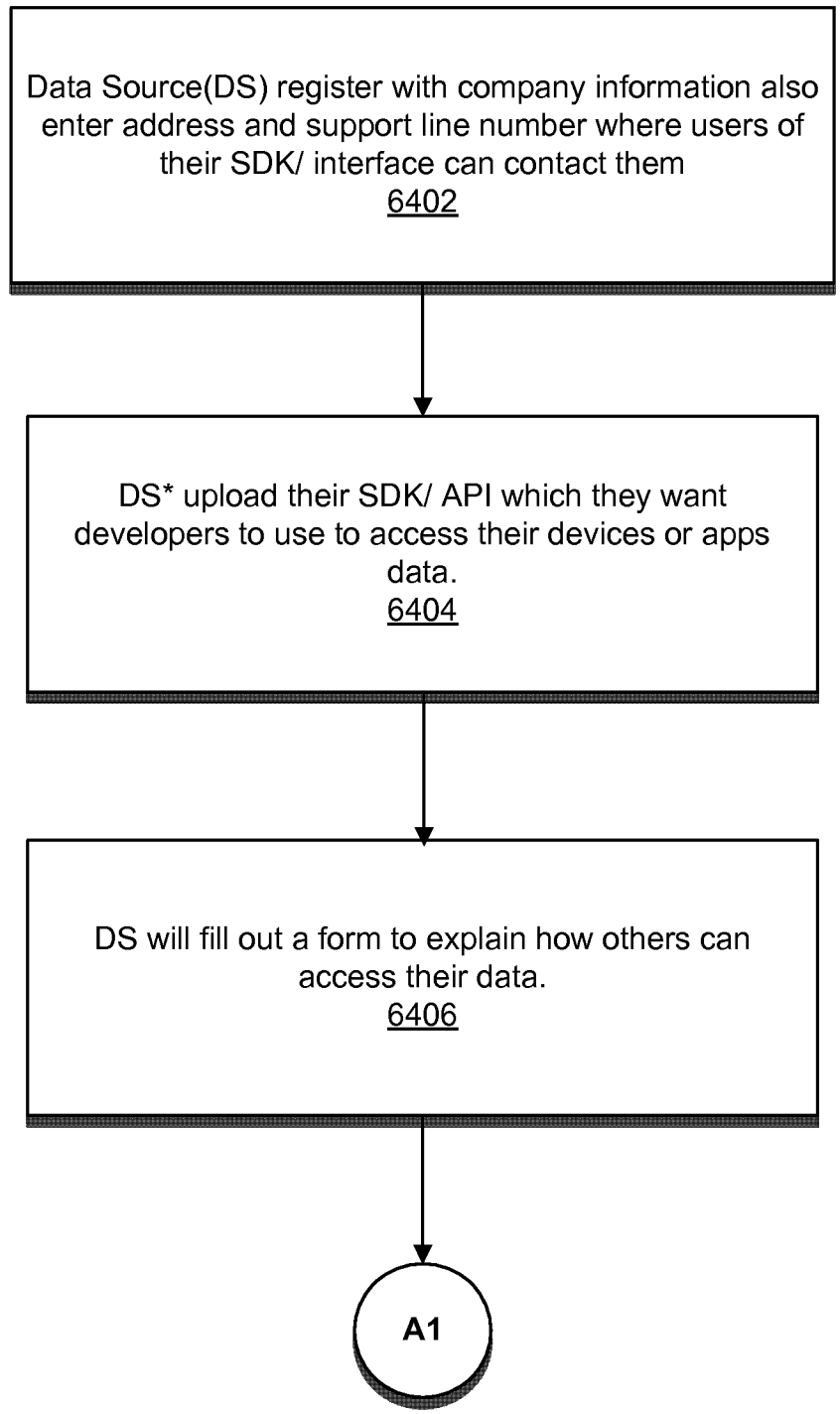
FIGS. 64a, 64b, and 64c illustrate a process for providing a software development kit and application programming interface by a health data source developer of the health data processing system of FIG. 2.
Figure 64B:
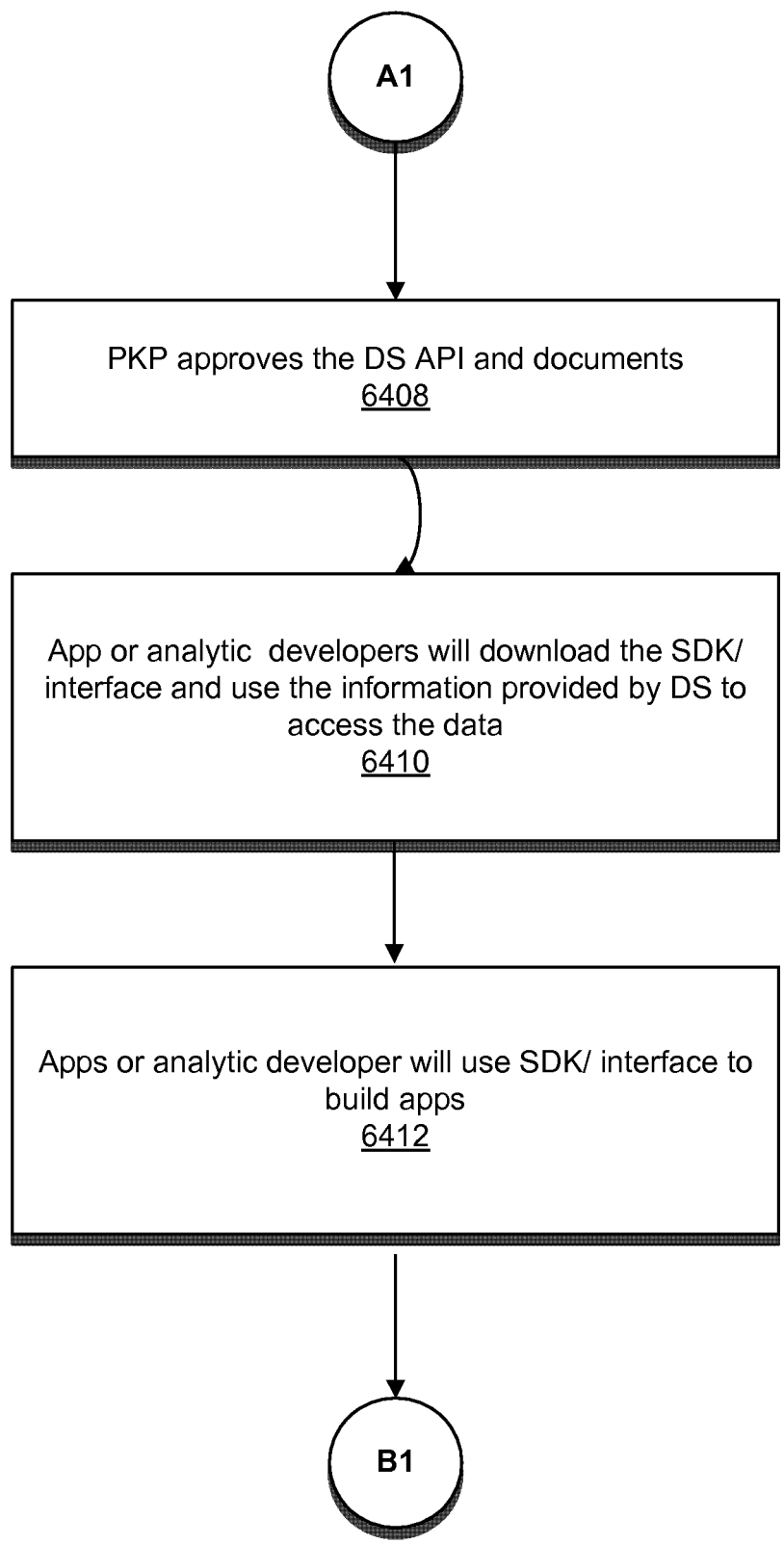
Figure 64C:
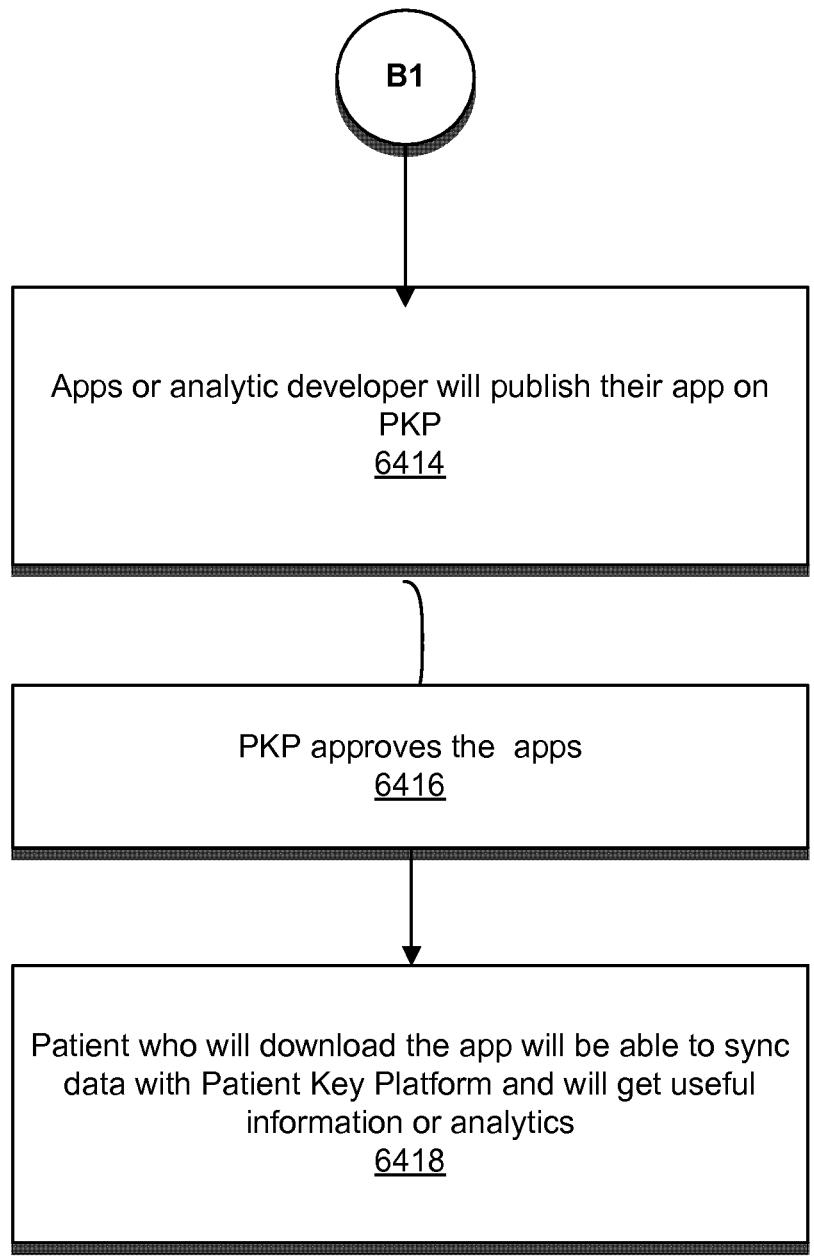

FIGS. 64a, 64b, and 64c illustrate a process for providing a software development kit (SDK) and application programming interface (API) by a health data source developer 212. The process of FIGS. 64a, 64b, and 64c may be in response to selection of interface specification selection element 3430e (FIG. 34). At 6402, health information processing system 202 provides a user interface for health data source developer 212 to register with health information processing system 202 by providing company information and contact information (address, email, and support line number) for contact by users of their SDK/API. At 6404, health information processing system 202 receives upload of software development kit and application programming interface from health data source developer 212 for use by analytics developers 214. At 6406, health information processing system 202 receives information from health data source developer 212 for describing how others can access data from health data source developer 212. The information may be received via a form.

At 6408, health information processing system 202 approves the application programming interface and other documents from health data source developer 212. At 6410, health information processing system 202 provides access to the approved SDK/API for download by analytics developers 214. At 6412, software development engine 314 develops applications using the SDK/API in response to input from analytics developers 214.

At 6414, health information processing system 202 receives applications from analytics developers 214 for publication. At 6416, health information processing system 202 evaluates the applications, and if approved, places the application in the marketplace. At 6418, health information processing system 202 allows patient 208 to download the application, and synchronize data with health information processing system 202 using device data upload selection element 1030*b*.

The above description illustrates various embodiments of the present invention along with examples of how aspects of the present invention may be implemented. The above examples and embodiments should not be deemed to be the only embodiments, and are presented to illustrate the flexibility and advantages of the present invention as defined by the following claims. Based on the above disclosure and the following claims, other arrangements, embodiments, implementations and equivalents will be evident to those skilled in the art and may be employed without departing from the spirit and scope of the invention as defined by the claims.

What is claimed is:

1. A computer-implemented method comprising:
receiving, by a controller, a user request from a first system user of a plurality of system users for a communication of health data with a health information system,
wherein the health information system includes the controller and a data store that stores health data related to the plurality of system users;
determining, by the controller, whether the user request is a request for health data associated with a second system user or a request for an analysis of health data associated with the first group of system users or a request to communicate health data;
providing to the first system user, by the controller, health data stored by the second system user in the data store based on access approval by the second system user in response to the user request being a user request for health data associated with the second system user;
analyzing, by the controller, health data for a first group of system users in response to the user request being a request for an analysis of health data associated with the first group of system users;
providing, by the controller, to the first system user the analyzed health data for the first group of system users;
altering monitoring of health data of the patient based on the analyzed health data for the first group of system users indicating a request for additional health data of a patient;
altering treatment to the patient based on the analyzed health data for the first group of system users indicating a change to treatment to the patient; and
communicating, by the controller, health data associated with the first system user to a second group of system users in response to the user request being a request to communicate health data and the first system user has designated the system users of the second group of system users.

2. The method of claim 1, wherein the plurality of system users includes a plurality of health care providers, a plurality of payers, a plurality of patients, a plurality of health data source developers, and a plurality of health analytics developers.

3. The method of claim 1 further comprising:
receiving first ranking for a third system user from a third group of system users;
generating a first composite ranking of the third system user based on the rankings of the third system user.

4. The method of claim 3 further comprising:
receiving second rankings for the third system user from a fourth group of system users;
generating a second composite ranking of the third system user based on the second rankings of the third system user;
generating a second overall composite ranking of the third system user based on the first and second rankings of the third system user;
determining, for each of the first rankings, whether said each first ranking is to be adjusted based on data related to the corresponding system user of the third group of system users;
adjusting the first rankings for each corresponding system user of the third group of system users for which an adjustment to said first ranking is determined; and
adjusting the first overall composite ranking of the third system user based on the adjusted first rankings of the third system user.

5. The method of claim 1, wherein the first system user is a patient and the first user request is a download of health data from at least one heath data source of the patient at a selected one of an automatic download or a patient initiated download.

6. The method of claim 1, wherein the first system user is a health care provider and the first user request is an upload of health data of a patient from the data store, the method further comprising selecting a health care application for use by the patient on a health data source based on the uploaded health data.

7. The method of claim 1 further comprising:
determining, by the controller, from the health data of a group of patients in the plurality of system users efficacy of at least one of health data device used by the group of patients, health applications used by the group of patients, or medications taken by the group of patients;
determining, by the controller, from the health data of a group of patients in the plurality of system users trends in the health of said group of patients of at least one of health data device, health applications, or medications; and
determining, by the controller, potential chronic health conditions in said group of patients based on said determined trends in the health of said group of patients.

8. The method of claim 1 further comprising:
receiving information for a plurality of health applications
adding the information for the plurality of health applications to an online health application store for access by system users that are patients.

9. The method of claim 1 further comprising:
retrieving first health data for the patient;
analyzing said first health data to generate a metric of health or wellness of said patient;
retrieving second health data from a plurality of health care sources associated with a plurality of patients and executing a health care application; and
analyzing said second health data to evaluate the health care application.

10. The computer-implemented method of claim 1 further comprising:
displaying, by the controller, a plurality of health data device icons, each health data device icons associated with a health data device used by a patient,
wherein the data store further stores health data related to the patient;
displaying a plurality of health application icons, each health application icon associated with a health application used by the patient;

associating each health data device with any health applications used by the patient; and displaying, for each health data device, a connection with each associated health application.

11. The computer-implemented method of claim 1 further comprising receiving, by the controller, a plurality of first rankings for a health system from a plurality of patients;

receiving a plurality of second rankings for the health system from a plurality of providers;

generating a composite patient ranking for the health system based on the plurality of first rankings;

generating a composite provider ranking for the health system based on the plurality of second rankings; and generating a composite overall provider ranking for the health system based on the plurality of first rankings and the plurality of second rankings.

12. The method of claim 11, wherein generating a composite patient ranking for the health system from the plurality of first rankings includes, for each patient, adjusting the ranking based on usage of the health system by the patient and determining a weighting of the patient ranking, wherein generating a composite provider ranking for the health system from the plurality of second rankings includes, for each provider, adjusting the ranking based on prescriptions of the health system by the provider and determining a weighting of the provider ranking.

13. The computer-implemented method of claim 1 further comprising:

receiving, by the controller, a device developer request from a device developer for a communication with a health information system, wherein the data store further stores a device development document for a health data device and a standard interface specification;

analyzing, by the controller, the device developer request;

upon determining the device developer request is a request for the standard interface specification, downloading the standard interface specification to the device developer;

upon determining the device developer request is a request for uploading the device development document to the health information system, uploading the device development document to the health information system; and analyzing the device development document to determine whether the device development document complies with the standard interface specification.

14. The computer-implemented method of claim 1 further comprising:

receiving, by the controller, a device developer request from a device developer for a communication of device data with a health information system, wherein the data store further stores the device data;

analyzing, by the controller, the device developer request;

upon determining the device developer request is a data upload request, uploading the device data to the health information system;

upon determining the device developer request is a specification upload request, uploading an interface specification of a health data device to the health information system;

receiving a request for the interface specification from a health applications developer; and upon authorizing the health application developer, providing the interface specification to the health application developer.

15. The computer-implemented method of claim 1 further comprising:

displaying, by the controller, a plurality of health data item icons, each health data item icons associated with a health data item related to a patient, wherein the data store further stores the health data items related to the patient;

receiving a selection of at least one health data items from the patient;

displaying a list of system users;

receiving, for each selected health data item, a selection at least one system user; and authorizing, for each selected health data item, access to the associated health data item by the at least one selected system user for sharing the selected health data item with the at least one selected system user.

16. The method of claim 15, wherein the system users include members of a medical provider network, other patients having the same disease as the patient, other patients using the same health application as the patient, using the same health data device as the patient, or the same bundle of health application and health data deice as the patient.

17. The computer-implemented method of claim 1 further comprising:

receiving, by the controller, a patient request from a patient for a communication of health data with a health information system, wherein the data store further stores health data related to the patient;

analyzing, by the controller, the patient request;

upon determining the patient request is an upload request, uploading health data related to the patient from patient input, a health data source or a health application to the health information system; and upon determining the patient request is an analysis request downloading analysis of health data related to the patient.

18. The method of claim 17, further comprising:

generating advertising based on the prioritization of health issues of the patient in response to the patient request being a prioritization of health issues;

generating advertising based on the prioritization of chronic health of the patient in response to the patient request being a prioritization of chronic health;

displaying at least one health data device, at least one health application or a bundle of at least one health data device and at least one health application available to the patient based on the health data related to the patient in response to the patient request being a marketplace request;

displaying recommendations shared by the patient in response to the patient request being a recommendation review request; and displaying in a single screenshot data from all health data devices and health applications used by the patient in response to the patient request being a consolidation request.

19. The computer-implemented method of claim 1 further comprising:

receiving, by the controller, a provider request from a provider for a communication of health data with the health information system, wherein the data store further stores patient health data related to a patient;

analyzing, by the controller, the provider request;

upon determining the provider request is a prescription request, communicating a prescription to the patient; and upon determining the provider request is an analysis request downloading analysis of health data related to the patient.

20. The computer-implemented method of claim 1 further comprising:

receiving, by the controller, a payer request from a payer for a communication of health data with a health information system, wherein the data store further stores patient health data related to a patient and provider data related to a provider;

analyzing, by the controller, the payer request;

upon determining the payer request is a provider request, downloading analysis of health data related to the provider; and upon determining the payer request is a patient analysis request, downloading analysis of health data related to the patient.

\* \* \* \* \*